(12) United States Patent
Keilhack et al.

(10) Patent No.: US 10,301,290 B2
(45) Date of Patent: May 28, 2019

(54) COMBINATION THERAPY FOR TREATING CANCER

(71) Applicant: EPIZYME, INC., Cambridge, MA (US)

(72) Inventors: Heike Keilhack, Belmont, MA (US); Sarah Kathleen Knutson, Cambridge, MA (US); Kevin Wayne Kuntz, Woburn, MA (US)

(73) Assignee: Epizyme, Inc., Cambridge, MA (US)

( * ) Notice: Subject to any disclaimer, the term of this patent is extended or adjusted under 35 U.S.C. 154(b) by 298 days.

(21) Appl. No.: 14/394,463

(22) PCT Filed: Apr. 12, 2013

(86) PCT No.: PCT/US2013/036452
§ 371 (c)(1),
(2) Date: Oct. 14, 2014

(87) PCT Pub. No.: WO2013/155464
PCT Pub. Date: Oct. 17, 2013

(65) Prior Publication Data
US 2015/0051163 A1 Feb. 19, 2015

Related U.S. Application Data

(60) Provisional application No. 61/624,194, filed on Apr. 13, 2012, provisional application No. 61/785,169, filed on Mar. 14, 2013.

(51) Int. Cl.
| | |
|---|---|
| *C07D 213/64* | (2006.01) |
| *A61K 31/4412* | (2006.01) |
| *C07D 405/12* | (2006.01) |
| *A61K 31/5377* | (2006.01) |
| *A61K 45/06* | (2006.01) |
| *A61K 31/436* | (2006.01) |
| *A61K 31/53* | (2006.01) |
| *A61K 31/573* | (2006.01) |
| *A61K 31/704* | (2006.01) |
| *A61K 31/7068* | (2006.01) |
| *A61K 31/4745* | (2006.01) |
| *A61K 31/675* | (2006.01) |
| *A61K 33/24* | (2019.01) |

(52) U.S. Cl.
CPC .......... *C07D 405/12* (2013.01); *A61K 31/436* (2013.01); *A61K 31/4412* (2013.01); *A61K 31/4745* (2013.01); *A61K 31/53* (2013.01); *A61K 31/5377* (2013.01); *A61K 31/573* (2013.01); *A61K 31/675* (2013.01); *A61K 31/704* (2013.01); *A61K 31/7068* (2013.01); *A61K 45/06* (2013.01); *C07D 213/64* (2013.01); *A61K 33/24* (2013.01)

(58) Field of Classification Search
None
See application file for complete search history.

(56) References Cited

U.S. PATENT DOCUMENTS

| | | |
|---|---|---|
| 8,410,088 B2 | 4/2013 | Kuntz et al. |
| 8,691,507 B2 | 4/2014 | Copeland et al. |
| 8,765,732 B2 | 7/2014 | Kuntz et al. |
| 8,895,245 B2 | 11/2014 | Copeland et al. |
| 9,090,562 B2 | 7/2015 | Kuntz et al. |
| 9,175,331 B2 | 11/2015 | Kuntz et al. |
| 9,333,217 B2 | 5/2016 | Copeland et al. |
| 9,334,527 B2 | 5/2016 | Kuntz et al. |
| 9,522,152 B2 | 12/2016 | Kuntz et al. |
| 9,549,931 B2 | 1/2017 | Kuntz et al. |
| 2012/0071418 A1 | 3/2012 | Copeland et al. |

FOREIGN PATENT DOCUMENTS

| | | |
|---|---|---|
| WO | WO 2012/034132 A2 | 3/2012 |
| WO | WO 2012/118812 A2 | 9/2012 |
| WO | WO 2012/142504 | 10/2012 |
| WO | WO 2012/142513 A1 | 10/2012 |
| WO | WO 2013/138361 A1 | 9/2013 |
| WO | WO 2013/155317 A1 | 10/2013 |
| WO | WO 2013/173441 | 11/2013 |
| WO | WO 2015/085325 | 6/2015 |

OTHER PUBLICATIONS

Merriam-Webster's Collegiate Dictionary, published 1998 by Merriam-Webster, Incorporated, p. 924.*
Bostrom et al. "Dexamethasone versus prednisone and daily oral versus weekly intravenous mercaptopurine for patients with standard-risk acute lymphoblastic leukemia: a report from the Children's Cancer Group" Blood (2003) vol. 101 No. 10 pp. 3809-3817.*
Eiser et al., "HRQOL Implications of Treatment With Dexamethasone for Children With Acute Lymphoblastic Leukemia (ALL)" Pediatr Blood Cancer vol. 46 pp. 35-39 (Year: 2006).*
Roth et al., "Steroids in neurooncology: actions, indications, side-effects" Current Opinion in Neurology vol. 23 pp. 597-602 (Year: 2010).*
Veerman et al., "Dexamethasone-based therapy for childhood acute lymphoblastic leukaemia: results of the prospective Dutch Childhood Oncology Group (DCOG) protocol ALL-9 (1997-2004)" Lancet Oncology vol. 10 pp. 957-966 (Year: 2009).*
Hurwitz et al., "Substituting Dexamethasone for Prednisone Complicates Remission Induction in Children with Acute Lymphoblastic Leukemia" Cancer vol. 88, No. 8 pp. 1964-1969 (Year: 2000).*

(Continued)

*Primary Examiner* — Eric Olson
(74) *Attorney, Agent, or Firm* — Cooley LLP; Heidi A. Erlacher; Christine C. Pemberton

(57) ABSTRACT

The present invention relates to compositions comprising inhibitors of human histone methyltransferase EZH2 and one or more other therapeutic agents, particularly anticancer agents such as prednisone, and methods of combination therapy for administering to subjects in need thereof for the treatment of cancer.

9 Claims, 11 Drawing Sheets

Figure 1:
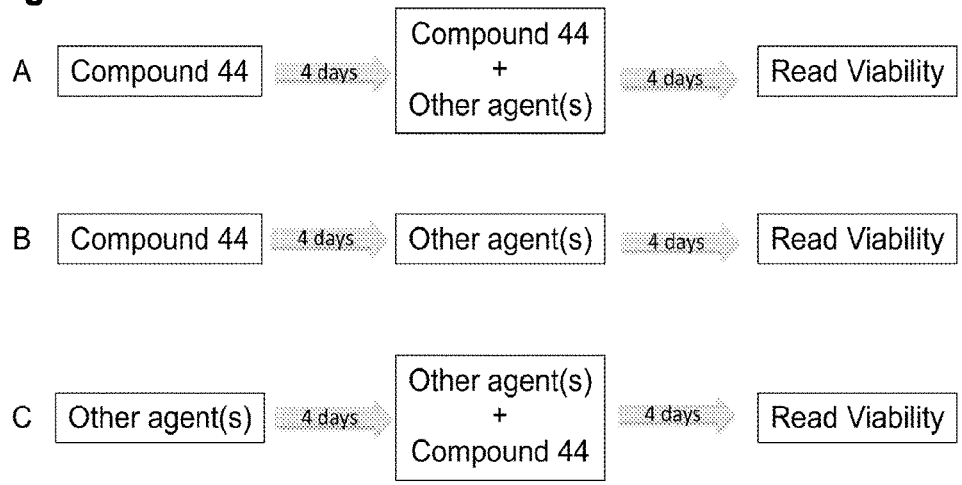

Specification includes a Sequence Listing.

(56) References Cited

OTHER PUBLICATIONS

Garapaty-Rao, S. et al. (Nov. 2013) "Identification of EZH2 and EZH1 Small Molecule Inhibitors with Selective Impact on Diffuse Large B Cell Lymphoma Cell Growth" *Chem Biol*, 20:1329-1339.

Knutson, S.K. et al. (2012) "A Selective Inhibitor of EZH2 Blocks H3K27 Methylation and Kills Mutant Lymphoma Cells" *Nat Chem Biol*, 8:890-896.

Qi, W. et al. (2012) "Selective inhibition of Ezh2 by a small molecule inhibitor blocks tumor cells proliferation" *Proc Natl Acad Sci USA*, vol. 109, No. 52, p. 21360-21365.

Varambally, S. et al. (2002) "The Polycomb Group Protein EZH2 Is Involved in Progression of Prostate Cancel" *Nature*, 419:624-629.

\* cited by examiner

A

B

C

D

A

B

C

A

*OCI-LY19 cells (EZH2 WT)*
*Resistant to EZH2i*

B

*WSU-DLCL2 cells (Y641F)*
*Sensitive to EZH2i*

C

*RL cells (Y641N)*
*Resistant to EZH2i*

| Cyclophosphamide | 30 mg/kg i.p. |
|---|---|
| Vincristine | 0.375 mg/kg i.v. |
| Doxorubicin | 2.475 mg/kg i.v. |
| Prednisolone | 0.15 mg/kg p.o. |
| Compound 44 | 225 mg/kg p.o. |

A

B

A (*) $p<0.05$ vs. vehicle
Repeated measures ANOVA, Dunnett's post test

B

*Plasma PK on day 28*

C.

*Tumor tissue PK on day 28*

A

B

A

*Tumor Growth*

B

*Tumor Weight on Day 28*

C

*Tumor Growth Delay- Survival*

D

*Survival*

A

*28 day PK results*

B

*28 day tumor PD results*

C

*Spleen*

D

*Bone Marrow*

COMBINATION THERAPY FOR TREATING CANCER

RELATED APPLICATIONS

This application is a U.S. National Phase application of International Application No. PCT/US2013/036452, filed Apr. 12, 2013, which claims priority to, and the benefit of, the U.S. Provisional Application No. 61/624,194 filed Apr. 13, 2012 and the U.S. Provisional Application No. 61/785,169 filed Mar. 14, 2013, the contents of each of which are incorporated by reference in their entireties.

INCORPORATION-BY-REFERENCE OF SEQUENCE LISTING

The contents of the text file named "EPIZ009001WO_ST25.txt," which was created on Oct. 14, 2014 and is 45 KB in size, are hereby incorporated by reference in their entireties.

PARTIES TO JOINT RESEARCH AGREEMENT

This invention was developed subject to a Joint Research Agreement between Epizyme, Inc. and Eisai Co., Ltd.

FIELD OF THE INVENTION

This invention relates to compositions comprising inhibitors of human histone methyltransferase EZH2, the catalytic subunit of the PRC2 complex which catalyzes the mono- through tri-methylation of lysine 27 on histone H3 (H3-K27), and one or more other therapeutic agents, particularly anticancer agents, and methods of combination therapy for treating cancer.

BACKGROUND OF THE INVENTION

Combination-therapy treatments for cancer have become more common, in part due to the perceived advantage of attacking the disease via multiple avenues. Although many effective combination-therapy treatments have been identified over the past few decades; in view of the continuing high number of deaths each year resulting from cancer, a continuing need exists to identify effective therapeutic regimens for use in anticancer treatment.

SUMMARY OF THE INVENTION

In one aspect, the present invention features a composition comprising a compound of Formula (IIa) below and one or more other therapeutic agents or a pharmaceutically acceptable salt or ester thereof.

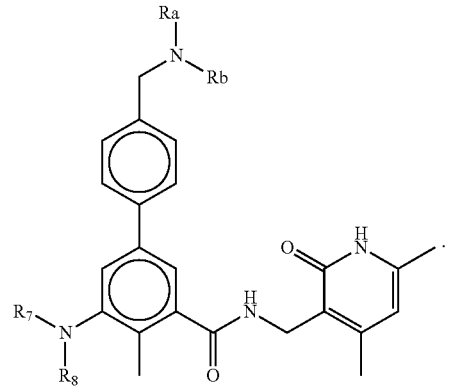

(IIa)

The compounds of Formula (IIa) can include one or more of the following features:

Each of $R_a$ and $R_b$, independently is H or $C_1$-$C_6$ alkyl.

$R_a$ and $R_b$, together with the N atom to which they are attached, is a 4 to 7-membered heterocycloalkyl ring having 0 or 1 additional heteroatom, the $C_1$-$C_6$ alkyl and the 4 to 12-membered (e.g., 4 to 7-membered) heterocycloalkyl ring being optionally substituted with one or more -$Q_3$-$T_3$.

$Q_3$ is a bond or unsubstituted or substituted $C_1$-$C_3$ alkyl linker.

$T_3$ is H, halo, 4 to 7-membered heterocycloalkyl, $C_1$-$C_3$ alkyl, $OR_d$, $COOR_d$, —$S(O)_2R_d$, or —$NR_dR_e$, each of $R_d$ and $R_e$ independently being H or $C_1$-$C_6$ alkyl.

$R_7$ is $C_1$-$C_6$ alkyl, $C_3$-$C_8$ cycloalkyl or 4 to 12-membered (e.g., 4 to 7-membered) heterocycloalkyl, each optionally substituted with one or more -$Q_5$-$T_5$. For example, $R_7$ is not H.

$R_7$ is 4 to 7-membered heterocycloalkyl optionally substituted with one or more -$Q_5$-$T_5$.

$R_7$ is piperidinyl, tetrahydropyran, cyclopentyl, or cyclohexyl, each optionally substituted with one -$Q_5$-$T_5$.

$T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 12-membered (e.g., 4 to 7-membered) heterocycloalkyl.

$Q_5$ is a bond and $T_5$ is $C_1$-$C_6$ alkyl, $C_3$-$C_8$ cycloalkyl, or 4 to 12-membered (e.g., 4 to 7-membered) heterocycloalkyl.

$Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered (e.g., 4 to 7-membered) heterocycloalkyl.

$Q_5$ is $C_1$-$C_3$ alkyl linker and $T_5$ is H or $C_6$-$C_{10}$ aryl.

$Q_5$ is $C_1$-$C_3$ alkyl linker and $T_5$ is $C_3$-$C_8$ cycloalkyl, 4 to 7-membered heterocycloalkyl, or $S(O)_qR_q$.

$R_7$ is cyclopentyl or cyclohexyl, each optionally substituted with one -$Q_5$-$T_5$.

$Q_5$ is NHC(O) and $T_5$ is $C_1$-$C_6$ alkyl or $C_1$-$C_6$ alkoxy.

$R_7$ is isopropyl.

Each of $R_2$ and $R_4$, independently is H or $C_1$-$C_6$ alkyl optionally substituted with amino, mono-$C_1$-$C_6$ alkylamino, di-$C_1$-$C_6$ alkylamino, or $C_6$-$C_{10}$ aryl.

$R_8$ is H, methyl, or ethyl.

$R_8$ is methyl.

$R_8$ is ethyl.

$R_8$ is 4 to 7-heterocycloalkyl, e.g., tetrahydropyran.

The present invention features a composition comprising a compound selected from Table 1 or a pharmaceutically acceptable salt or ester thereof and one or more other therapeutic agents.

The present invention features a composition comprising Compound 44

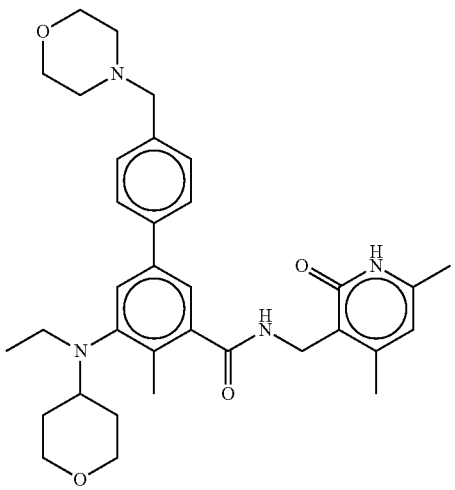

or a pharmaceutically acceptable salt or ester thereof and one or more other therapeutic agents.

In this and other aspects of the invention, in one embodiment the other therapeutic agents are anticancer agents.

In this and other aspects of the invention, in one embodiment the other therapeutic agents are glucocorticoids.

In this and other aspects of the invention, in one embodiment the other therapeutic agents are selected from prednisone, prednisolone, cyclophosphamide, vincristine, doxorubicin, mafosfamide, cisplatin, AraC, everolimus, decitabine, dexamethasone, and analogs, derivatives, or combinations thereof.

In this and other aspects of the invention, in one embodiment the other therapeutic agent is prednisone, or an analog or derivative thereof.

The present invention also provides pharmaceutical compositions comprising a compound selected from those of Formula (IIa) disclosed herein or pharmaceutical acceptable salts thereof and one or more therapeutic agents, and a pharmaceutically acceptable carrier.

The present invention also provides pharmaceutical compositions comprising a compound selected from Table I, one or more other therapeutic agents, or pharmaceutically acceptable salts thereof, and a pharmaceutically acceptable carrier.

The present invention also provides pharmaceutical compositions comprising a compound selected from those of Formula (IIa) disclosed herein or pharmaceutically acceptable salts thereof, one or more other therapeutic agents, and a pharmaceutically acceptable carrier.

Another aspect of this invention is a method for treating or preventing a disease by administering to a subject in need thereof a therapeutically effective amount of a composition comprising a compound of Formula (IIa), or a pharmaceutically acceptable salt thereof, and one or more additional therapeutic agents. The disease of the present invention can be influenced, treated, or prevented by modulating the methylation status of histones or other proteins. For example, the disease is cancer, a precancerous condition, or a neurological disease. Preferably, the lymphoma is non-Hodgkin lymphoma, follicular lymphoma or diffuse large B-cell lymphoma. Alternatively, the leukemia is chronic myelogenous leukemia (CML). The precancerous condition is, e.g., myelodysplastic syndromes (MDS, formerly known as preleukemia).

The subject of the present invention includes any human subject who has been diagnosed with, has symptoms of, or is at risk of developing a cancer or a precancerous condition. The subject of the present invention includes any human subject expressing a mutant EZH2. For example, a mutant EZH2 comprises one or more mutations, wherein the mutation is a substitution, a point mutation, a nonsense mutation, a missense mutation, a deletion, or an insertion. A mutant EZH2 of the present invention may comprise a mutation in the substrate pocket domain as defined in SEQ ID NO: 6. A mutant EZH2 may have a substitution at amino acid Y641. Preferably, the mutant EZH2 has one of the following mutations: substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); and a substitution of cysteine (C) for the wild type residue tyrosine (Y) at amino acid position 641 of SEQ ID NO: 1 (Y641C).

Other mutations of EZH2 may include, but are not limited to: a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of serine (S) for the wild type residue asparagine (N) at amino acid position 322 of SEQ ID NO: 3 (N322S), a substitution of glutamine (Q) for the wild type residue arginine (R) at amino acid position 288 of SEQ ID NO: 3 (R288Q), a substitution of isoleucine (I) for the wild type residue threonine (T) at amino acid position 573 of SEQ ID NO: 3 (T573I), a substitution of glutamic acid (E) for the wild type residue aspartic acid (D) at amino acid position 664 of SEQ ID NO: 3 (D664E), a substitution of glutamine (Q) for the wild type residue arginine (R) at amino acid position 458 of SEQ ID NO: 5 (R458Q), a substitution of lysine (K) for the wild type residue glutamic acid (E) at amino acid position 249 of SEQ ID NO: 3 (E249K), a substitution of cysteine (C) for the wild type residue arginine (R) at amino acid position 684 of SEQ ID NO: 3 (R684C), a substitution of histidine (H) for the wild type residue arginine (R) at amino acid position 628 of SEQ ID NO: 11 (R628H), a substitution of histidine (H) for the wild type residue glutamine (Q) at amino acid position 501 of SEQ ID NO: 5 (Q501H), a substitution of asparagine (N) for the wild type residue aspartic acid (D) at amino acid position 192 of SEQ ID NO: 3 (D192N), a substitution of valine (V) for the wild type residue aspartic acid (D) at amino acid position 664 of SEQ ID NO: 3 (D664V), a substitution of leucine (L) for the wild type residue valine (V) at amino acid position 704 of SEQ ID NO: 3 (V704L), a substitution of serine (S) for the wild type residue proline (P) at amino acid position 132 of SEQ ID NO: 3 (P132S), a substitution of lysine (K) for the wild type residue glutamic acid (E) at amino acid position 669 of SEQ ID NO: 11 (E669K), a substitution of threonine (T) for the wild type residue alanine (A) at amino acid position 255 of SEQ ID NO: 3 (A255T), a substitution of valine (V) for the wild type residue glutamic acid (E) at amino acid position 726 of SEQ ID NO: 3 (E726V), a substitution of tyrosine (Y) for the wild type residue cysteine (C) at amino acid position 571 of SEQ ID NO: 3 (C571Y), a substitution of cysteine (C) for the wild type residue phenylalanine (F) at amino acid position 145 of SEQ ID NO: 3 (F145C), a substitution of threonine (T) for the wild type residue asparagine (N) at amino acid position 693 of SEQ ID NO: 3 (N693T), a substitution of serine (S) for the wild type residue phenylalanine (F) at amino acid position 145 of SEQ ID NO: 3 (F145S), a substitution of histidine (H) for the wild type residue glutamine (Q) at amino acid position 109 of SEQ ID NO: 11 (Q109H), a substitution of cysteine (C) for the wild type residue phenylalanine (F) at amino acid position 622 of SEQ ID NO: 11 (F622C), a substitution of arginine (R) for the wild type residue glycine (G) at amino acid position 135 of SEQ ID NO: 3 (G135R), a substitution of glutamine (Q) for the wild type residue arginine (R) at amino acid position 168 of SEQ ID NO: 5 (R168Q), a substitution of arginine (R) for the wild type residue glycine (G) at amino acid position 159 of SEQ ID NO: 3 (G159R), a substitution of cysteine (C) for the wild type residue arginine (R) at amino acid position 310 of SEQ ID NO: 5 (R310C), a substitution of histidine (H) for the wild type residue arginine (R) at amino acid position 561 of SEQ ID NO: 3 (R561H), a substitution of histidine (H) for the wild type residue arginine (R) at amino acid position 634 of SEQ ID NO: 11 (R634H), a substitution of arginine (R) for the wild type residue glycine (G) at amino acid position 660 of SEQ ID NO: 3 (G660R), a substitution of cysteine (C) for the wild type residue tyrosine (Y) at amino acid position 181 of SEQ ID NO: 3 (Y181C), a substitution of arginine (R) for the wild type residue histidine (H) at amino acid position 297 of SEQ ID NO: 3 (H297R), a substitution of serine (S) for the wild type residue cysteine (C) at amino acid position 612 of SEQ ID NO: 11 (C612S), a substitution of tyrosine (Y) for the wild type residue histidine (H) at amino acid position 694 of SEQ ID NO: 3 (H694Y), a substitution of alanine (A) for the wild type residue aspartic acid (D) at amino acid position 664 of SEQ ID NO: 3 (D664A), a substitution of threonine (T) for the wild type residue isoleucine (I) at amino acid position 150 of SEQ ID NO: 3 (I150T), a substitution of arginine (R) for the wild type residue isoleucine (I) at amino acid position 264 of SEQ ID NO: 3 (I264R), a substitution of leucine (L) for the wild type residue proline (P) at amino acid position 636 of SEQ ID NO: 3 (P636L), a substitution of threonine (T) for the wild type residue isoleucine (I) at amino acid position 713 of SEQ ID NO: 3 (I713T), a substitution of proline (P) for the wild type residue glutamine (Q) at amino acid position 501 of SEQ ID NO: 5 (Q501P), a substitution of glutamine (Q) for the wild type residue lysine (K) at amino acid position 243 of SEQ ID NO: 3 (K243Q), a substitution of aspartic acid (D) for the wild type residue glutamic acid (E) at amino acid position 130 of SEQ ID NO: 5 (E130D), a substitution of glycine (G) for the wild type residue arginine (R) at amino acid position 509 of SEQ ID NO: 3 (R509G), a substitution of histidine (H) for the wild type residue arginine (R) at amino acid position 566 of SEQ ID NO: 3 (R566H), a substitution of histidine (H) for the wild type residue aspartic acid (D) at amino acid position 677 of SEQ ID NO: 3 (D677H), a substitution of asparagine (N) for the wild type residue lysine (K) at amino acid position 466 of SEQ ID NO: 5 (K466N), a substitution of histidine (H) for the wild type residue arginine (R) at amino acid position 78 of SEQ ID NO: 3 (R78H), a substitution of methionine (M) for the wild type residue lysine (K) at amino acid position 1 of SEQ ID NO: 6 (K6M), a substitution of leucine (L) for the wild type residue serine (S) at amino acid position 538 of SEQ ID NO: 3 (S538L), a substitution of glutamine (Q) for the wild type residue leucine (L) at amino acid position 149 of SEQ ID NO: 3 (L149Q), a substitution of valine (V) for the wild type residue leucine (L) at amino acid position 252 of SEQ ID NO: 3 (L252V), a substitution of valine (V) for the wild type residue leucine (L) at amino acid position 674 of SEQ ID NO: 3 (L674V), a substitution of valine (V) for the wild type residue alanine (A) at amino acid position 656 of SEQ ID NO: 3 (A656V), a substitution of aspartic acid (D) for the wild type residue alanine (A) at amino acid position 731 of SEQ ID NO: 3 (Y731D), a substitution of threonine (T) for the wild type residue alanine (A) at amino acid position 345 of SEQ ID NO: 3 (A345T), a substitution of aspartic acid (D) for the wild type residue alanine (A) at amino acid position 244 of SEQ ID NO: 3 (Y244D), a substitution of tryptophan (W) for the wild type residue cysteine (C) at amino acid position 576 of SEQ ID NO: 3 (C576W), a substitution of lysine (K) for the wild type residue asparagine (N) at amino acid position 640 of SEQ ID NO: 3 (N640K), a substitution of lysine (K) for the wild type residue asparagine (N) at amino acid position 675 of SEQ ID NO: 3 (N675K), a substitution of tyrosine (Y) for the wild type residue aspartic acid (D) at amino acid position 579 of SEQ ID NO: 11 (D579Y), a substitution of isoleucine (I) for the wild type residue asparagine (N) at amino acid position 693 of SEQ ID NO: 3 (N693I), and a substitution of lysine (K) for the wild type residue asparagine (N) at amino acid position 693 of SEQ ID NO: 3 (N693K).

Other mutations of EZH2 can include: a frameshift at amino acid position 730, 391, 461, 441, 235, 254, 564, 662, 715, 405, 685, 64, 73, 656, 718, 374, 592, 505, 730, or 363 of SEQ ID NO: 3, 5 or 11, or the corresponding nucleotide position of the nucleic acid sequence encoding SEQ ID NO: 3, 5, or 11; a deletion of glutamic acid (E) and leucine (L) at amino acid positions 148 and 149 of SEQ ID NO: 3, 5 or 11, or a nonsense mutation at amino acid position 733, 25, 317, 62, 553, 328, 58, 207, 123, 63, 137, or 60 of SEQ ID NO: 3, 5 or 11.

A subject of the present invention may have resistance to any one or more other therapeutic agents or any of the compounds described herein. For example, the subject may have resistance to EZH inhibitors or prednisone.

The present invention features a method for inhibiting cancer cell proliferation comprising contacting said cancer cells with a composition comprising any compound of Formula (IIa) or pharmaceutically acceptable salt thereof, and one or more additional therapeutic agent. Inhibiting cancer cell proliferation includes delaying cancer cell growth, inducing cell death, reducing cancer cell viability, inhibiting or delaying tumor growth, or reducing tumor size.

The present invention features methods of combination therapy wherein any compound of Formula (IIa), or pharmaceutically acceptable salt thereof, and one or more other therapeutic agents are administered simultaneously or sequentially. For example, any compound of Formula (IIa) or pharmaceutically acceptable salt thereof may be administered prior to administration of one or more other therapeutic agents. For example, any compound of Formula (IIa) or pharmaceutically acceptable salt there or may be administered prior to administration of a composition comprising any compound of Formula (IIa) or pharmaceutically acceptable salt thereof and one or more other therapeutic agents. Concurrent or sequential administration of any compound of Formula (IIa) and/or each therapeutic agent can be effected by any appropriate route including, but not limited to, oral routes, intravenous routes, intramuscular routes, and direct absorption through mucous membrane tissues. The therapeutic agents can be administered by the same route or by different routes.

The methods of combination therapy featured in the present invention may result in a synergistic effect, wherein the effect of a combination of compounds or other therapeutic agents is greater than the sum of the effects resulting from administration of any of the compounds or other therapeutic agents as single agents. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

Compositions of the present invention can be administered at a dosage of 0.01 mg/kg per day to about 1000 mg/kg per day. Any compound of Formula (IIa) or pharmaceutically acceptable salt thereof may be administered at a dosage of 0.01 mg/kg per day to about 1000 mg/kg per day. Any other therapeutic agent may be administered at a dosage of 0.01 mg/kg per day to about 1000 mg/kg per day.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTIONS OF FIGURES

FIG. 1 is a schematic detailing in vitro treatment schedules for determining the effect of combination therapy on cell viability. (A) Administration of Compound 44 prior to administration of Compound 44 and components of CHOP (Cyclophosphamide, Doxorubicin, Vincristine, and Prednisolone). (B) Administration of Compound 44 prior to CHOP components. (C) Administration of components of CHOP prior to administration of Compound 44 and CHOP components. After 4 days, cell viability was determined.

Figure 2:
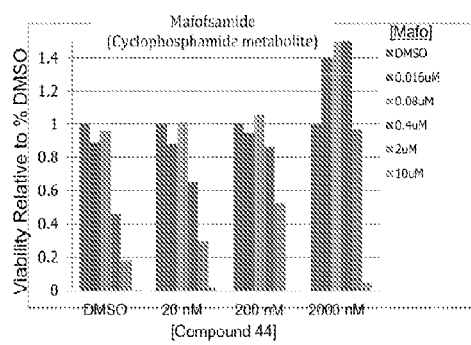
Figure 2:
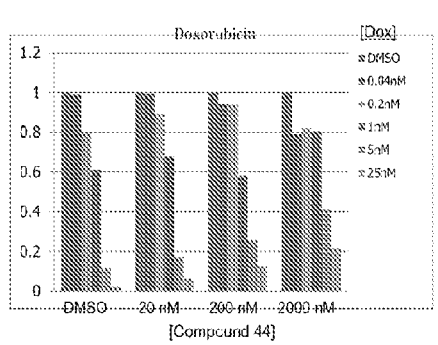
Figure 2:
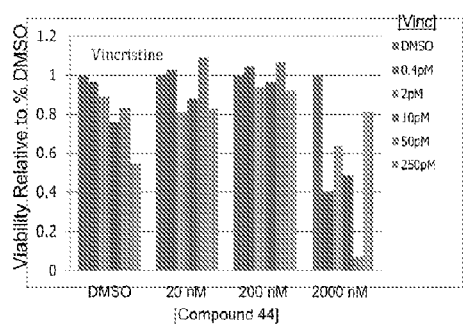
Figure 2:
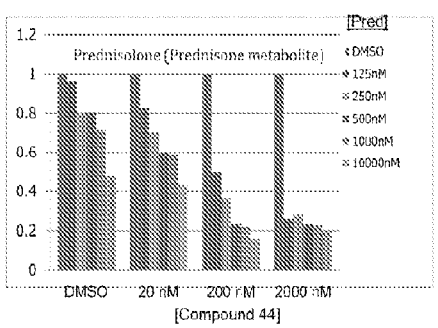

FIG. 2 is four graphs measuring cancer cell viability in vitro after treatment with Compound 44 and CHOP components alone or in combination. WSU-DLCL2 cells were treated as shown in FIG. 1A. Cells were first treated with varying concentrations of Compound 44. After four days, cells were treated with the combination of varying concentrations of Compound 44 and (A) Mafofsamide (Cyclophosphamide metabolite), (B) Doxorubicin, (C) Vincristine, or (D) Prednisolone (Prednisone metabolite). Control cells were treated with DMSO. Cell viability was normalized to the percentage of cell viability in DMSO-treated for each Compound 44 concentration.

Figure 3:
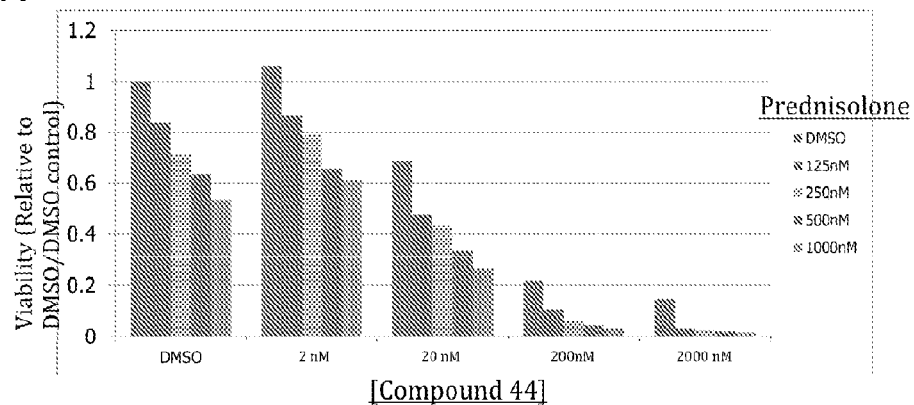
Figure 3:
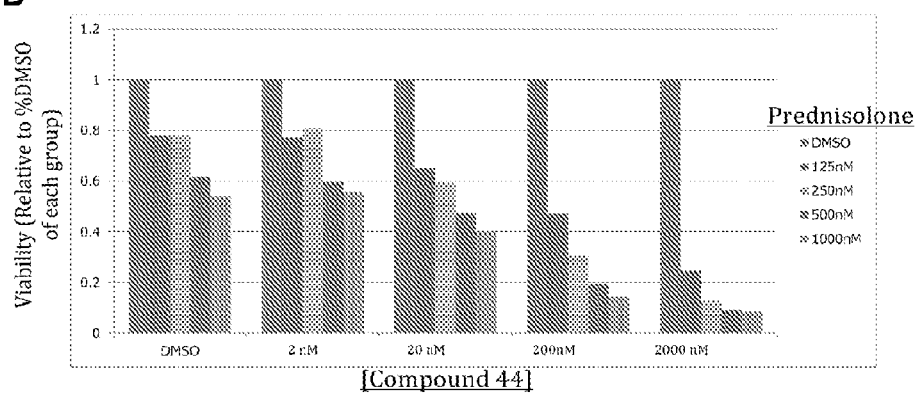
Figure 3:
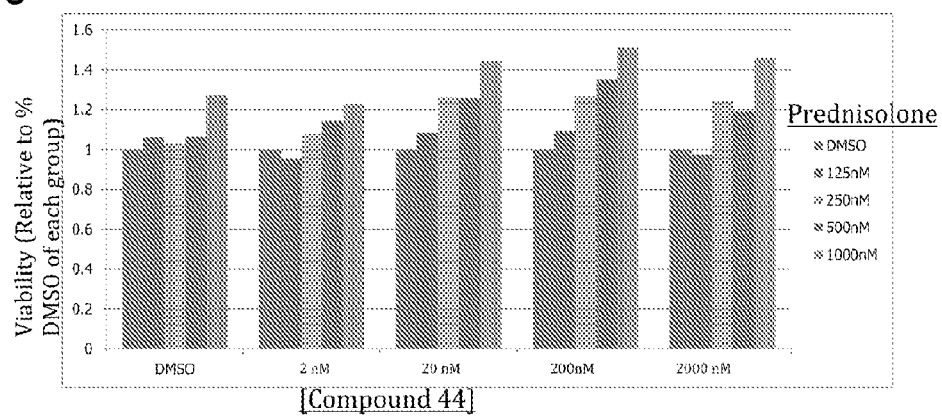

FIG. 3 is three graphs measuring cancer cell viability after various treatment schedules. WSU-DCLC2 cells were treated with increasing concentrations of Prednisolone and Compound 44. Cells were treated with Compound 44 and Prednisolone according to the treatment schedule in (A) FIG. 1A, (B) FIG. 1B, or (C) FIG. 1C. Cell viability was normalized to the DMSO/DMSO-treated sample.

Figure 4:
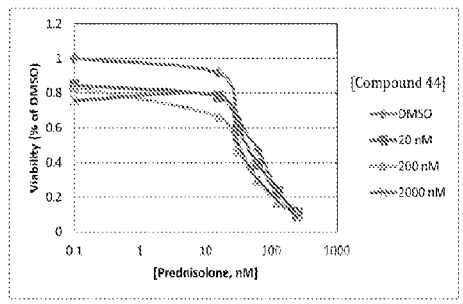
Figure 4:
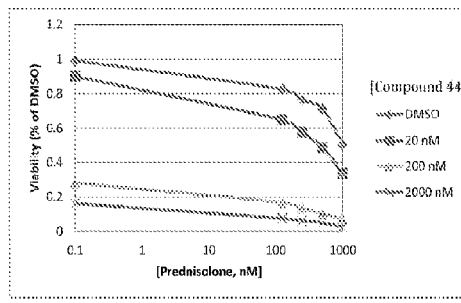
Figure 4:
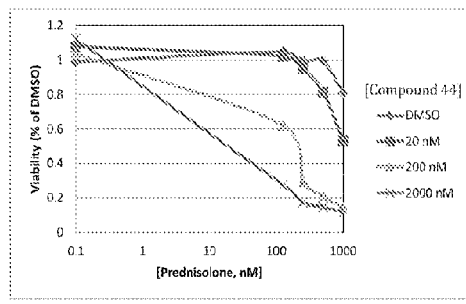

FIG. 4 is three graphs measuring cancer cell viability after treatment with Prednisolone and Compound 44 in cell lines with different EZH2 mutations. Cells were treated as depicted in FIG. 1A and with increasing concentrations of Prednisolone and Compound 44. Cell viability was normalized to the DMSO/DMSO-treated sample. (A) WSU-DLCL2 cells express the Y641F mutation and are sensitive to EZH2 inhibitors. (B) RL cells express the Y641N mutation are resistant to EZH2 inhibitors and Prednisolone. (C) OCI-LY19 cells are wild-type at Y641 and show sensitivity to Presnisolone, but do not show sensitivity to Compound 44 or increased sensitivity to combinations of Compound 44 plus Prednisolone.

Figure 5:
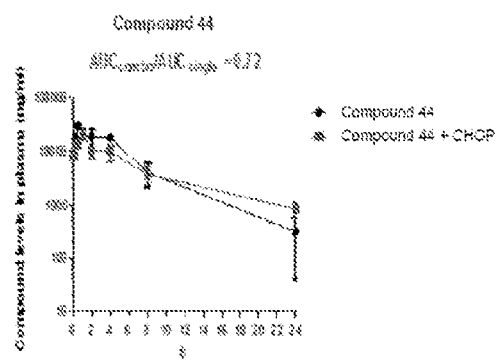
Figure 5:
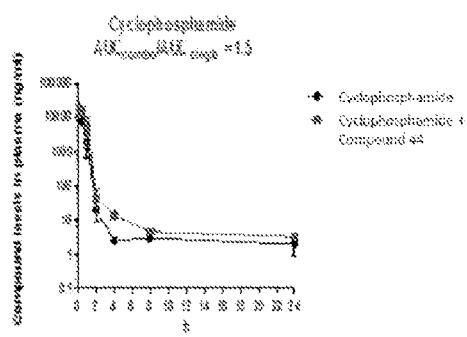
Figure 5:
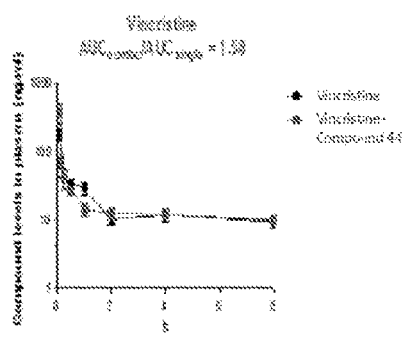
Figure 5:
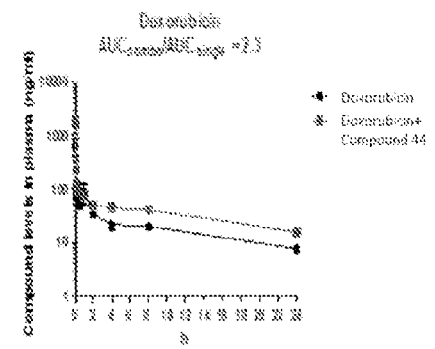
Figure 5:
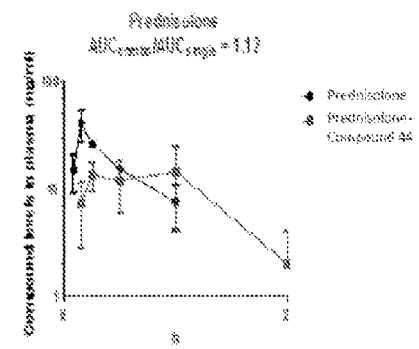

FIG. 5 is five graphs showing a panel of pharmacokinetic profiles for co-administration of Compound 44 and CHOP components in vivo. BALB/c mice were administered a single oral administration of Compound 44 and CHOP components. The concentration of Compound 44 (ng/mL) in the plasma was measured at various timepoints 0-24 hours after administration. Cyclophoshamide was administered by intraperitoneal injection at 30 mg/kg. Vincristine was administered by intravenous injection at 0.375 mg/kg. Doxorubicin was administered by intravenous injection at 2.475 mg/kg. Prednisolone was administered by oral administration at 0.15 mg/kg. Compound 44 was administered by oral administration at 225 mg/kg.

Figure 6:
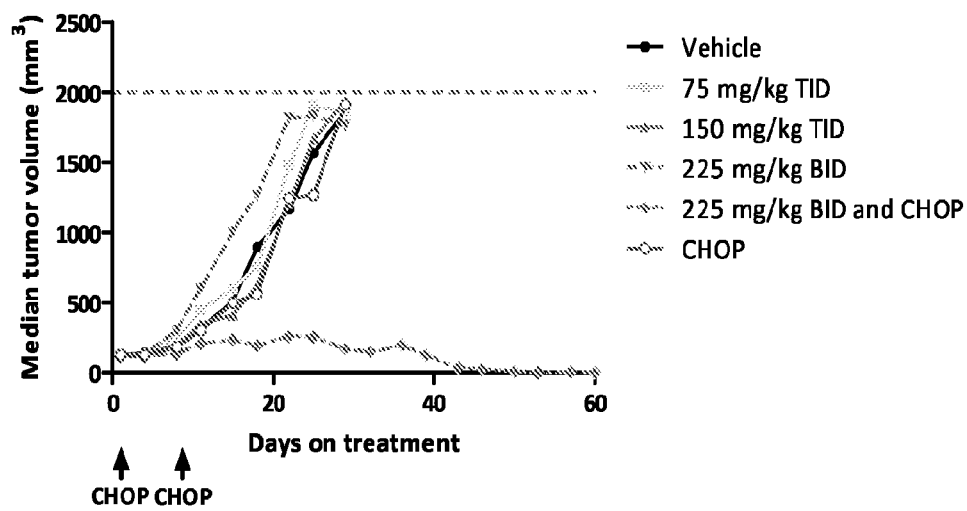
Figure 6:
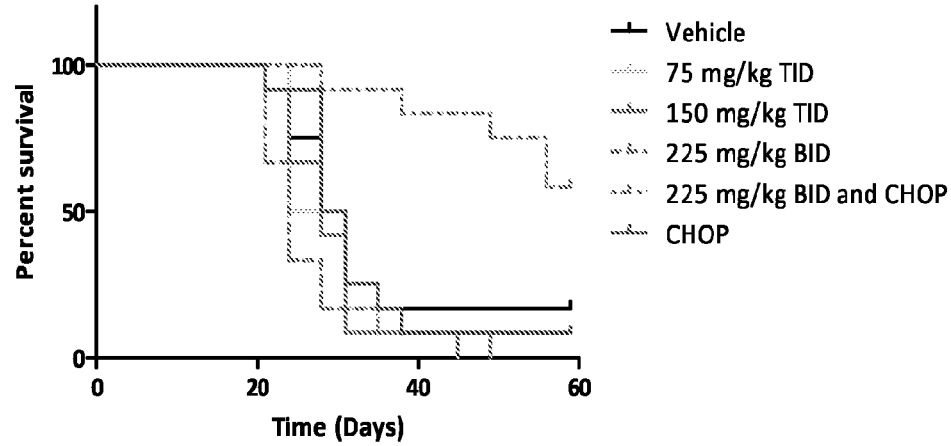

FIG. 6 is two graphs demonstrating the effect of Compound 44 and CHOP administration in SUDHL6 xenograft model on tumor growth and survival. Athymic nude mice were subcutaneously injected with 1×10⁷ SUDHL6 human lymphoma cells. After tumors reached a size of app. 120 mm³ Compound 44 was administered over 28 days at the indicated dosages either three times a day (TID) or twice a day (BID). CHOP (Cyclophosphamide, Vincristine, Doxorubicin, and Prednisone) was administered at day 1 and 8 to mice receiving 225 mg/kg twice per day (225 mg/kg BID and CHOP). Control mice did not receive any Compound 44 (vehicle) or CHOP only (CHOP). Tumor volume was measured twice a week. Animals were euthanized when tumor volume reached 2000 mm³ or 60 days after the first dose. (A) For tumor growth delay analysis, median tumor volume was calculated for each treatment group by measuring the tumors twice a week for 60 days or until the tumor reached 2000 mm³. (B) Kaplan-meier curve depicts the survival rate of the mice.

Figure 7:
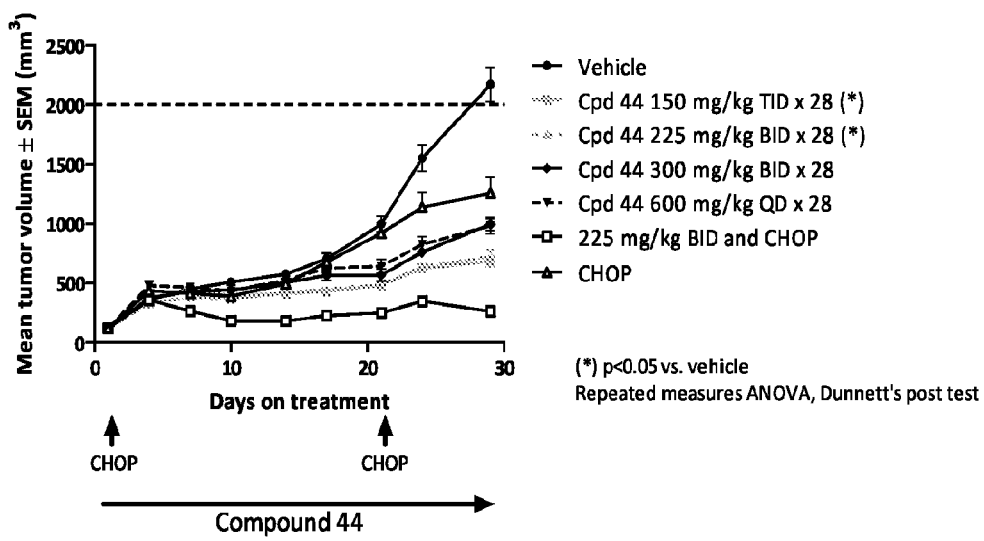
Figure 7:
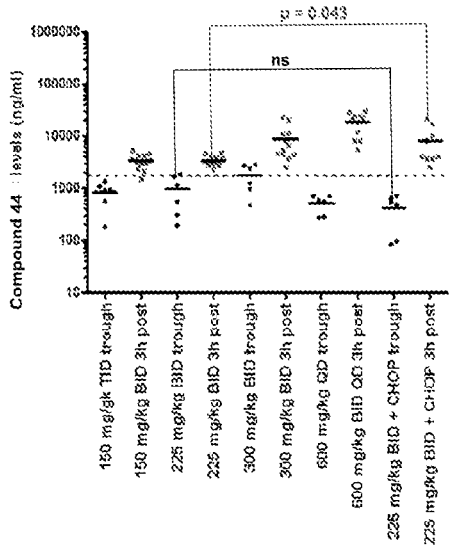
Figure 7:
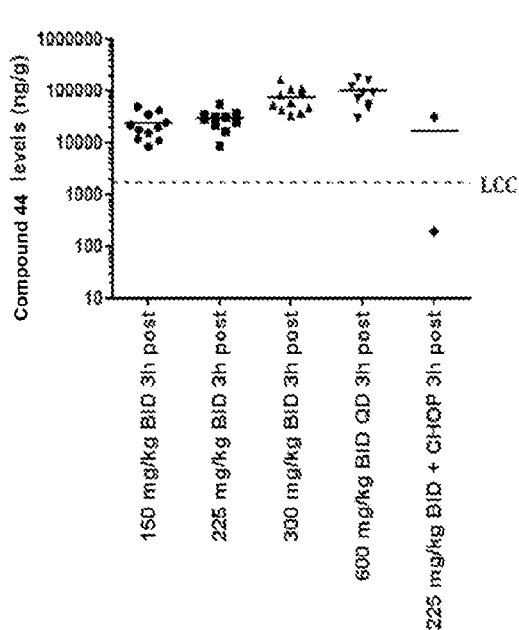

FIG. 7 is three graphs demonstrating the effect of Compound 44 and CHOP administration in WSU-DLCL2 xenograft model on tumor growth and survival. SCID mice were subcutaneously injected with 1×10⁷ WSU-DLCL2 human lymphoma cells. After tumors reached a size of app. 120 mm³ Compound 44 was administered over 28 days at the indicated dosages at three times a day (TID), twice a day (BID) or once a day (QD). CHOP (Cyclophosphamide, Vincristine, Doxorubicin, and Prednisone) was administered at day 1 and 22 to mice receiving 225 mg/kg twice a day (225 mg/kg BID and CHOP). Control mice either did not receive any Compound 44 (vehicle) or received CHOP only (CHOP). Tumor volume was measured twice a week. Animals were euthanized 28 days after first dose. (A) Treatment efficacy was determined by measuring mean tumor volume over the course of treatment. (B) Concentration (ng/mL) of Compound 44 was measured in plasma from mice on day 28 at before administration (trough) and three hours post-administration (post). (C) Concentration (ng/g) of Compound 44 was measured from tumor tissue from mice on day 28 three hours post-administration.

Figure 8:
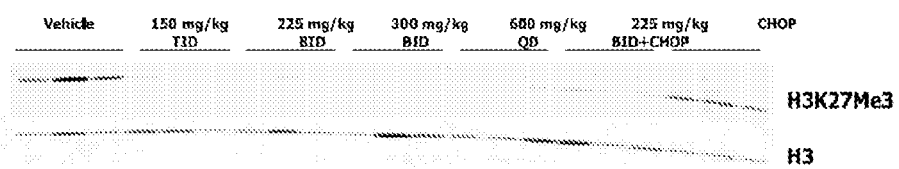
Figure 8:
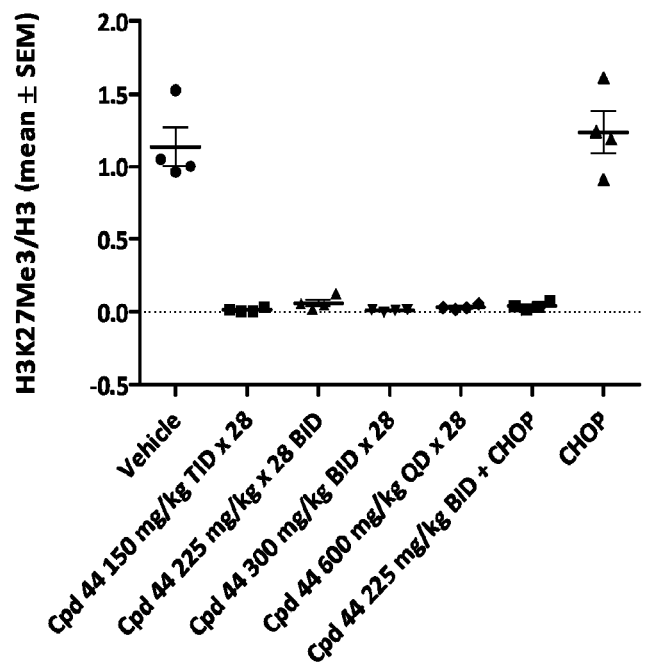

FIG. 8 is a western blot analysis and a graph showing the histone methylation status from tumor samples from the WSU-DLCL2 xenograft model. Tumors were harvested 28 days after injection and histones were extracted. (A) A Western Blot was probed with antibodies specifically recognizing tri-methylated Lysine 27 of histone H3 (H3K27me3) and total histone H3 proteins. (B) Methylation status of tumors was determined by ELISA. H3K27 tri-methylation was detected and normalized to total histone H3 levels.

Figure 9:
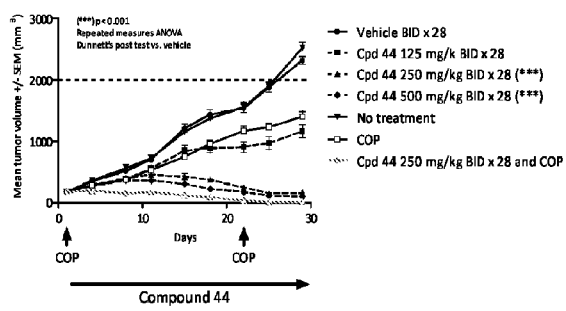
Figure 9:
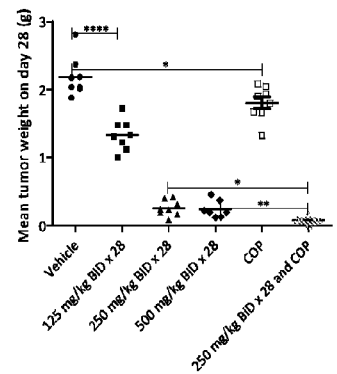
Figure 9:
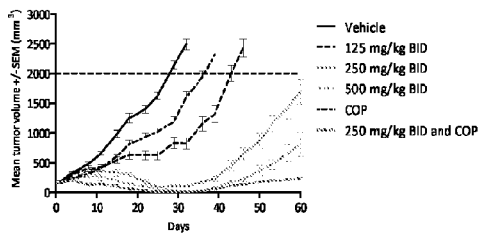
Figure 9:
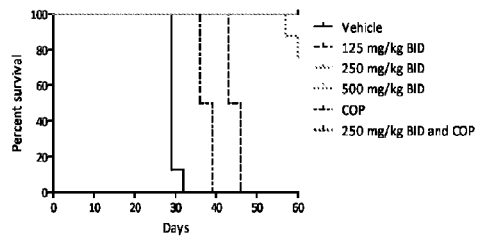

FIG. 9 is four graphs demonstrating the effect of Compound 44 and COP administration in a SUDHL10 xenograft model on tumor growth and survival. SCID mice were subcutaneously injected with 1×10$^7$ SUDHL10 human lymphoma cells. After tumors reached a size of app. 120 mm$^3$ Compound 44 was administered over 28 days at the indicated dosages twice a day (BID). COP (Cyclophosphamide, Vincristine, and Prednisone) was administered at day 1 and 22 to mice receiving 250 mg/kg twice a day (250 mg/kg BID and COP). Control mice did not receive any Compound 44 (vehicle) or COP only (COP). Tumor volume was measured twice a week. (A) Treatment efficacy was determined by measuring mean tumor volume over the course of treatment. (B) Mean tumor weight was determined after mice were euthanized on day 28 after first dosing. (C) For tumor growth delay analysis, mean tumor volume and SEM was calculated for each treatment group by measuring the tumors twice a week for 60 days or until the tumor reached 2000 mm$^3$. (D) Kaplan-Meier curve depicts the survival rate of the treated mice.

Figure 10:
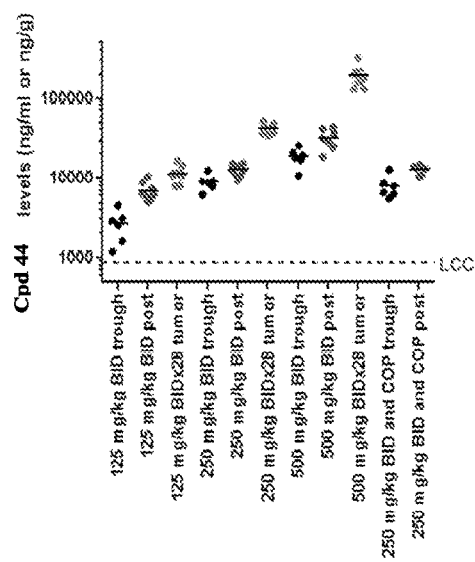
Figure 10:
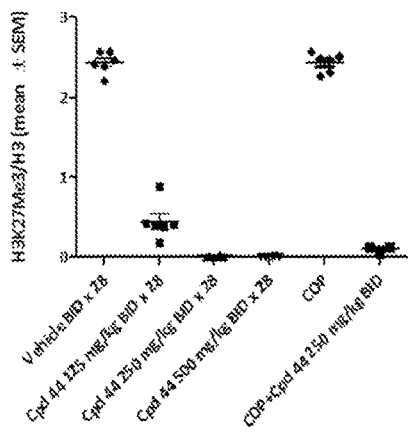
Figure 10:
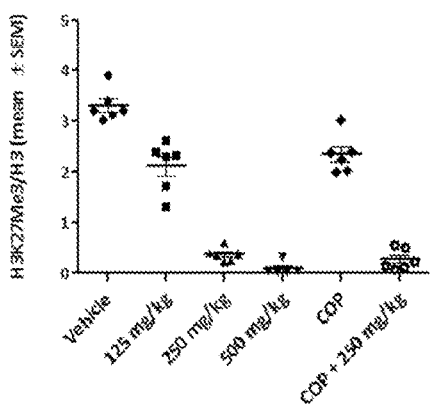
Figure 10:
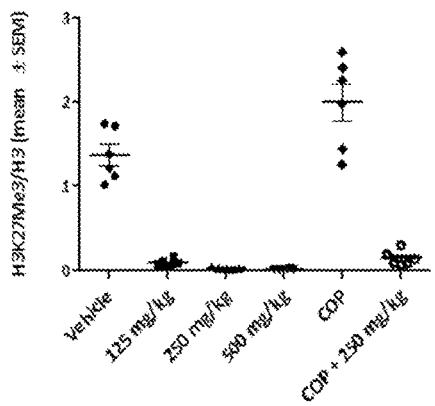

FIG. 10 is four graphs showing the pharmacokinetic and pharmacodynamic profiles after COP and Compound 44 administration in the SUDHL10 xenograft model. Tumor-bearing mice were euthanized after 28 days of treatment and tissues were harvested. (A) Concentration (ng/mL) of Compound 44 was measured in plasma from mice on day 28 before administration (trough) and post-administration (post) by LC-MS/MS. Methylation status of various tissues from tumor-bearing mice were determined by ELISA: (B) tumor, (C) spleen, and (D) bone marrow. H3K27 tri-methylation was detected and normalized to total histone H3 levels.

Figure 11:
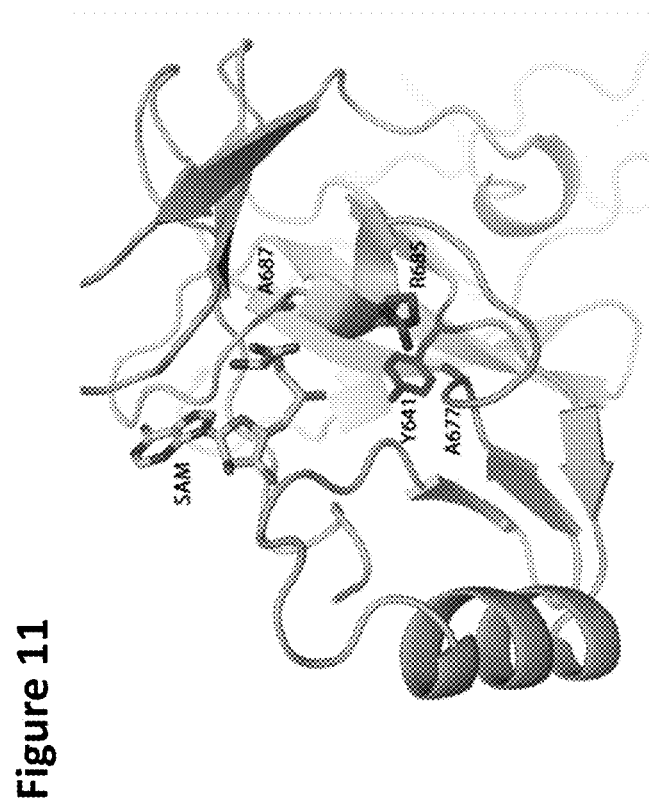

FIG. 11 is a structure model of partial EZH2 protein based on the A chain of nuclear receptor binding SET domain protein 1 (NSD1) is provided below. This model corresponds to amino acid residues 533-732 of EZH2 sequence of SEQ ID NO: 1.

DETAILED DESCRIPTION OF THE INVENTION

The present invention is based upon the discovery that EZH2 histone methyltransferase inhibitors and other anti-cancer agents can be used in combination to treat certain tumors with superior results than those achieved by treating tumors with FZH2 histone methyltransferase inhibitors and the anti-cancer agents alone. Accordingly, the present invention provides a composition comprising an EZH2 histone methyltransferase inhibitor and one or more other therapeutic agents, and methods for their use to treat diseases the course of which can be influenced by modulating the methylation status of histones or other proteins, e.g., cancer. In a certain embodiment, the present invention features a composition comprising a compound of Formula (IIa) and prednisone. The present invention also includes methods for combination therapies comprising EZH2 histone methyltransferase inhibitor and one or more therapeutic agents, such as a compound of Formula (IIa) and prednisone, to treat cancer, e.g., follicular lymphoma (FL) and diffuse cell large B-cell lymphoma (DCLBL). Specifically, the methods of the present invention are useful for treating or preventing cancer or inhibiting cancer cell proliferation.

EZH2 is a histone methyltransferase that is the catalytic subunit of the PRC2 complex which catalyzes the mono-through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) Nature 419(6907):624-9 Kleer et al. (2003) *Proc Natl Acad Sci USA* 100(20):11606-11.

An aspect of the present invention relates to methods for treating or alleviating a symptom of cancer or precancerous condition in a subject by administering to a subject expressing a mutant EZH2 a therapeutically effective amount of an EZH2 inhibitor and one or more other therapeutic agents. The mutant EZH2 of the present invention refers to a mutant EZH2 polypeptide or a nucleic acid sequence encoding a mutant EZH2 polypeptide. In certain embodiments the mutant EZH2 comprises one or more mutations in its substrate pocket domain as defined in SEQ ID NO: 6. For example, the mutation may be a substitution, a point mutation, a nonsense mutation, a missense mutation, a deletion, or an insertion.

Human EZH2 nucleic acids and polypeptides have previously been described. See, e.g., Chen et al. (1996) *Genomics* 38:30-7 [746 amino acids]; Swiss-Prot Accession No. Q15910 [746 amino acids]; GenBank Accession Nos. NM_004456 and NP_004447 (isoform a [751 amino acids]); and GenBank Accession Nos. NM_152998 and NP_694543 (isoform b [707 amino acids]), each of which is incorporated herein by reference in its entirety.

```
Amino acid sequence of human EZH2 (Swiss-Prot Accession No. Q15910)
                                                            (SEQ ID NO: 1)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL
```

-continued

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEYCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP

Nucleotide sequence of human EZH2, transcript variant 1 (GenBank Accession No. NM_004456)

(SEQ ID NO: 2)

ggcggcgcttgattgggctgggggggccaaataaaagcgatggcgattgggctgccgcgt ttggcgctcggtccggtcgcgtccgacacccggtgggactcagaaggcagtggagccccg gcggcggcggcggcggcgcgcgggggcgacgcgcgggaacaacgcgagtcggcgcgcggg acgaagaataatcatgggccagactgggaagaaatctgagaagggaccagtttgttggcg gaagcgtgtaaaatcagagtacatgcgactgagacagctcaagaggttcagacgagctga tgaagtaaagagtatgtttagttccaatcgtcagaaaattttggaaagaacggaaatctt aaaccaagaatggaaacagcgaaggatacagcctgtgcacatcctgacttctgtgagctc attgcgcgggactagggagtgttcggtgaccagtgacttggattttccaacacaagtcat cccattaaagactctgaatgcagttgcttcagtacccataatgtattcttggtctcccct acagcagaattttatggtggaagatgaaactgttttacataacattccttatatgggaga tgaagttttagatcaggatggtactttcattgaagaactaataaaaaattatgatgggaa agtacacggggatagagaatgtgggtttataaatgatgaattttttgtggagttggtgaa tgcccttggtcaatataatgatgatgacgatgatgatgatggagacgatcctgaagaaag agaagaaaagcagaaagatctggaggatcaccgagatgataaagaaagccgcccacctcg gaaatttccttctgataaaatttttgaagccatttcctcaatgtttccagataagggcac agcagaagaactaaaggaaaaatataaagaactcaccgaacagcagctcccaggcgcact tcctcctgaatgtaccccaacatagatggaccaaatgctaaatctgttcagagagagca aagcttacactcctttcatcgcttttctgtaggcgatgttttaaatatgactgcttcct acatcgtaagtgcaattattcttttcatgcaacacccaacacttataagcggaagaacac agaaacagctctagacaacaaaccttgtggaccacagtgttaccagcatttggagggagc aaaggagtttgctgctgctctcaccgctgagcggataaagaccccaccaaaacgtccagg aggccgcagaagaggacggcttcccaataacagtagcaggcccagcaccccaccattaa tgtgctggaatcaaaggatacagacagtgatagggaagcagggactgaaacgggggaga gaacaatgataaagaagaagaagagaagaaagatgaaacttcgagctcctctgaagcaaa ttctcggtgtcaaacaccaataaagatgaagccaaatattgaacctcctgagaatgtgga gtggagtggtgctgaagcctcaatgtttagagtcctcattggcacttactatgacaattt ctgtgccattgctaggttaattgggaccaaaacatgtagacaggtgtatgagtttagagt caaagaatctagcatcatagctccagctcccgctgaggatgtggatactcctccaaggaa aaagaagaggaaacaccggttgtgggctgcacactgcagaaagatacagctgaaaagga cggctcctctaaccatgtttacaactatcaaccctgtgatcatccacggcagccttgtga

```
cagttcgtgcccttgtgtgatagcacaaaattttgtgaaaagttttgtcaatgtagttc agagtgtcaaaaccgctttccgggatgccgctgcaaagcacagtgcaacaccaagcagtg cccgtgctacctggctgtccgagagtgtgaccctgacctctgtcttacttgtggagccgc tgaccattgggacagtaaaaatgtgtcctgcaagaactgcagtattcagcggggctccaa aaagcatctattgctggcaccatctgacgtggcaggctgggggattttttatcaaagatcc tgtgcagaaaaatgaattcatctcagaatactgtggagagattatttctcaagatgaagc tgacagaagagggaaagtgtatgataaatacatgtgcagctttctgttcaacttgaacaa tgattttgtggtggatgcaacccgcaagggtaacaaaattcgttttgcaaatcattcggt aaatccaaactgctatgcaaaagttatgatggttaacggtgatcacaggataggtatttt tgccaagagagccatccagactggcgaagagctgttttttgattacagatacagccaggc tgatgccctgaagtatgtcggcatcgaaagagaaatggaaatcccttgacatctgctacc tcctccccctcctctgaaacagctgccttagcttcaggaacctcgagtactgtgggcaa tttagaaaagaacatgcagtttgaaattctgaatttgcaaagtactgtaagaataattt atagtaatgagtttaaaaatcaacttttttattgccttctcaccagctgcaaagtgtttg taccagtgaatttttgcaataatgcagtatggtacattttttcaactttgaataaagaata cttgaacttgtccttgttgaatc
```

Full amino acid of EZH2, isoform a (GenBank Accession No. NP_004447)

(SEQ ID NO: 3)

```
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHRKC

NYSFHATPNTYKRKNTETALDNKPCGPQCYQHLEGAKEFAAALTAERIKTPPKRPGGRRR

GRLPNNSSRPSTPTINVLESKDTDSDREAGTETGGENNDKEEEEKKDETSSSSEANSRCQ

TPIKMKPNIEPPENVEWSGAEASMFRVLIGTYYDNFCAIARLIGTKTCRQVYEFRVKESS

IIAPAPAEDVDTPPRKKKRKHRLWAAHCRKIQLKKDGSSNHVYNYQPCDHPRQPCDSSCP

CVIAQNFCEKFCQCSSECQNRFPGCRCKAQCNTKQCPCYLAVRECDPDLCLTCGAADHWD

SKNVSCKNCSIQRGSKKHLLLAPSDVAGWGIFIKDPVQKNEFISEYCGEIISQDEADRRG

KVYDKYMCSFLFNLNNDFVVDATRKGNKIRFANHSVNPNCYAKVMMVNGDHRIGIFAKRA

IQTGEELFFDYRYSQADALKYVGIEREMEIP
```

Nucleotide sequence of human EZH2, transcript variant 2 (GenBank Accession No. NM_152998)

(SEQ ID NO: 4)

```
ggcggcgcttgattgggctgggggggccaaataaaagcgatggcgattgggctgccgcgt ttggcgctcggtccggtcgcgtccgacacccggtgggactcagaaggcagtggagccccg gcggcggcggcggcggcgcgcggggggcgacgcgcgggaacaacgcgagtcggcgcgcggg acgaagaataatcatgggccagactgggaagaaatctgagaagggaccagtttgttggcg gaagcgtgtaaaatcagagtacatgcgactgagacagctcaagaggttcagacgagctga tgaagtaaagagtatgtttagttccaatcgtcagaaaattttggaaagaacggaaatctt aaaccaagaatggaaacagcgaaggatacagcctgtgcacatcctgacttctgtgagctc attgcgcgggactaggaggtggaagatgaaactgttttacataacattccttatatggg agatgaagtttttagatcaggatggtactttcattgaagaactaataaaaaaattatgatgg
```

-continued

```
gaaagtacacggggatagagaatgtgggtttataaatgatgaattttgtggagttggt gaatgcccttggtcaatataatgatgatgacgatgatgatgatggagacgatcctgaaga aagagaagaaaagcagaaagatctggaggatcaccgagatgataaagaaagccgcccacc tcggaaatttccttctgataaaattttgaagccatttcctcaatgtttccagataaggg cacagcagaagaactaaaggaaaaatataaagaactcaccgaacagcagctcccaggcgc acttcctcctgaatgtaccccaacatagatggaccaaatgctaaatctgttcagagaga gcaaagcttacactcctttcatacgcttttctgtaggcgatgttttaaatatgactgctt cctacatccttttcatgcaacacccaacacttataagcggaagaacacagaaacagctct agacaacaaaccttgtggaccacagtgttaccagcatttggagggagcaaaggagtttgc tgctgctctcaccgctgagcggataaagaccccaccaaaacgtccaggaggccgcagaag aggacggcttcccaataacagtagcaggcccagcaccccaccattaatgtgctggaatc aaaggatacagacagtgataggaagcagggactgaaacgggggagagaacaatgataa agaagaagaagagaagaaagatgaaacttcgagctcctctgaagcaaattctcggtgtca aacaccaataaagatgaagccaaatattgaacctcctgagaatgtggagtggagtggtgc tgaagcctcaatgtttagagtcctcattggcacttactatgacaatttctgtgccattgc taggttaattgggaccaaaacatgtagacaggtgtatgagtttagagtcaaagaatctag catcatagctccagctcccgctgaggatgtggatactcctccaaggaaaaagaagaggaa acaccggttgtgggctgcacactgcagaaagatacagctgaaaaaggacggctcctctaa ccatgtttacaactatcaaccctgtgatcatccacggcagccttgtgacagttcgtgccc ttgtgtgatagcacaaaatttttgtgaaaagttttgtcaatgtagttcagagtgtcaaaa ccgctttccgggatgccgctgcaaagcacagtgcaacaccaagcagtgcccgtgctacct ggctgtccgagagtgtgaccctgacctctgtcttacttgtggagccgctgaccattggga cagtaaaaatgtgtcctgcaagaactgcagtattcagcggggctccaaaaagcatctatt gctggcaccatctgacgtggcaggctgggggatttttatcaaagatcctgtgcagaaaaa tgaattcatctcagaatactgtggagagattatttctcaagatgaagctgacagaagagg gaaagtgtatgataaatacatgtgcagctttctgttcaacttgaacaatgattttgtggt ggatgcaacccgcaagggtaacaaaattcgttttgcaaatcattcggtaaatccaaactg ctatgcaaaagttatgatggttaacggtgatcacaggataggtatttttgccaagagagc catccagactggcgaagagctgttttttgattacagatacagccaggctgatgccctgaa gtatgtcggcatcgaaagagaaatggaaatcccttgacatctgctacctcctcccccctc ctctgaaacagctgccttagcttcaggaacctcgagtactgtgggcaatttagaaaaga acatgcagtttgaaattctgaatttgcaaagtactgtaagaataatttatagtaatgagt ttaaaaatcaacttttttattgccttctcaccagctgcaaagtgttttgtaccagtgaatt tttgcaataatgcagtatggtacattttcaactttgaataaagaatacttgaacttgtc cttgttgaatc
```

Full amino acid of EZH2, isoform b (GenBank Accession No. NP_694543)

(SEQ ID NO: 5)

MGQTGKKSEKGPVCWRKRVKSEYMRLRQLKRFRRADEVKSMFSSNRQKIL

ERTEILNQEWKQRRIQPVHILTSVSSLRGTREVEDETVLHNIPYMGDEVL

DQDGTFIEELIKNYDGKVHGDRECGFINDEIFVELVNALGQYNDDDDDDD

GDDPEEREEKQKDLEDHRDDKESRPPRKFPSDKIFEAISSMFPDKGTAEE

-continued
```
LKEKYKELTEQQLPGALPPECTPNIDGPNAKSVQREQSLHSFHTLFCRRC

FKYDCFLHPFHATPNTYKRKNTETALDNKPCGPQCYQHLEGAKEFAAALT

AERIKTPPKRPGGRRRGRLPNNSSRPSTPTINVLESKDTDSDREAGTETG

GENNDKEEEEKKDETSSSSEANSRCQTPIKMKPNIEPPENVEWSGAEASM

FRVLIGTYYDNFCAIARLIGTKTCRQVYEFRVKESSIIAPAPAEDVDTPP

RKKKRKHRLWAAHCRKIQLKKDGSSNHVYNYQPCDHPRQPCDSSCPCVIA

QNFCEKFCQCSSECQNRFPGCRCKAQCNTKQCPCYLAVRECDPDLCLTCG

AADHWDSKNVSCKNCSIQRGSKKHLLLAPSDVAGWGIFIKDPVQKNEFIS

EYCGEIISQDEADRRGKVYDKYMCSFLFNLNNDFVVDATRKGNKIRFANH

SVNPNCYAKVMMVNGDHRIGIFAKRAIQTGEELFFDYRYSQADALKYVGI

EREMEIP
```

Full amino acid of EZH2, isoform e (GenBank Accession No. NP_001190178.1)
(SEQ ID NO: 11)
```
MGQTGKKSEKGPVCWRKRVKSEYMRLRQLKRFRRADEVKSMFSSNRQKILERTEILNQEWKQRRIQPVHI

LTSCSVTSDLDFPTQVIPLKTLNAVASVPIMYSWSPLQQNFMVEDETVLHNIPYMGDEVLDQDGTFIEEL

IKNYDGKVHGDRECGFINDEIFVELVNALGQYNDDDDDDGDDPEEREEKQKDLEDHRDDKESRPPRKFP

SDKIFEAISSMFPDKGTAEELKEKYKELTEQQLPGALPPECTPNIDGPNAKSVQREQSLHSFHTLFCRRC

FKYDCFLHPFHATPNTYKRKNTETALDNKPCGPQCYQHLEGAKEFAAALTAERIKTPPKRPGGRRRGRLP

NNSSRPSTPTINVLESKDTDSDREAGTETGGENNDKEEEEKKDETSSSSEANSRCQTPIKMKPNIEPPEN

VEWSGAEASMFRVLIGTYYDNFCAIARLIGTKTCRQVYEFRVKESSIIAPAPAEDVDTPPRKKKRKHRLW

AAHCRKIQLKKGQNRFPGCRCKAQCNTKQCPCYLAVRECDPDLCLTCGAADHWDSKNVSCKNCSIQRGSK

KHLLLAPSDVAGWGIFIKDPVQKNEFISEYCGEIISQDEADRRGKVYDKYMCSFLFNLNNDFVVDATRKG

NKIRFANHSVNPNCYAKVMMVNGDHRIGIFAKRAIQTGEELFFDYRYSQADALKYVGIEREMEIP
```

*Homo sapiens* enhancer of zeste homolog 2 (*Drosophila*) (EZH2), transcript variant 5, nucleotide sequence (GenBank Accession No. NM_001203249.1)
(SEQ ID NO: 12)
```
GACGACGTTCGCGGCGGGGAACTCGGAGTAGCTTCGCCTCTGACGTTTCCCCACGACGCACCCCGAAATC

CCCCTGAGCTCCGGCGGTCGCGGGCTGCCCTCGCCGCCTGGTCTGGCTTTATGCTAAGTTTGAGGGAAGA

GTCGAGCTGCTCTGCTCTCTATTGATTGTGTTTCTGGAGGGCGTCCTGTTGAATTCCCACTTCATTGTGT

ACATCCCCTTCCGTTCCCCCCAAAAATCTGTGCCACAGGGTTACTTTTTGAAAGCGGGAGGAATCGAGAA

GCACGATCTTTTGGAAAACTTGGTGAACGCCTAAATAATCATGGGCCAGACTGGGAAGAAATCTGAGAAG

GGACCAGTTTGTTGGCGGAAGCGTGTAAAATCAGAGTACATGCGACTGAGACAGCTCAAGAGGTTCAGAC

GAGCTGATGAAGTAAAGAGTATGTTTAGTTCCAATCGTCAGAAAATTTTGGAAAGAACGGAAATCTTAAA

CCAAGAATGGAAACAGCGAAGGATACAGCCTGTGCACATCCTGACTTCTTGTTCGGTGACCAGTGACTTG

GATTTTCCAACACAAGTCATCCCATTAAAGACTCTGAATGCAGTTGCTTCAGTACCCATAATGTATTCTT

GGTCTCCCCTACAGCAGAATTTTATGGTGGAAGATGAAACTGTTTTACATAACATTCCTTATATGGGAGA

TGAAGTTTTAGATCAGGATGGTACTTTCATTGAAGAACTAATAAAAAATTATGATGGGAAAGTACACGGG

GATAGAGAATGTGGGTTTATAAATGATGAATTTTTGTGGAGTTGGTGAATGCCCTTGGTCAATATAATG

ATGATGACGATGATGATGATGGAGACGATCCTGAAGAAAGAGAAGAAAAGCAGAAAGATCTGGAGGATCA

CCGAGATGATAAAGAAAGCCGCCCACCTCGGAAATTTCCTTCTGATAAAATTTTTGAAGCCATTTCCTCA

ATGTTTCCAGATAAGGGCACAGCAGAAGAACTAAAGGAAAAATATAAAGAACTCACCGAACAGCAGCTCC

CAGGCGCACTTCCTCCTGAATGTACCCCCAACATAGATGGACCAAATGCTAAATCTGTTCAGAGAGAGCA

AAGCTTACACTCCTTTCATACGCTTTTCTGTAGGCGATGTTTTAAATATGACTGCTTCCTACATCCTTTT
```

-continued

```
CATGCAACACCCAACACTTATAAGCGGAAGAACACAGAAACAGCTCTAGACAACAAACCTTGTGGACCAC

AGTGTTACCAGCATTTGGAGGGAGCAAAGGAGTTTGCTGCTGCTCTCACCGCTGAGCGGATAAAGACCCC

ACCAAAACGTCCAGGAGGCCGCAGAAGAGGACGGCTTCCCAATAACAGTAGCAGGCCCAGCACCCCCACC

ATTAATGTGCTGGAATCAAAGGATACAGACAGTGATAGGGAAGCAGGGACTGAAACGGGGGGAGAGAACA

ATGATAAAGAAGAAGAAGAGAAGAAAGATGAAACTTCGAGCTCCTCTGAAGCAAATTCTCGGTGTCAAAC

ACCAATAAAGATGAAGCCAAATATTGAACCTCCTGAGAATGTGGAGTGGAGTGGTGCTGAAGCCTCAATG

TTTAGAGTCCTCATTGGCACTTACTATGACAATTTCTGTGCCATTGCTAGGTTAATTGGGACCAAAACAT

GTAGACAGGTGTATGAGTTTAGAGTCAAAGAATCTAGCATCATAGCTCCAGCTCCCGCTGAGGATGTGGA

TACTCCTCCAAGGAAAAAGAAGAGGAAACACCGGTTGTGGGCTGCACACTGCAGAAAGATACAGCTGAAA

AAGGGTCAAAACCGCTTTCCGGGATGCCGCTGCAAAGCACAGTGCAACACCAAGCAGTGCCCGTGCTACC

TGGCTGTCCGAGAGTGTGACCCTGACCTCTGTCTTACTTGTGGAGCCGCTGACCATTGGGACAGTAAAA

TGTGTCCTGCAAGAACTGCAGTATTCAGCGGGCTCCAAAAAGCATCTATTGCTGGCACCATCTGACGTG

GCAGGCTGGGGATTTTTATCAAAGATCCTGTGCAGAAAAATGAATTCATCTCAGAATACTGTGGAGAGA

TTATTTCTCAAGATGAAGCTGACAGAAGAGGGAAAGTGTATGATAAATACATGTGCAGCTTTCTGTTCAA

CTTGAACAATGATTTTGTGGTGGATGCAACCCGCAAGGGTAACAAAATTCGTTTTGCAAATCATTCGGTA

AATCCAAACTGCTATGCAAAAGTTATGATGGTTAACGGTGATCACAGGATAGGTATTTTTGCCAAGAGAG

CCATCCAGACTGGCGAAGAGCTGTTTTTTGATTACAGATACAGCCAGGCTGATGCCCTGAAGTATGTCGG

CATCGAAAGAGAAATGGAAATCCCTTGACATCTGCTACCTCCTCCCCCCTCCTCTGAAACAGCTGCCTTA

GCTTCAGGAACCTCGAGTACTGTGGGCAATTTAGAAAAAGAACATGCAGTTTGAAATTCTGAATTTGCAA

AGTACTGTAAGAATAATTTATAGTAATGAGTTTAAAAATCAACTTTTTATTGCCTTCTCACCAGCTGCAA

AGTGTTTTGTACCAGTGAATTTTTGCAATAATGCAGTATGGTACATTTTTCAACTTTGAATAAAGAATAC

TTGAACTTGTCCTTGTTGAATC
```

A structure model of partial EZH2 protein based on the A chain of nuclear receptor binding SET domain protein 1 (NSD1) is provided in FIG. 11. This model corresponds to amino acid residues 533-732 of EZH2 sequence of SEQ ID NO: 1.

The corresponding amino acid sequence of the structure model seen in FIG. 11 is provided below. The residues in the substrate pocket domain are underlined. The residues in the SET domain are shown italic.

(SEQ ID NO: 6)
SCPCVIAQNFCEKFCQCSSECQNRFPGCRCKAQCNTKQCPCYLAVRECD

PDLCLTCGAADHWDSKNVSCKNCSIQRGSKK*HLLLAPSDVAGWGIFIKD*

*PVQKNEFISEY641CGEIISQDEADRRGKVYDKYMCSFLFNLNNDFV674*

*VDA677TRKGNKIR685FA687NHSVNPNCYAKVMMVNGDHRIGIFAKR*

*AIQTGEELFFDYRSQAD*

The catalytic site of EZH2 is believed to reside in a conserved domain of the protein known as the SET domain. The amino acid sequence of the SET domain of EZH2 is provided by the following partial sequence spanning amino acid residues 613-726 of Swiss-Prot Accession No. Q15910 (SEQ ID NO: 1):

(SEQ ID NO: 7)
HLLLAPSDVAGWGIFIKDPVQKNEFISEYCGEIISQDEADRRGKVYDKY

MCSFLFNLNNDFVVDATRKGNKIRFANHSVNPNCYAKVMMVNGDHRIGI

FAKRAIQTGEELFFDY.

The tyrosine (Y) residue shown underlined in SEQ ID NO: 7 is Tyr641 (Y641) in Swiss-Prot Accession No. Q15910 (SEQ ID NO: 1).

The SET domain of GenBank Accession No. NP_004447 (SEQ ID NO: 3) spans amino acid residues 618-731 and is identical to SEQ ID NO:6. The tyrosine residue corresponding to Y641 in Swiss-Prot Accession No. Q15910 shown underlined in SEQ ID NO: 7 is Tyr646 (Y646) in GenBank Accession No. NP_004447 (SEQ ID NO: 3).

The SET domain of GenBank Accession No. NP_694543 (SEQ ID NO: 5) spans amino acid residues 574-687 and is identical to SEQ ID NO: 7. The tyrosine residue corresponding to Y641 in Swiss-Prot Accession No. Q15910 shown underlined in SEQ ID NO: 7 is Tyr602 (Y602) in GenBank Accession No. NP_694543 (SEQ ID NO: 5).

The nucleotide sequence encoding the SET domain of GenBank Accession No. NP_004447 is (SEQ ID NO: 8)
catctattgctggcaccatctgacgtggcaggctgggggattttttatca aagatcctgtgcagaaaaatgaattcatctcagaatactgtggagagat -continued
```
tatttctcaagatgaagctgacagaagagggaaagtgtatgataaatac atgtgcagctttctgttcaacttgaacaatgattttgtggtggatgcaa cccgcaagggtaacaaaattcgttttgcaaatcattcggtaaatccaaa ctgctatgcaaaagttatgatggttaacggtgatcacaggataggtatt tttgccaagagagccatccagactggcgaagagctgttttttgattac,
```
where the codon encoding Y641 is shown underlined.

For purposes of this application, amino acid residue Y641 of human EZH2 is to be understood to refer to the tyrosine residue that is or corresponds to Y641 in Swiss-Prot Accession No. Q15910.

Also for purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

In one embodiment the amino acid sequence of a Y641 mutant of EZH2 differs from the amino acid sequence of wild-type human EZH2 only by substitution of a single amino acid residue corresponding to Y641 of wild-type human EZH2 by an amino acid residue other than tyrosine.

In one embodiment the amino acid sequence of a Y641 mutant of EZH2 differs from the amino acid sequence of wild-type human EZH2 only by substitution of phenylalanine (F) for the single amino acid residue corresponding to Y641 of wild-type human EZH2. The Y641 mutant of EZH2 according to this embodiment is referred to herein as a Y641F mutant or, equivalently, Y641F.

In one embodiment the amino acid sequence of a Y641 mutant of EZH2 differs from the amino acid sequence of wild-type human EZH2 only by substitution of histidine (H) for the single amino acid residue corresponding to Y641 of wild-type human EZH2. The Y641 mutant of EZH2 according to this embodiment is referred to herein as a Y641H mutant or, equivalently, Y641H.

In one embodiment the amino acid sequence of a Y641 mutant of EZH2 differs from the amino acid sequence of wild-type human EZH2 only by substitution of asparagine (N) for the single amino acid residue corresponding to Y641 of wild-type human EZH2. The Y641 mutant of EZH2 according to this embodiment is referred to herein as a Y641N mutant or, equivalently, Y641N.

In one embodiment the amino acid sequence of a Y641 mutant of EZH2 differs from the amino acid sequence of wild-type human EZH2 only by substitution of serine (S) for the single amino acid residue corresponding to Y641 of wild-type human EZH2. The Y641 mutant of EZH2 according to this embodiment is referred to herein as a Y641S mutant or, equivalently, Y641S.

In one embodiment the amino acid sequence of a Y641 mutant of EZH2 differs from the amino acid sequence of

```
Full amino acid sequence of Y641 mutant EZH2
                                                       (SEQ ID NO: 9)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEXCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP
Wherein x can be any amino acid residue other than tyrosine (Y)
``` wild-type human EZH2 only by substitution of cysteine (C) for the single amino acid residue corresponding to Y641 of wild-type human EZH2. The Y641 mutant of EZH2 according to this embodiment is referred to herein as a Y641C mutant or, equivalently, Y641C.

In one embodiment the amino acid sequence of a A677 mutant of EZH2 differs from the amino acid sequence of wild-type human EZH2 only by substitution of a non-alanine amino acid, preferably glycine (G) for the single amino acid residue corresponding to A677 of wild-type human EZH2. The A677 mutant of EZH2 according to this embodiment is referred to herein as an A677 mutant, and preferably an A677G mutant or, equivalently, A677G.

In one embodiment the amino acid sequence of a A687 mutant of EZH2 differs from the amino acid sequence of wild-type human EZH2 only by substitution of a non-alanine amino acid, preferably valine (V) for the single amino acid residue corresponding to A687 of wild-type human EZH2. The A687 mutant of EZH2 according to this embodiment is referred to herein as an A687 mutant and preferably an A687V mutant or, equivalently, A687V.

In one embodiment the amino acid sequence of a R685 mutant of EZH2 differs from the amino acid sequence of wild-type human EZH2 only by substitution of a non-arginine amino acid, preferably histidine (H) or cysteine (C) for the single amino acid residue corresponding to R685 of wild-type human EZH2. The R685 mutant of EZH2 according to this embodiment is referred to herein as an R685 mutant and preferably an R685C mutant or an R685H mutant or, equivalently, R685H or R685C.

In one embodiment the amino acid sequence of a mutant of EZH2 differs from the amino acid sequence of wild-type human EZH2 in one or more amino acid residues in its substrate pocket domain as defined in SEQ ID NO: 6. The mutant of EZH2 according to this embodiment is referred to herein as an EZH2 mutant.

Other exemplary substitution amino acid mutation includes a substitution at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C).

The mutation of the present invention may also include a substitution of serine (S) for the wild type residue asparagine (N) at amino acid position 322 of SEQ ID NO: 3 (N322S), a substitution of glutamine (Q) for the wild type residue arginine (R) at amino acid position 288 of SEQ ID NO: 3 (R288Q), a substitution of isoleucine (I) for the wild type residue threonine (T) at amino acid position 573 of SEQ ID NO: 3 (T573I), a substitution of glutamic acid (E) for the wild type residue aspartic acid (D) at amino acid position 664 of SEQ ID NO: 3 (D664E), a substitution of glutamine (Q) for the wild type residue arginine (R) at amino acid position 458 of SEQ ID NO: 5 (R458Q), a substitution of lysine (K) for the wild type residue glutamic acid (E) at amino acid position 249 of SEQ ID NO: 3 (E249K), a substitution of cysteine (C) for the wild type residue arginine (R) at amino acid position 684 of SEQ ID NO: 3 (R684C), a substitution of histidine (H) for the wild type residue arginine (R) at amino acid position 628 of SEQ ID NO: 11 (R628H), a substitution of histidine (H) for the wild type residue glutamine (Q) at amino acid position 501 of SEQ ID NO: 5 (Q501H), a substitution of asparagine (N) for the wild type residue aspartic acid (D) at amino acid position 192 of SEQ ID NO: 3 (D192N), a substitution of valine (V) for the wild type residue aspartic acid (D) at amino acid position 664 of SEQ ID NO: 3 (D664V), a substitution of leucine (L) for the wild type residue valine (V) at amino acid position 704 of SEQ ID NO: 3 (V704L), a substitution of serine (S) for the wild type residue proline (P) at amino acid position 132 of SEQ ID NO: 3 (P132S), a substitution of lysine (K) for the wild type residue glutamic acid (E) at amino acid position 669 of SEQ ID NO: 11 (E669K), a substitution of threonine (T) for the wild type residue alanine (A) at amino acid position 255 of SEQ ID NO: 3 (A255T), a substitution of valine (V) for the wild type residue glutamic acid (E) at amino acid position 726 of SEQ ID NO: 3 (E726V), a substitution of tyrosine (Y) for the wild type residue cysteine (C) at amino acid position 571 of SEQ ID NO: 3 (C571Y), a substitution of cysteine (C) for the wild type residue phenylalanine (F) at amino acid position 145 of SEQ ID NO: 3 (F145C), a substitution of threonine (T) for the wild type residue asparagine (N) at amino acid position 693 of SEQ ID NO: 3 (N693T), a substitution of serine (S) for the wild type residue phenylalanine (F) at amino acid position 145 of SEQ ID NO: 3 (F145S), a substitution of histidine (H) for the wild type residue glutamine (Q) at amino acid position 109 of SEQ ID NO: 11 (Q109H), a substitution of cysteine (C) for the wild type residue phenylalanine (F) at amino acid position 622 of SEQ ID NO: 11 (F622C), a substitution of arginine (R) for the wild type residue glycine (G) at amino acid position 135 of SEQ ID NO: 3 (G135R), a substitution of glutamine (Q) for the wild type residue arginine (R) at amino acid position 168 of SEQ ID NO: 5 (R168Q), a substitution of arginine (R) for the wild type residue glycine (G) at amino acid position 159 of SEQ ID NO: 3 (G159R), a substitution of cysteine (C) for the wild type residue arginine (R) at amino acid position 310 of SEQ ID NO: 5 (R310C), a substitution of histidine (H) for the wild type residue arginine (R) at amino acid position 561 of SEQ ID NO: 3 (R561H), a substitution of histidine (H) for the wild type residue arginine (R) at amino acid position 634 of SEQ ID NO: 11 (R634H), a substitution of arginine (R) for the wild type residue glycine (G) at amino acid position 660 of SEQ ID NO: 3 (G660R), a substitution of cysteine (C) for the wild type residue tyrosine (Y) at amino acid position 181 of SEQ ID NO: 3 (Y181C), a substitution of arginine (R) for the wild type residue histidine (H) at amino acid position 297 of SEQ ID NO: 3 (H297R), a substitution of serine (S) for the wild type residue cysteine (C) at amino acid position 612 of SEQ ID NO: 11 (C612S), a substitution of tyrosine (Y) for the wild type residue histidine (H) at amino acid position 694 of SEQ ID NO: 3 (H694Y), a substitution of alanine (A) for the wild type residue aspartic acid (D) at amino acid position 664 of SEQ ID NO: 3 (D664A), a substitution of threonine (T) for the wild type residue isoleucine (I) at amino acid position 150 of SEQ ID NO: 3 (I150T), a substitution of arginine (R) for the wild type residue isoleucine (I) at amino acid position 264 of SEQ ID NO: 3 (I264R), a substitution of leucine (L) for the wild type residue proline (P) at amino acid position 636 of SEQ ID NO: 3 (P636L), a substitution of threonine (T) for the wild type residue isoleucine (I) at amino acid position 713 of SEQ ID NO: 3 (I713T), a substitution of proline (P) for the wild type residue glutamine (Q) at amino acid position 501 of SEQ ID NO: 5 (Q501P), a substitution of glutamine (Q) for the wild type residue lysine (K) at amino acid position 243 of SEQ ID NO: 3 (K243Q), a substitution of aspartic acid (D) for the wild type residue glutamic acid (E) at amino acid position 130 of SEQ ID NO: 5 (E130D), a substitution of glycine (G) for the wild type residue arginine (R) at amino acid position 509 of SEQ ID NO: 3 (R509G), a substitution of histidine (H) for the wild type residue arginine (R) at amino acid position 566 of SEQ ID NO: 3 (R566H), a substitution of histidine (H) for the wild type residue aspartic acid (D) at amino acid position 677 of SEQ ID NO: 3 (D677H), a substitution of asparagine (N) for the wild type residue lysine (K) at amino acid position 466 of SEQ ID NO: 5 (K466N), a substitution of histidine (H) for the wild type residue arginine (R) at amino acid position 78 of SEQ ID NO: 3 (R78H), a substitution of methionine (M) for the wild type residue lysine (K) at amino acid position 1 of SEQ ID NO: 6 (K6M), a substitution of leucine (L) for the wild type residue serine (S) at amino acid position 538 of SEQ ID NO: 3 (S538L), a substitution of glutamine (Q) for the wild type residue leucine (L) at amino acid position 149 of SEQ ID NO: 3 (L149Q), a substitution of valine (V) for the wild type residue leucine (L) at amino acid position 252 of SEQ ID NO: 3 (L252V), a substitution of valine (V) for the wild type residue leucine (L) at amino acid position 674 of SEQ ID NO: 3 (L674V), a substitution of valine (V) for the wild type residue alanine (A) at amino acid position 656 of SEQ ID NO: 3 (A656V), a substitution of aspartic acid (D) for the wild type residue alanine (A) at amino acid position 731 of SEQ ID NO: 3 (Y731D), a substitution of threonine (T) for the wild type residue alanine (A) at amino acid position 345 of SEQ ID NO: 3 (A345T), a substitution of aspartic acid (D) for the wild type residue alanine (A) at amino acid position 244 of SEQ ID NO: 3 (Y244D), a substitution of tryptophan (W) for the wild type residue cysteine (C) at amino acid position 576 of SEQ ID NO: 3 (C576W), a substitution of lysine (K) for the wild type residue asparagine (N) at amino acid position 640 of SEQ ID NO: 3 (N640K), a substitution of lysine (K) for the wild type residue asparagine (N) at amino acid position 675 of SEQ ID NO: 3 (N675K), a substitution of tyrosine (Y) for the wild type residue aspartic acid (D) at amino acid position 579 of SEQ ID NO: 11 (D579Y), a substitution of isoleucine (I) for the wild type residue asparagine (N) at amino acid position 693 of SEQ ID NO: 3 (N693I), and a substitution of lysine (K) for the wild type residue asparagine (N) at amino acid position 693 of SEQ ID NO: 3 (N693K).

The mutation of the present invention may be a frameshift at amino acid position 730, 391, 461, 441, 235, 254, 564, 662, 715, 405, 685, 64, 73, 656, 718, 374, 592, 505, 730, or 363 of SEQ ID NO: 3, 5 or 11 or the corresponding nucleotide position of the nucleic acid sequence encoding SEQ ID NO: 3, 5, or 11. The mutation of the EZH2 may also be an insertion of a glutamic acid (E) between amino acid positions 148 and 149 of SEQ ID NO: 3, 5 or 21. Another example of EZH2 mutation is a deletion of glutamic acid (E) and leucine (L) at amino acid positions 148 and 149 of SEQ ID NO: 3, 5 or 11. The mutant EZH2 may further comprise a nonsense mutation at amino acid position 733, 25, 317, 62, 553, 328, 58, 207, 123, 63, 137, or 60 of SEQ ID NO: 3, 5 or 11.

Cells heterozygous for EZH2 would be expected to display a malignant phenotype due to the efficient formation of H3-K27me1 by the WT enzyme and the efficient, subsequent transition of this progenitor species to H3-K27me2, and, especially, H3-K27me3, by the mutant enzyme form(s).

Previous results point to dependency on enzymatic coupling between enzymes that perform H3-K27 mono-methylation and certain mutant forms of EZH2 for pathogenesis in follicular lymphoma and diffuse large B-cell lymphoma. For example, cells expressing Y641 mutant EZH2 may be more sensitive to small molecule EZH2 inhibitors than cells expressing WT EZH2. Specifically, cells expressing Y641 mutant EZH2 show reduced growing, dividing or proliferation, or even undergo apoptosis or necrosis after the treatment of EZH2 inhibitors. In contrast, cells expressing WT EZH2 are not responsive to the anti-proliferative effect of the EZH2 inhibitors (U.S. Patent Application No. 61/381,684; incorporated herein by reference in its entirety.)

An aspect of the present invention is a method for treating or alleviating a symptom of cancer or precancerous condition in a subject by administering to a subject expressing a mutant EZH2 comprising a mutation in the substrate pocket domain as defined in SEQ ID NO: 6 a therapeutically effective amount of an EZH2 inhibitor as described herein, e.g., a compound of Formula (IIa) in combination with another agent suitable to be administered together simultaneously, sequentially, or in alternation.

Another aspect of the invention is a method for inhibiting in a subject conversion of H3-K27 to trimethylated H3-K27. The inhibition can involve inhibiting in a subject conversion of unmethylated H3-K27 to monomethylated H3-K27, conversion of monomethylated H3-K27 to dimethylated H3-K27, conversion of dimethylated H3-K27 to trimethylated H3-K27, or any combination thereof, including, for example, conversion of monomethylated H3-K27 to dimethylated H3-K27 and conversion of dimethylated H3-K27 to trimethylated H3-K27. As used herein, unmethylated H3-K27 refers to histone H3 with no methyl group covalently linked to the amino group of lysine 27. As used herein, monomethylated H3-K27 refers to histone H3 with a single methyl group covalently linked to the amino group of lysine 27. Monomethylated H3-K27 is also referred to herein as H3-K27me1. As used herein, dimethylated H3-K27 refers to histone H3 with two methyl groups covalently linked to the amino group of lysine 27. Dimethylated H3-K27 is also referred to herein as H3-K27me2. As used herein, trimethylated H3-K27 refers to histone H3 with three methyl groups covalently linked to the amino group of lysine 27. Trimethylated H3-K27 is also referred to herein as H3-K27me3.

Histone H3 is a 136 amino acid long protein, the sequence of which is known. See, for example, GenBank Accession No. CAB02546, the content of which is incorporated herein by reference. As disclosed further herein, in addition to full-length histone H3, peptide fragments of histone H3 comprising the lysine residue corresponding to K27 of full-length histone H3 can be used as substrate for EZH2 (and likewise for mutant forms of EZH2) to assess conversion of H3-K27m1 to H3-K27m2 and conversion of H3-K27m2 to H3-K27m3. In one embodiment, such peptide fragment corresponds to amino acid residues 21-44 of histone H3. Such peptide fragment has the amino acid sequence LATKAARKSAPATGGVKKPHRYRP (SEQ ID NO: 10).

A composition of the present invention comprises a compound of Formula (IIa) and one or more other therapeutic agents, or a pharmaceutically acceptable salt thereof. The compounds of Formula (IIa) are suitable for administration as part of a combination therapy with one or more other therapeutic agents or treatment modality, suitable to be administered together, sequentially, or in alternation. Other compounds of Formula (IIa) suitable for the methods of the invention are described in U.S. Publication 20120264734, the contents of which are hereby incorporated by reference in their entireties.

The present invention provides the compounds of Formula (IIa):

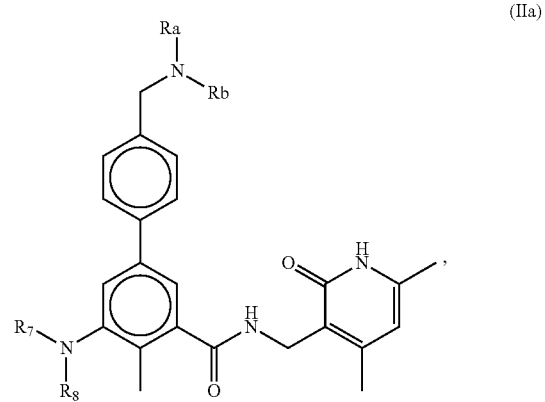

(IIa)

or a pharmaceutically acceptable salts or esters thereof, wherein $R_7$, $R_8$, $R_a$, and $R_b$ are defined herein.

The compounds of Formula (IIa) can include one or more of the following features:

For example, each of $R_a$ and $R_b$ independently is H or $C_1$-$C_6$ alkyl optionally substituted with one or more -$Q_3$-$T_3$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more $-Q_3-T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl, and the ring is optionally substituted with one or more $-Q_3-T_3$.

For example, one or more $-Q_3-T_3$ are oxo.

For example, $Q_3$ is a bond or unsubstituted or substituted $C_1-C_3$ alkyl linker.

For example, $T_3$ is H, halo, 4 to 7-membered heterocycloalkyl, $C_1-C_3$ alkyl, $OR_d$, $COOR_d$, $-S(O)_2R_4$, or $-NR_dR_e$.

For example, each of $R_d$ and $R_e$ independently being H or $C_1-C_6$ alkyl.

For example, $R_7$ is $C_3-C_8$ cycloalkyl or 4 to 7-membered heterocycloalkyl, each optionally substituted with one or more $-Q_5-T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more $-Q_5-T_5$.

For example, $R_7$ is cyclopentyl cyclohexyl or tetrahydro-2H-thiopyranyl, each of which is optionally substituted with one or more $-Q_5-T_5$.

For example, $Q_5$ is NHC(O) and $T_5$ is $C_1-C_6$ alkyl or $C_1-C_6$ alkoxy, each For example, one or more $-Q_5-T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1-C_6$ alkylamino, di-$C_1-C_6$ alkylamino.

For example, $Q_5$ is CO, $S(O)_2$, or NHC(O); and $T_5$ is $C_1-C_6$ alkyl, $C_1-C_6$ alkoxyl, $C_3-C_8$ cycloalkyl, or 4 to 7-membered heterocycloalkyl.

For example, $R_8$ is H or $C_1-C_6$ alkyl which is optionally substituted with one or more substituents selected from the group consisting of halo, hydroxyl, COOH, C(O)O—$C_1-C_6$ alkyl, cyano, $C_1-C_6$ alkoxyl, amino, mono-$C_1-C_6$ alkylamino, and di-$C_1-C_6$ alkylamino.

For example, $R_8$ is H, methyl, or ethyl.

In one embodiment, the compound of the invention is Compound 44

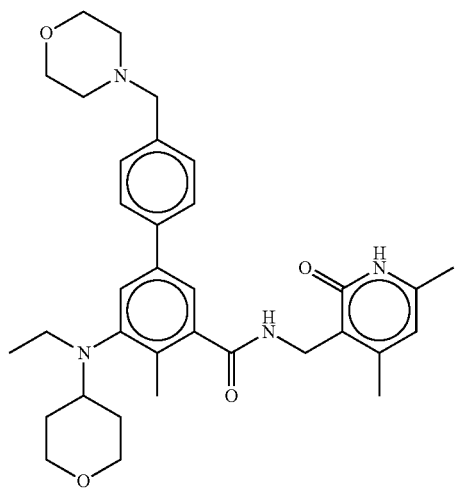

or a pharmaceutically acceptable salt thereof.

In one embodiment, the compound of the invention is the compound itself, i.e., the free base or "naked" molecule. In another embodiment, the compound is a salt thereof, e.g., a mono-HCl or tri-HCl salt, mono-HBr or tri-HBr salt of the naked molecule.

Representative compounds of the present invention include compounds listed in Table 1.
In the table below, each occurrence

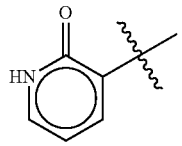

of should be construed as

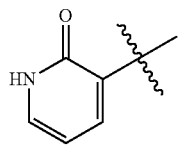

TABLE 1

| Compound Number | Structure | MS (M + 1)$^+$ |
|---|---|---|
| 1 | 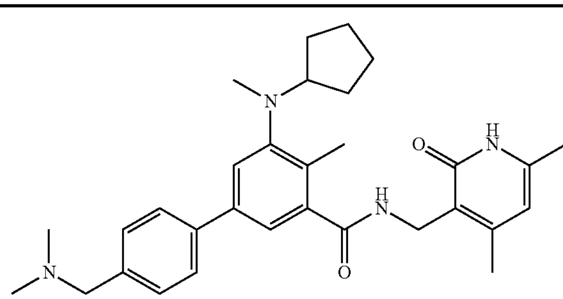 | 501.39 |

TABLE 1-continued

| Compound Number | Structure | MS (M + 1)+ |
|---|---|---|
| 2 | 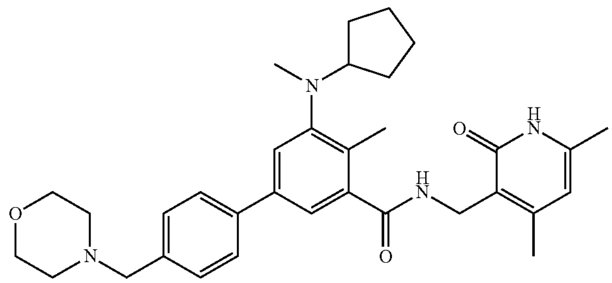 [SMILES: Cc1cc(C)c(CNC(=O)c2cc(-c3ccc(CN4CCOCC4)cc3)cc(N(C)C3CCCC3)c2C)c(=O)[nH]1] | 543.22 |
| 3 | 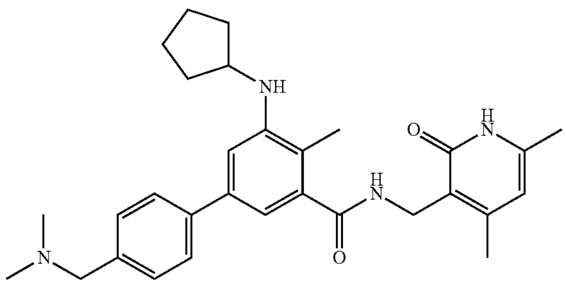 | 486.21 |
| 4 | 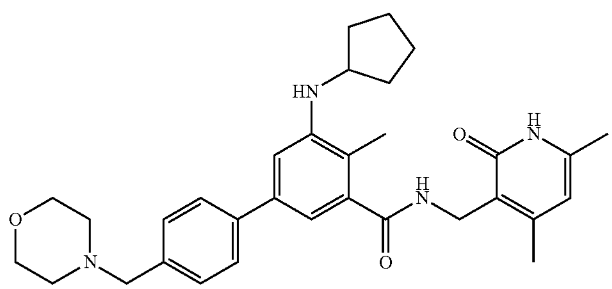 [SMILES: Cc1cc(C)c(CNC(=O)c2cc(-c3ccc(CN4CCOCC4)cc3)cc(NC3CCCC3)c2C)c(=O)[nH]1] | 529.30 |
| 11 | 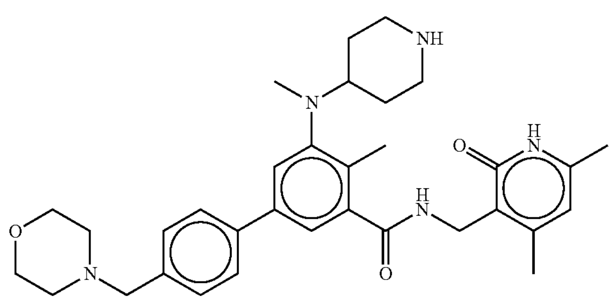 | 558.45 |
| 12 | 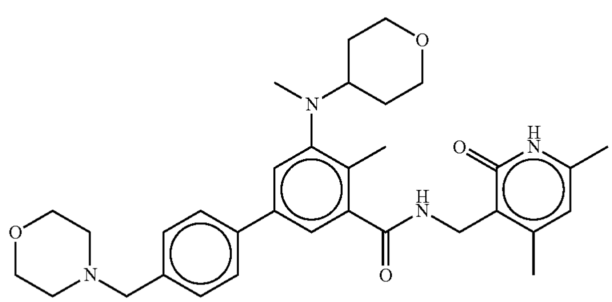 | 559.35 |

TABLE 1-continued

| Compound Number | Structure | MS (M + 1)+ |
|---|---|---|
| 13 | 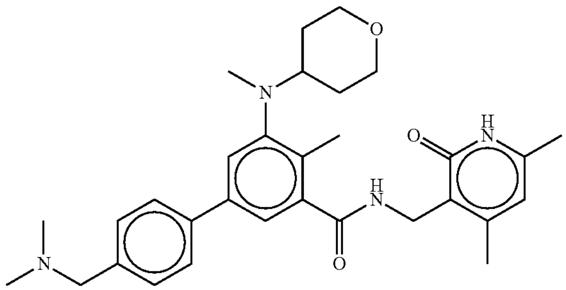 | 517.3 |
| 14 | 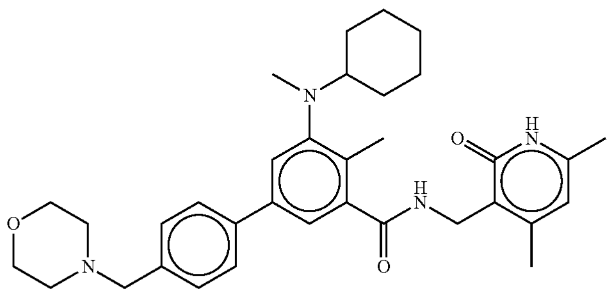 | 557.4 |
| 16 | 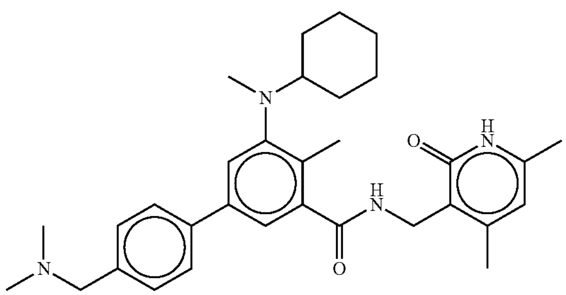 | 515.4 |
| 20 | 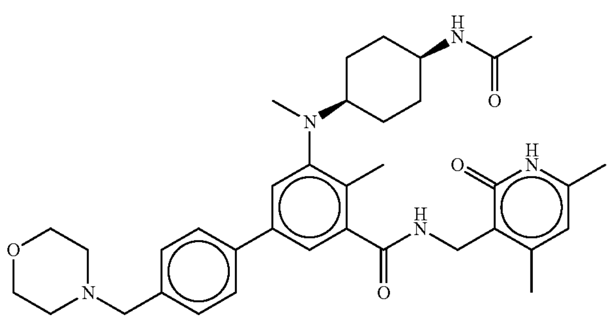 | 614.4 |
| 21 | 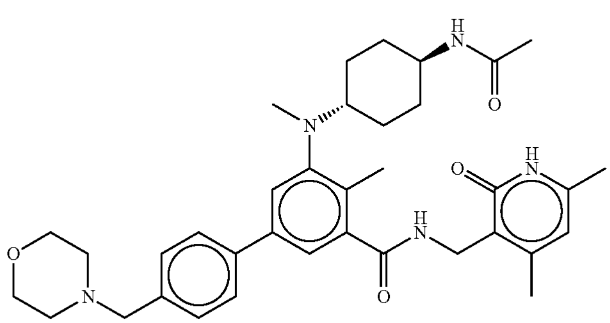 | 614.4 |

TABLE 1-continued

| Compound Number | Structure | MS (M + 1)+ |
|---|---|---|
| 27 | 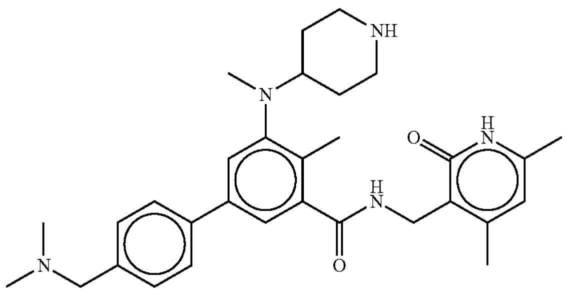 | 516.35 |
| 36 | 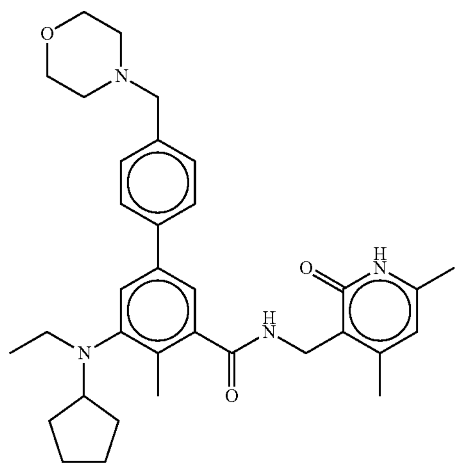 | 557.35 |
| 39 | 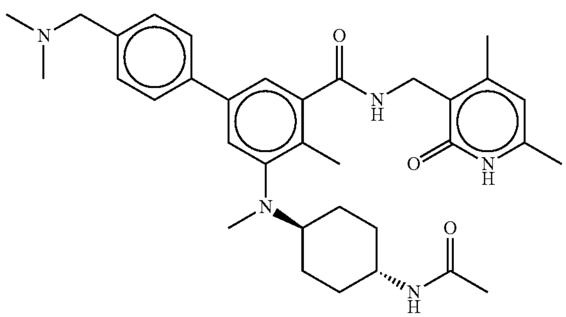 | 572.35 |
| 40 | 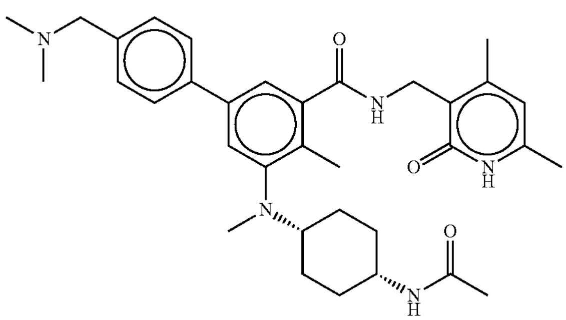 | 572.35 |

TABLE 1-continued

| Compound Number | Structure | MS (M + 1)+ |
|---|---|---|
| 42 | 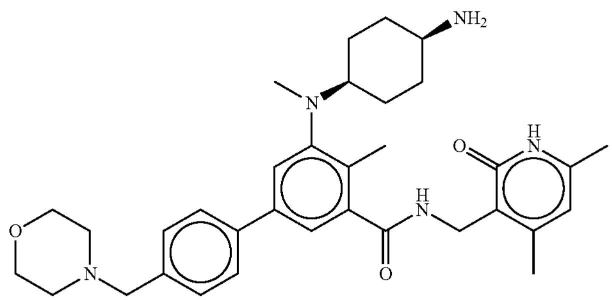 | 572.4 |
| 43 | 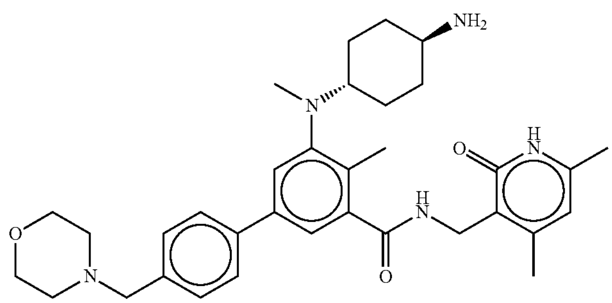 | 572.6 |
| 44 | 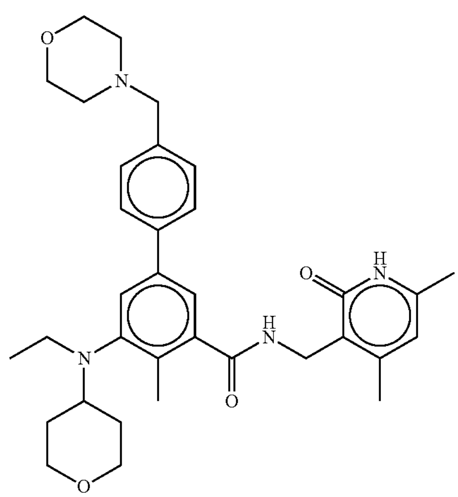 | 573.40 |
| 47 | 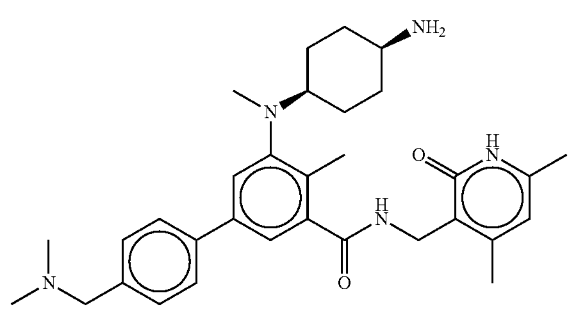 | 530.35 |

TABLE 1-continued

| Compound Number | Structure | MS (M + 1)+ |
|---|---|---|
| 59 | 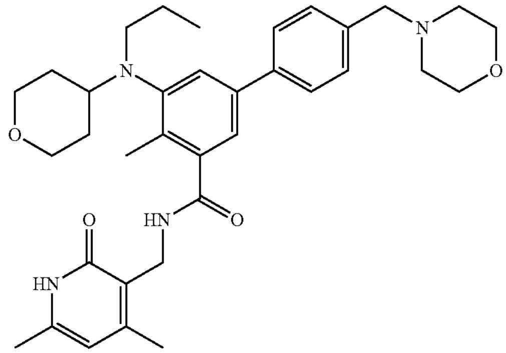 [SMILES: CCCN(c1cc(-c2ccc(CN3CCOCC3)cc2)cc(C(=O)NCc2c(C)cc(C)[nH]c2=O)c1C)C1CCOCC1] | 587.40 |
| 60 | 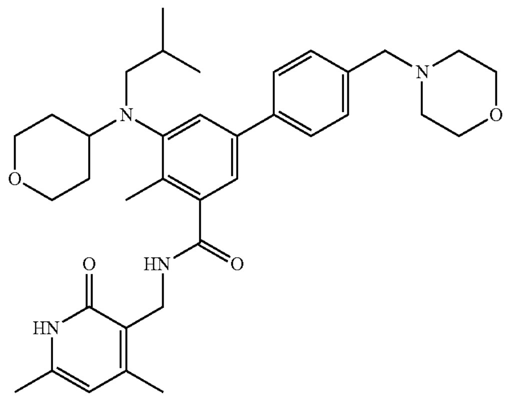 [SMILES: Cc1cc(C)c(CNC(=O)c2cc(-c3ccc(CN4CCOCC4)cc3)cc(N(CC(C)C)C3CCOCC3)c2C)c(=O)[nH]1] | 601.30 |
| 61 | 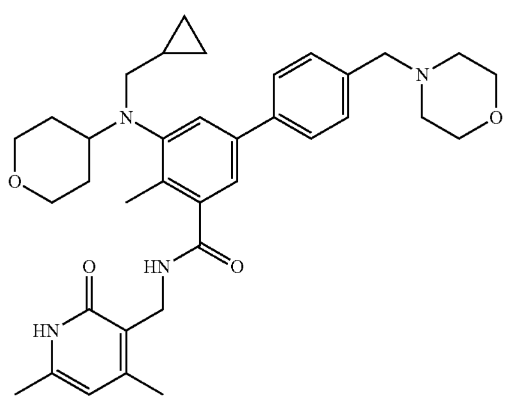 [SMILES: Cc1cc(C)c(CNC(=O)c2cc(-c3ccc(CN4CCOCC4)cc3)cc(N(CC3CC3)C3CCOCC3)c2C)c(=O)[nH]1] | 599.35 |
| 62 | 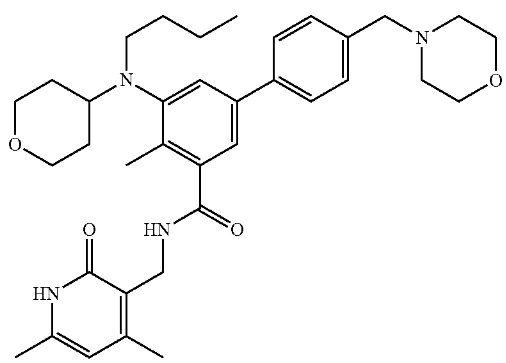 [SMILES: CCCCN(c1cc(-c2ccc(CN3CCOCC3)cc2)cc(C(=O)NCc2c(C)cc(C)[nH]c2=O)c1C)C1CCOCC1] | 601.35 |

TABLE 1-continued
| Compound Number | Structure | MS (M + 1)+ |
|---|---|---|
| 63 | 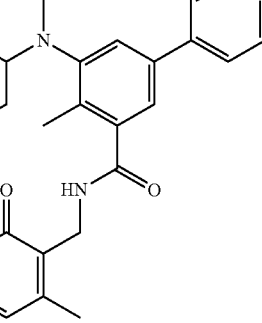 | 613.35 |
| 65 | 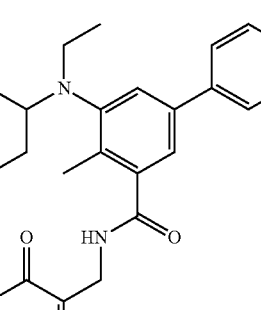 | 531.30 |
| 66 | 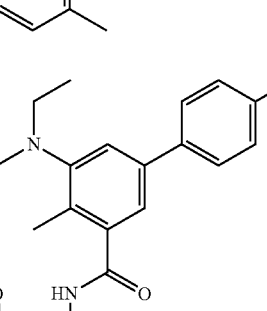 | 586.40 |
| 67 | 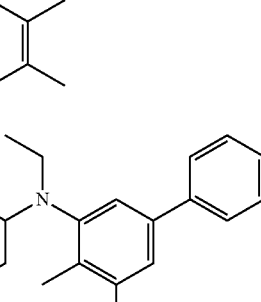 | 585.25 |

TABLE 1-continued

| Compound Number | Structure | MS (M + 1)+ |
|---|---|---|
| 68 | 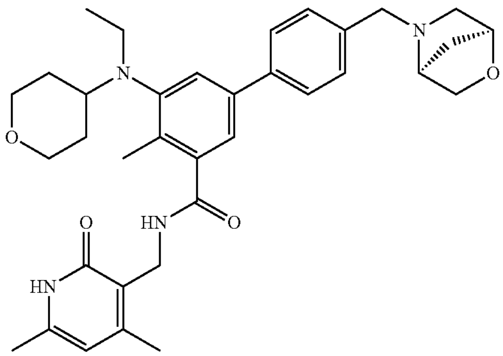 [SMILES: CCN(c1cc(-c2ccc(CN3C[C@@H]4C[C@H]3CO4)cc2)cc(C(=O)NCc2c(C)cc(C)[nH]c2=O)c1C)C1CCOCC1] | 585.35 |
| 69 | 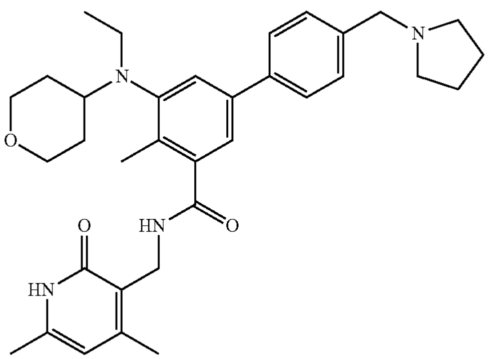 [SMILES: CCN(c1cc(-c2ccc(CN3CCCC3)cc2)cc(C(=O)NCc2c(C)cc(C)[nH]c2=O)c1C)C1CCOCC1] | 557.25 |
| 70 | 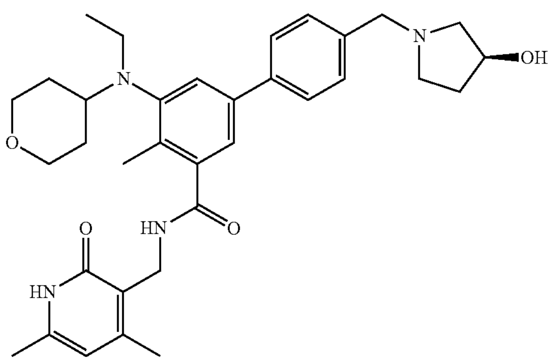 [SMILES: CCN(c1cc(-c2ccc(CN3CC[C@H](O)C3)cc2)cc(C(=O)NCc2c(C)cc(C)[nH]c2=O)c1C)C1CCOCC1] | 573.40 |
| 71 | 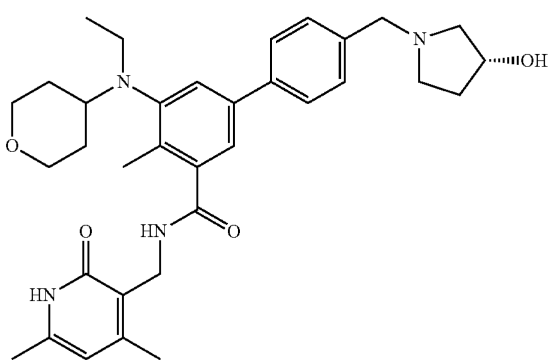 [SMILES: CCN(c1cc(-c2ccc(CN3CC[C@@H](O)C3)cc2)cc(C(=O)NCc2c(C)cc(C)[nH]c2=O)c1C)C1CCOCC1] | 573.40 |

TABLE 1-continued

| Compound Number | Structure | MS (M + 1)+ |
|---|---|---|
| 72 | 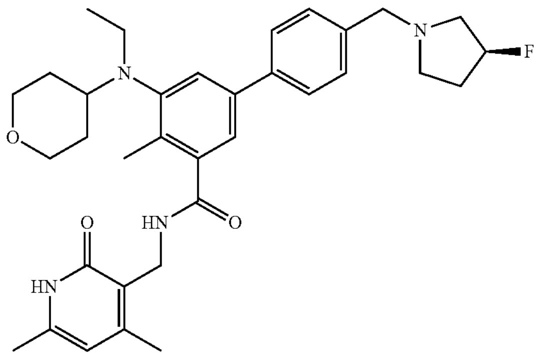 [SMILES: CCN(c1cc(-c2ccc(CN3CC[C@H](F)C3)cc2)cc(C(=O)NCc2c(C)cc(C)[nH]c2=O)c1C)C1CCOCC1] | 575.35 |
| 73 | 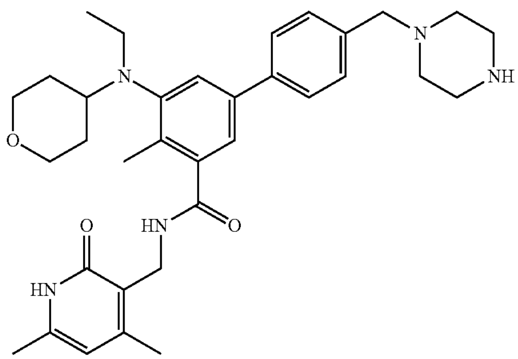 [SMILES: CCN(c1cc(-c2ccc(CN3CCNCC3)cc2)cc(C(=O)NCc2c(C)cc(C)[nH]c2=O)c1C)C1CCOCC1] | 572.10 |
| 74 | 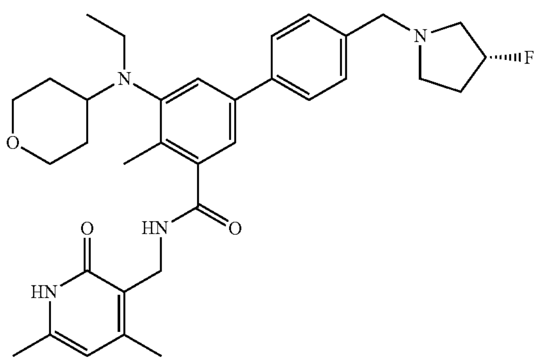 [SMILES: CCN(c1cc(-c2ccc(CN3CC[C@@H](F)C3)cc2)cc(C(=O)NCc2c(C)cc(C)[nH]c2=O)c1C)C1CCOCC1] | 575.35 |
| 75 | 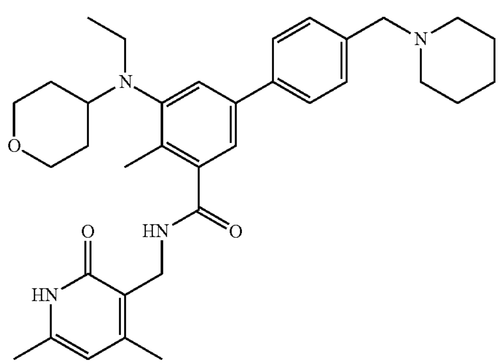 [SMILES: CCN(c1cc(-c2ccc(CN3CCCCC3)cc2)cc(C(=O)NCc2c(C)cc(C)[nH]c2=O)c1C)C1CCOCC1] | 571.25 |

TABLE 1-continued

| Compound Number | Structure | MS (M + 1)+ |
|---|---|---|
| 76 | 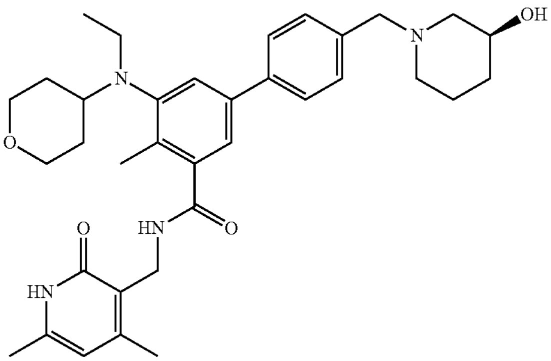 [SMILES: CCN(c1cc(-c2ccc(CN3CCC[C@H](O)C3)cc2)cc(C(=O)NCc2c(C)cc(C)[nH]c2=O)c1C)C1CCOCC1] | 587.40 |
| 77 | 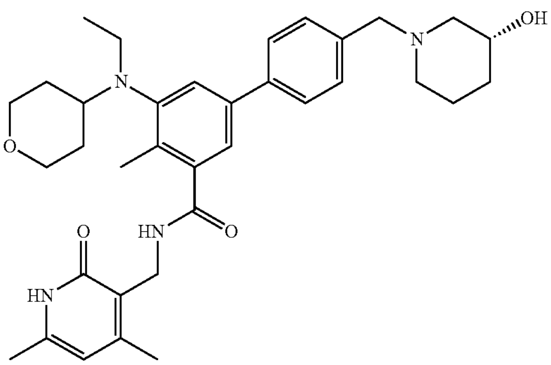 [SMILES: CCN(c1cc(-c2ccc(CN3CCC[C@@H](O)C3)cc2)cc(C(=O)NCc2c(C)cc(C)[nH]c2=O)c1C)C1CCOCC1] | 587.45 |
| 78 | 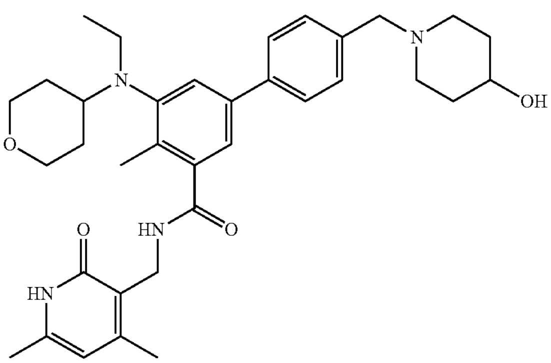 [SMILES: CCN(c1cc(-c2ccc(CN3CCC(O)CC3)cc2)cc(C(=O)NCc2c(C)cc(C)[nH]c2=O)c1C)C1CCOCC1] | 587.20 |
| 79 | 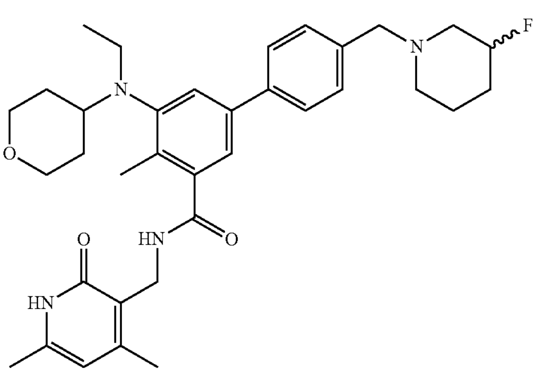 [SMILES: CCN(c1cc(-c2ccc(CN3CCCC(F)C3)cc2)cc(C(=O)NCc2c(C)cc(C)[nH]c2=O)c1C)C1CCOCC1] | 589.35 |

TABLE 1-continued

| Compound Number | Structure | MS (M + 1)+ |
|---|---|---|
| 80 | 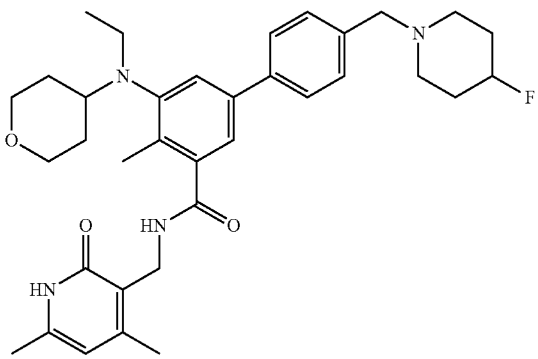 [SMILES: CCN(c1cc(-c2ccc(CN3CCC(F)CC3)cc2)cc(C(=O)NCc2c(C)cc(C)[nH]c2=O)c1C)C1CCOCC1] | 589.30 |
| 81 | 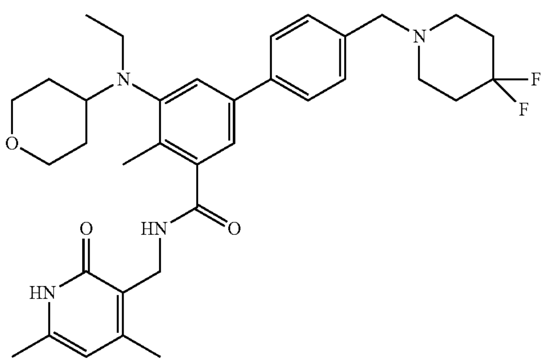 [SMILES: CCN(c1cc(-c2ccc(CN3CCC(F)(F)CC3)cc2)cc(C(=O)NCc2c(C)cc(C)[nH]c2=O)c1C)C1CCOCC1] | 607.35 |
| 82 | 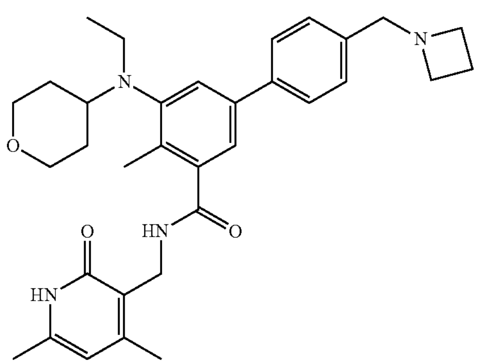 [SMILES: CCN(c1cc(-c2ccc(CN3CCC3)cc2)cc(C(=O)NCc2c(C)cc(C)[nH]c2=O)c1C)C1CCOCC1] | 543.40 |
| 83 | 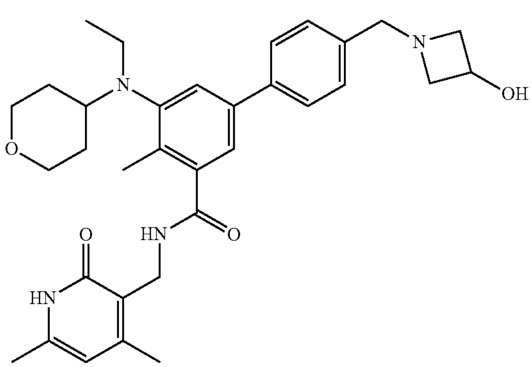 [SMILES: CCN(c1cc(-c2ccc(CN3CC(O)C3)cc2)cc(C(=O)NCc2c(C)cc(C)[nH]c2=O)c1C)C1CCOCC1] | 559.80 |

TABLE 1-continued

| Compound Number | Structure | MS (M + 1)+ |
|---|---|---|
| 84 | 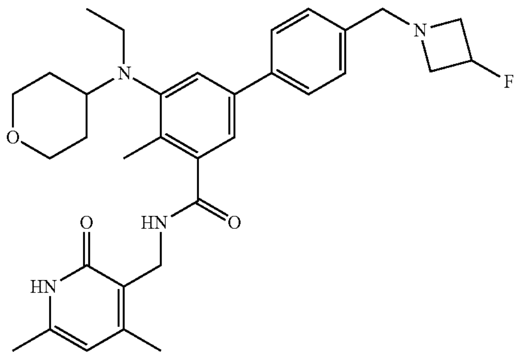 [SMILES: CCN(c1cc(-c2ccc(CN3CC(F)C3)cc2)cc(C(=O)NCc2c(C)cc(C)[nH]c2=O)c1C)C1CCOCC1] | 561.25 |
| 85 | 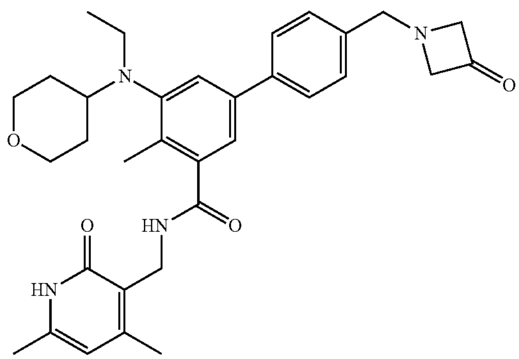 [SMILES: CCN(c1cc(-c2ccc(CN3CC(=O)C3)cc2)cc(C(=O)NCc2c(C)cc(C)[nH]c2=O)c1C)C1CCOCC1] | |
| 86 | 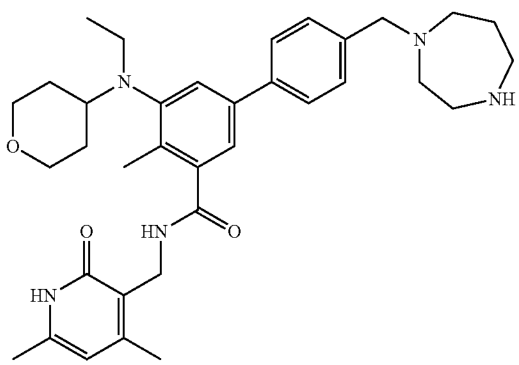 | 585.37 |
| 87 | 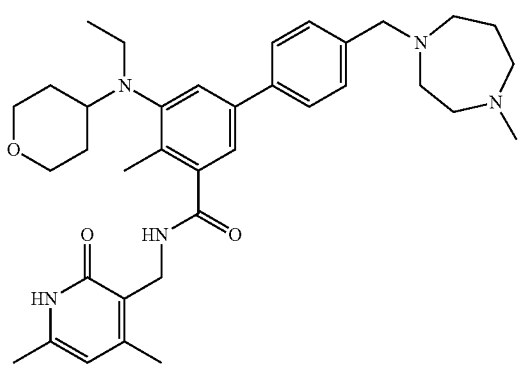 | 600.30 |

TABLE 1-continued

| Compound Number | Structure | MS (M + 1)+ |
|---|---|---|
| 88 | 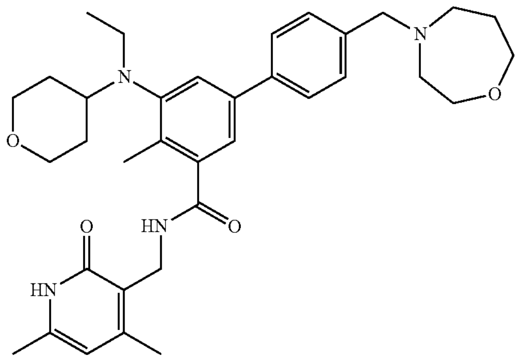 [SMILES: CCN(c1cc(-c2ccc(CN3CCCOCC3)cc2)cc(C(=O)NCc2c(C)cc(C)[nH]c2=O)c1C)C1CCOCC1] | 587.40 |
| 89 | 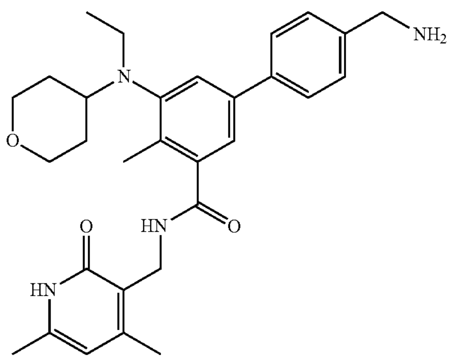 [SMILES: CCN(c1cc(-c2ccc(CN)cc2)cc(C(=O)NCc2c(C)cc(C)[nH]c2=O)c1C)C1CCOCC1] | 503.40 |
| 90 | 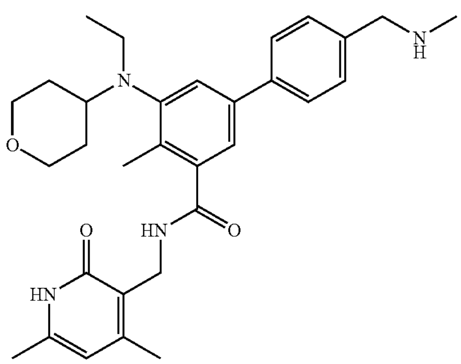 | 517.30 |
| 91 | 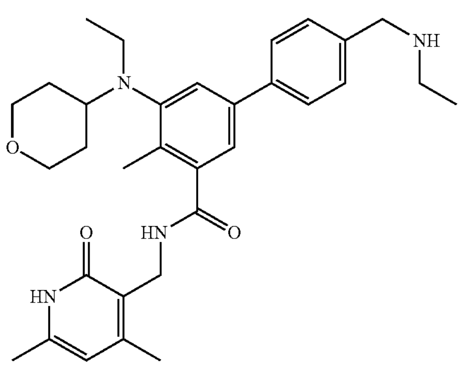 [SMILES: CCNCc1ccc(-c2cc(C(=O)NCc3c(C)cc(C)[nH]c3=O)c(C)c(N(CC)C3CCOCC3)c2)cc1] | 531.35 |

TABLE 1-continued
| Compound Number | Structure | MS (M + 1)+ |
|---|---|---|
| 92 | 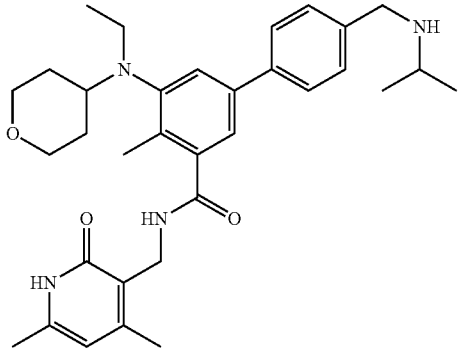 [SMILES: CCN(c1cc(-c2ccc(CNC(C)C)cc2)cc(C(=O)NCc2c(C)cc(C)[nH]c2=O)c1C)C1CCOCC1] | 545.40 |
| 93 | 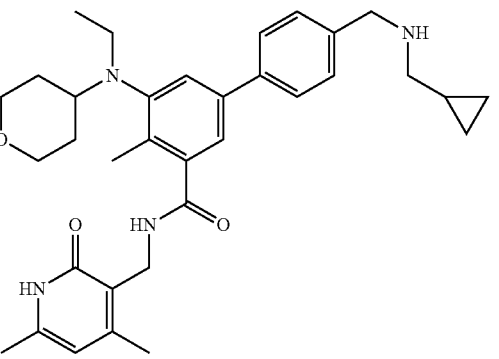 | 557.35 |
| 94 | 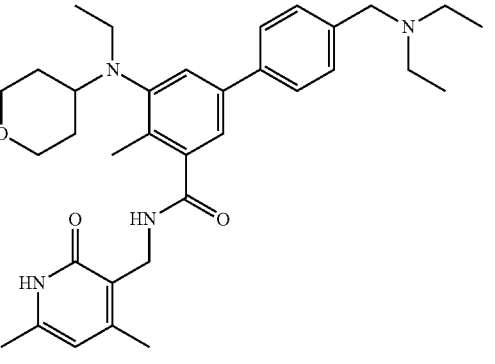 | 559.20 |
| 95 | 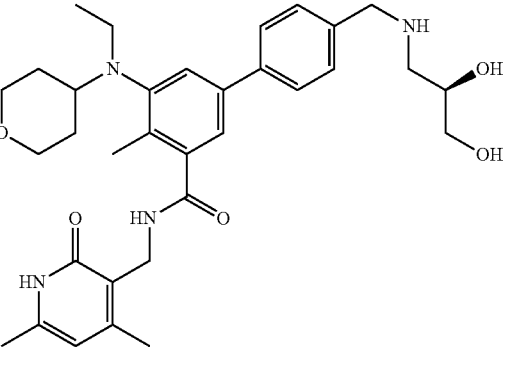 | 599.35 (M + Na) |

TABLE 1-continued
| Compound Number | Structure | MS (M + 1)+ |
|---|---|---|
| 96 | 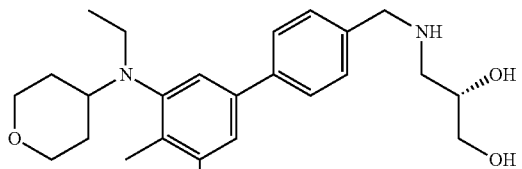 | 577.25 |
| 97 | 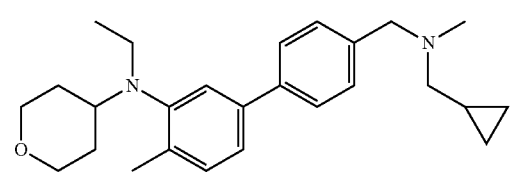 | 571.40 |
| 98 | 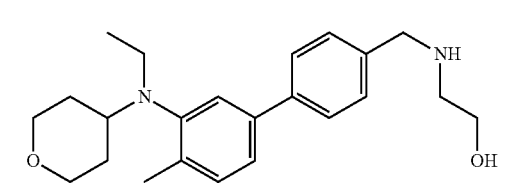 | 547.35 |
| 99 | 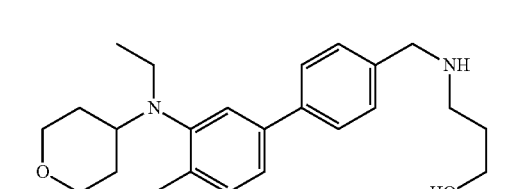 | 561.30 |

TABLE 1-continued

| Compound Number | Structure | MS (M + 1)⁺ |
|---|---|---|
| 100 | 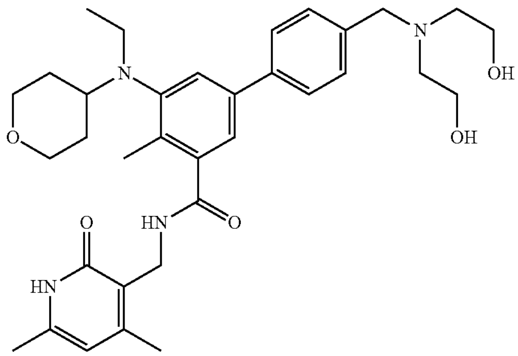 [SMILES: CCN(c1cc(-c2ccc(CN(CCO)CCO)cc2)cc(C(=O)NCc2c(C)cc(C)[nH]c2=O)c1C)C1CCOCC1] | 591.25 |
| 101 | 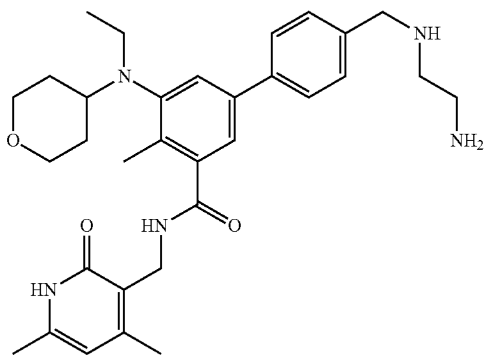 [SMILES: CCN(c1cc(-c2ccc(CNCCN)cc2)cc(C(=O)NCc2c(C)cc(C)[nH]c2=O)c1C)C1CCOCC1] | 546.35 |
| 102 | 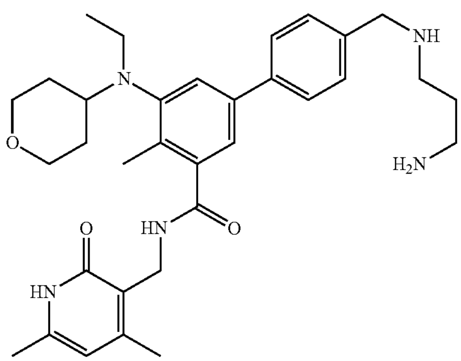 [SMILES: CCN(c1cc(-c2ccc(CNCCCN)cc2)cc(C(=O)NCc2c(C)cc(C)[nH]c2=O)c1C)C1CCOCC1] | 560.20 |
| 103 | 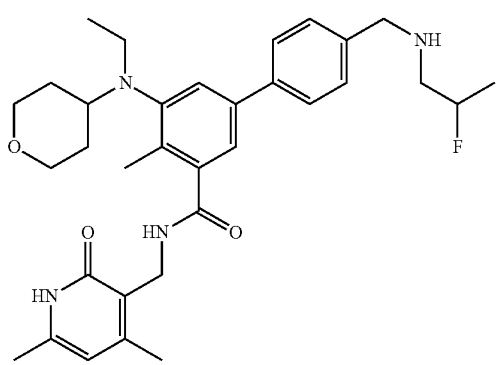 [SMILES: CCN(c1cc(-c2ccc(CNCC(C)F)cc2)cc(C(=O)NCc2c(C)cc(C)[nH]c2=O)c1C)C1CCOCC1] | 567.30 |

TABLE 1-continued

| Compound Number | Structure | MS (M + 1)+ |
|---|---|---|
| 104 | 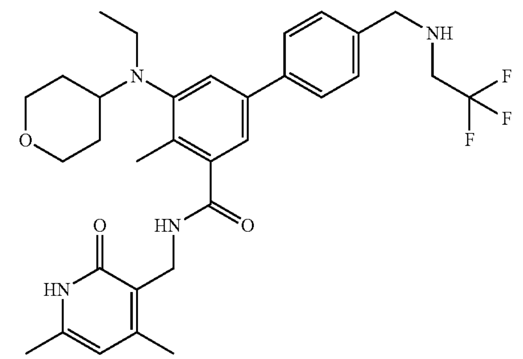 [SMILES: CCN(c1cc(-c2ccc(CNCC(F)(F)F)cc2)cc(C(=O)NCc2c(C)cc(C)[nH]c2=O)c1C)C1CCOCC1] | 585.25 |
| 105 | 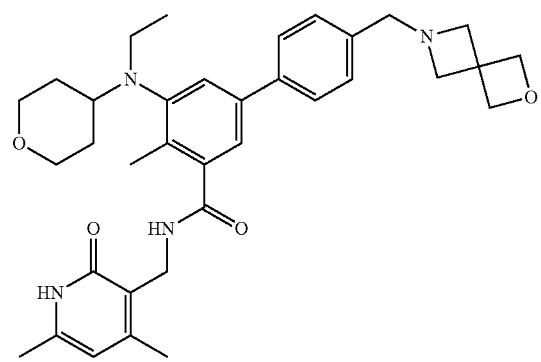 [SMILES: CCN(c1cc(-c2ccc(CN3CC4(COC4)C3)cc2)cc(C(=O)NCc2c(C)cc(C)[nH]c2=O)c1C)C1CCOCC1] | 585.40 |
| 107 | 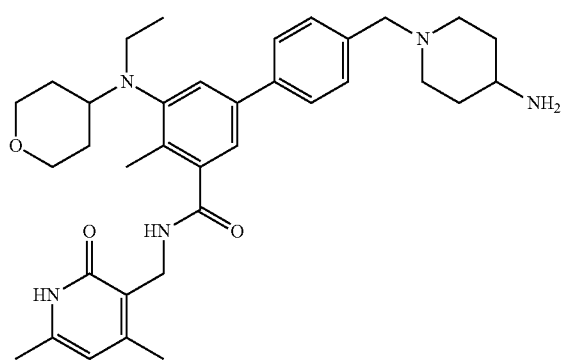 [SMILES: CCN(c1cc(-c2ccc(CN3CCC(N)CC3)cc2)cc(C(=O)NCc2c(C)cc(C)[nH]c2=O)c1C)C1CCOCC1] | |
| 108 | 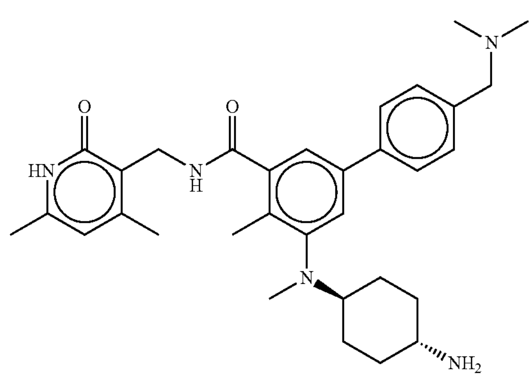 | 530.35 |

TABLE 1-continued

| Compound Number | Structure | MS (M + 1)+ |
|---|---|---|
| 114 | 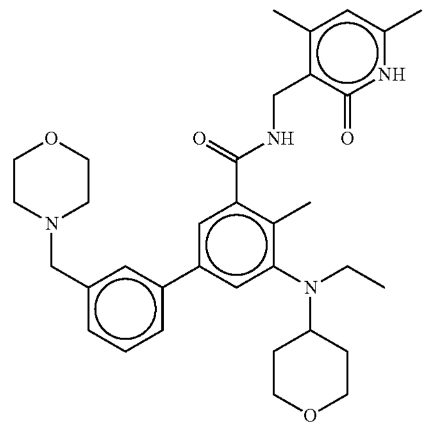 | 573.25 |
| 115 | 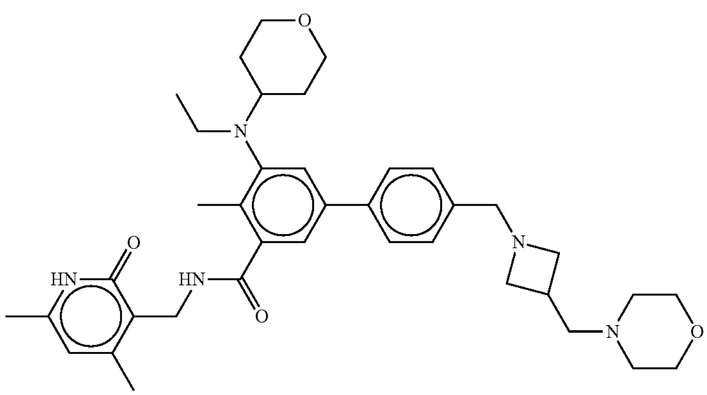 | 642.45 |
| 116 | 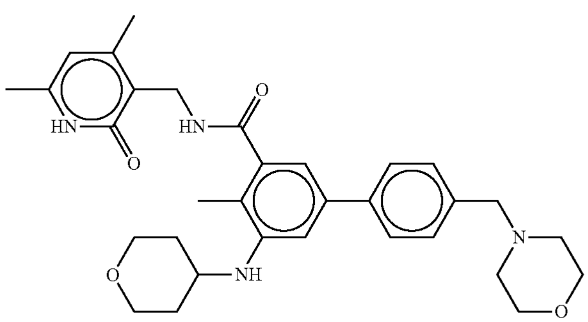 | 545.15 |
| 117 | 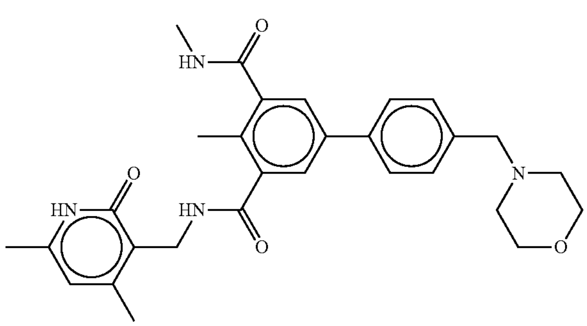 | 489.20 |

TABLE 1-continued

| Compound Number | Structure | MS (M + 1)+ |
|---|---|---|
| 119 | 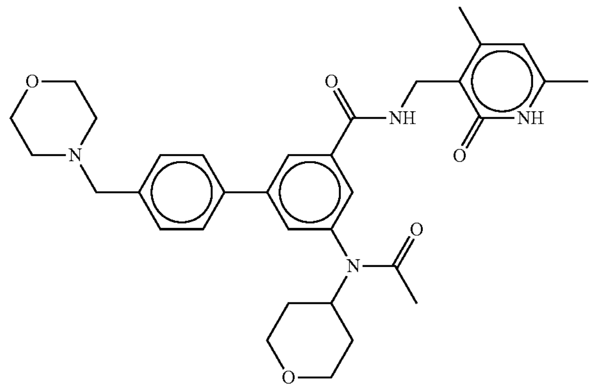 | 609.35 |
| 122 | 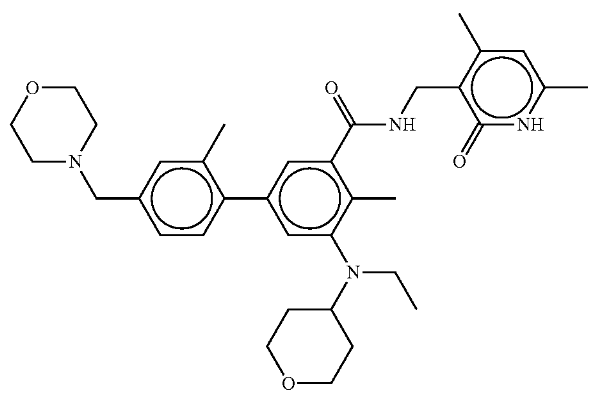 | 587.55 |
| 124 | 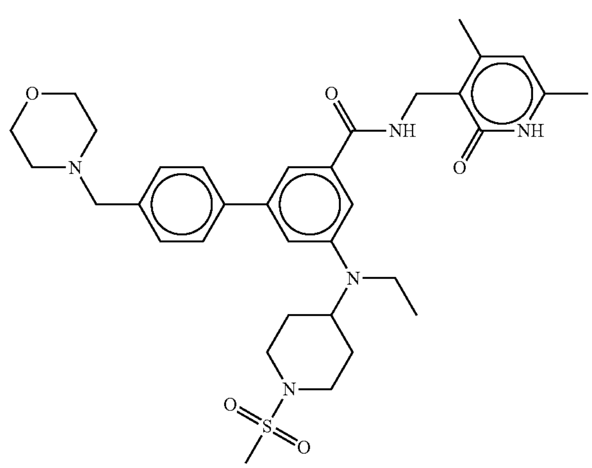 | 650.85 |

TABLE 1-continued

| Compound Number | Structure | MS (M + 1)+ |
|---|---|---|
| 125 | 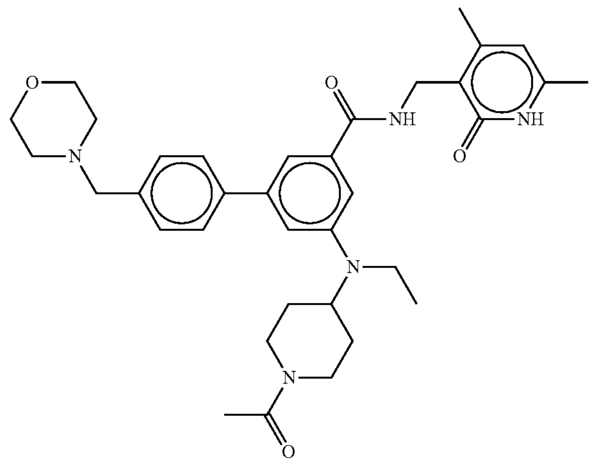 | 614.75 |
| 126 | 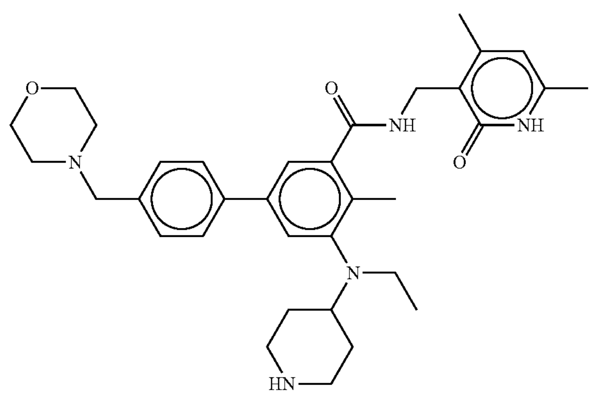 | 572.35 |
| 127 | 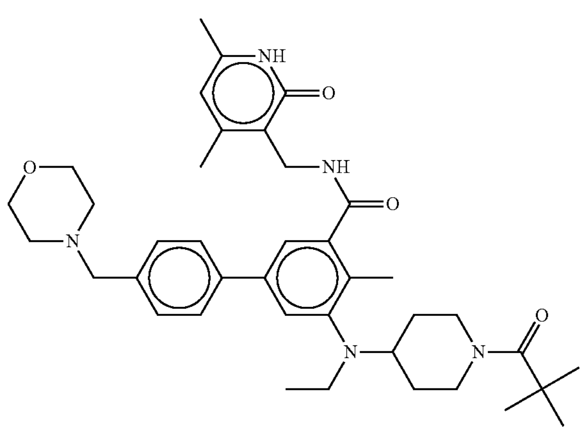 | 656.65 |

TABLE 1-continued

| Compound Number | Structure | MS (M + 1)+ |
|---|---|---|
| 128 | 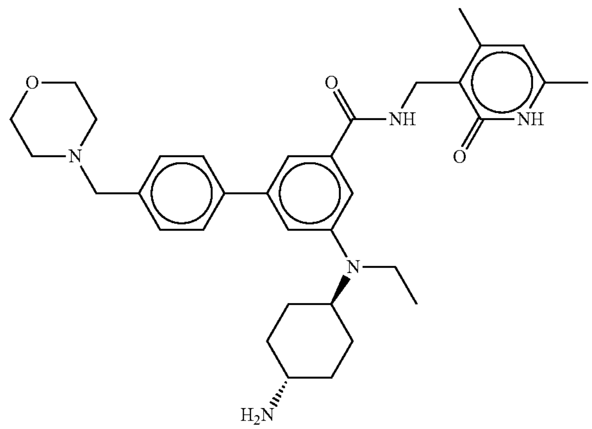 | 586.45 |
| 129 | 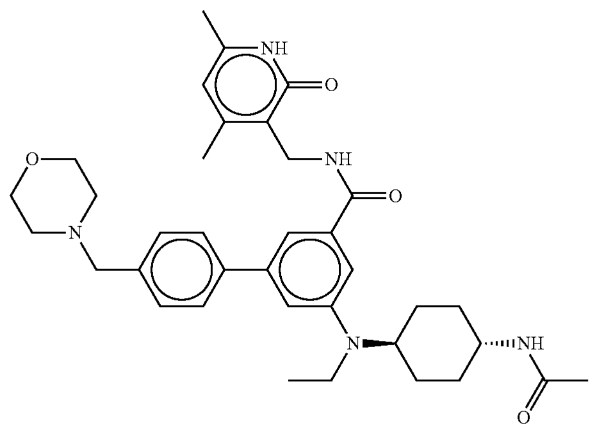 | 628.35 |
| 130 | 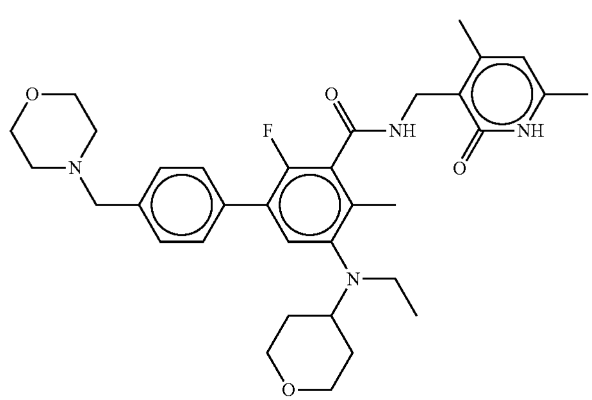 | 591.2 |

TABLE 1-continued

| Compound Number | Structure | MS (M + 1)+ |
|---|---|---|
| 131 | 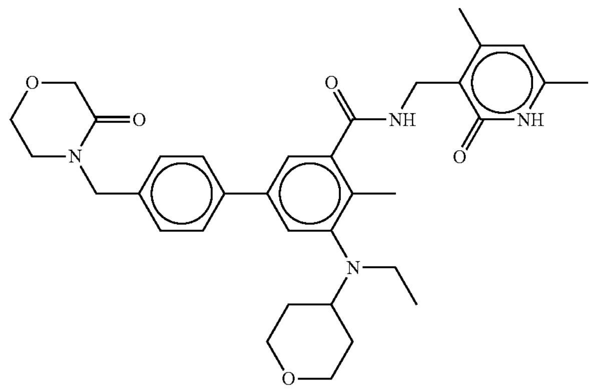 | 587.35 |
| 132 | 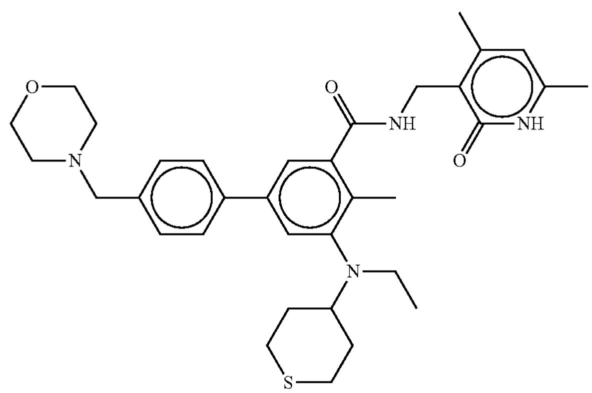 | 589.25 |
| 133 | 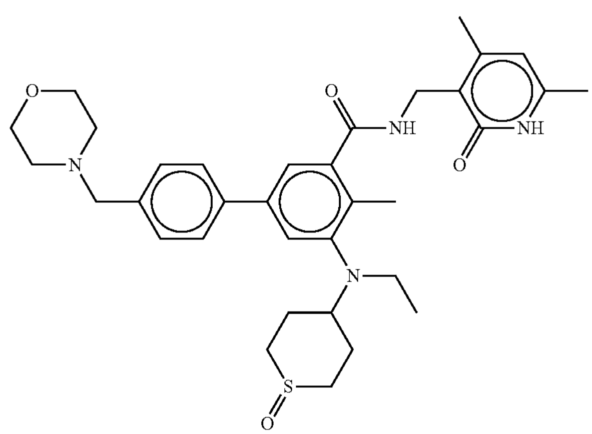 | 605.25 |

TABLE 1-continued

| Compound Number | Structure | MS (M + 1)+ |
|---|---|---|
| 135 | 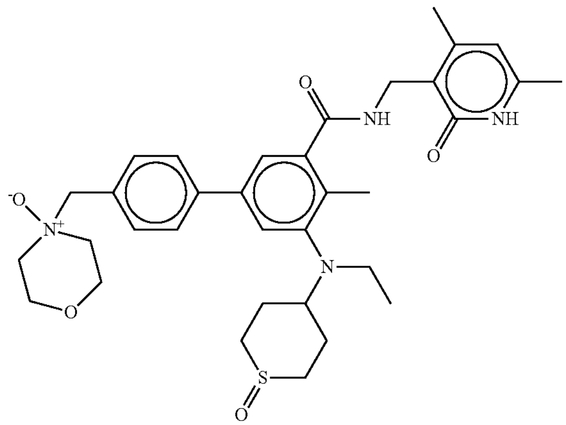 | 621.40 |
| 136 | 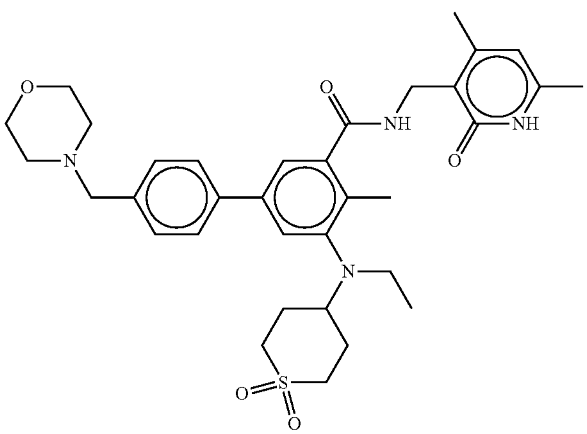 | 621.45 |
| 137 | 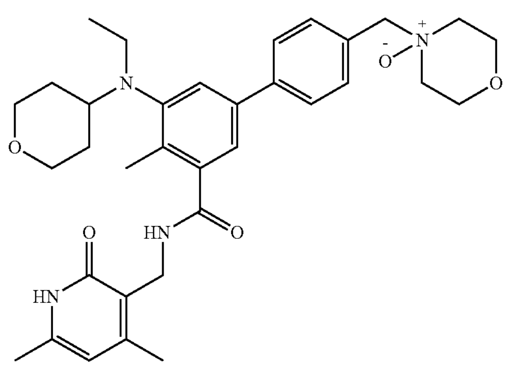 | 589.35 |

TABLE 1-continued

| Compound Number | Structure | MS (M + 1)+ |
|---|---|---|
| 138 | 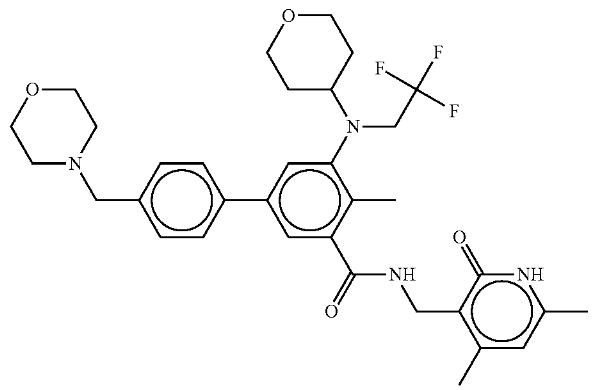 | 627.5 |
| 141 | 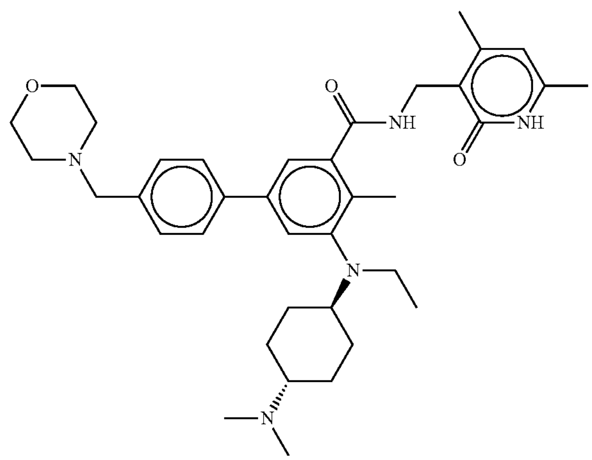 | 614.65 |
| 142 | 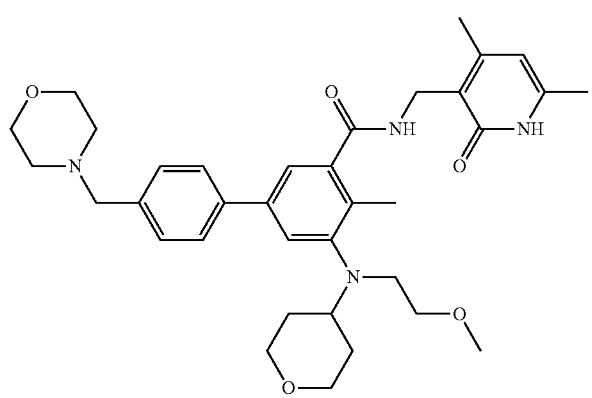 [SMILES: COCCN(c1cc(-c2ccc(CN3CCOCC3)cc2)cc(C(=O)NCc2c(C)cc(C)[nH]c2=O)c1C)C1CCOCC1] | 603.45 |

TABLE 1-continued

| Compound Number | Structure | MS (M + 1)+ |
|---|---|---|
| 143 | 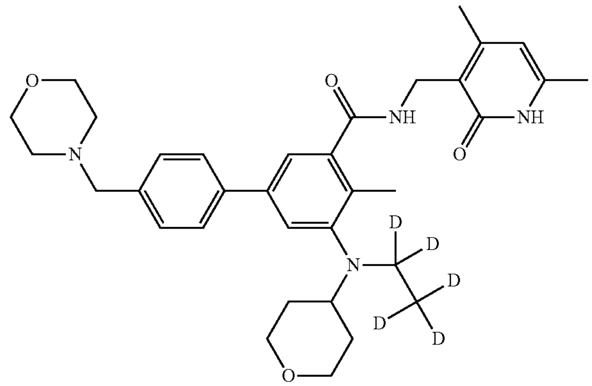 [SMILES: [2H]C([2H])([2H])C([2H])([2H])N(c1cc(-c2ccc(CN3CCOCC3)cc2)cc(C(=O)NCc2c(C)cc(C)[nH]c2=O)c1C)C1CCOCC1] | 578.35 |
| 144 | 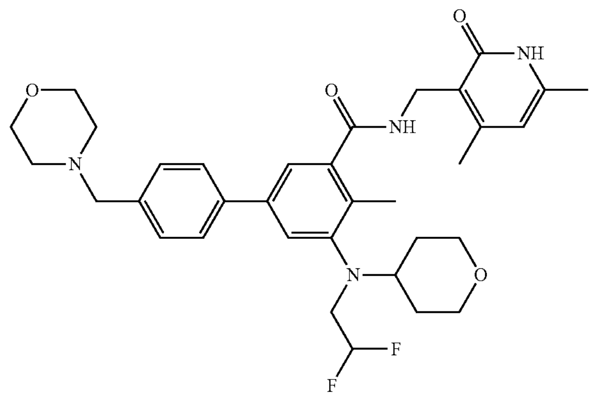 [SMILES: Cc1cc(C)c(CNC(=O)c2cc(-c3ccc(CN4CCOCC4)cc3)cc(N(CC(F)F)C3CCOCC3)c2C)c(=O)[nH]1] | 609.15 |
| 146 | 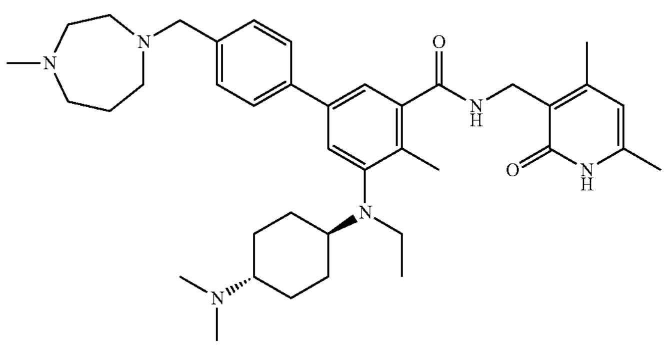 | 641.50 |
| 178 | 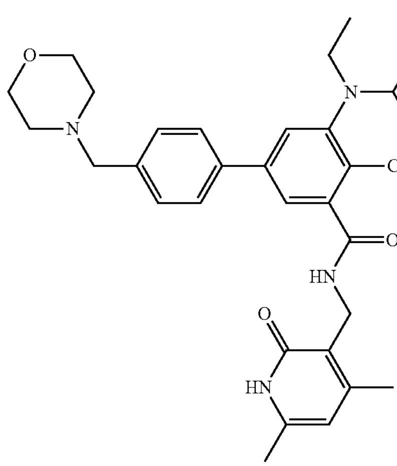 | 593.60 |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or Spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkyl aminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, aryl carbonyloxy, alkoxycarbonyloxy, aryloxycarbonyloxy, carboxylate, alkylcarbonyl, arylcarbonyl, alkoxycarbonyl, aminocarbonyl, alkyl aminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkyl aminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkyl carbonyloxy, aryl carbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and Spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkyl- carbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —NH₂. "Alkylamino" includes groups of compounds wherein nitrogen of —NH₂ is bound to at least one alkyl group. Examples of alkylamino groups include benzylamino, methylamino, ethylamino, phenethylamino, etc. "Dialkylamino" includes groups wherein the nitrogen of —NH₂ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

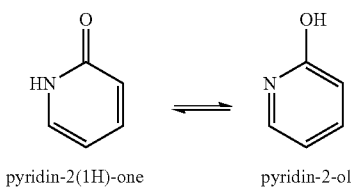 [SMILES: O=c1cccc[nH]1 ; Oc1ccccn1]

pyridin-2(1H)-one        pyridin-2-ol

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of Formula (IIa) disclosed herein include the compounds themselves, as well as their salts, their esters, their solvates, and their prodrugs, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethyl-ammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Examples of prodrugs include esters and other pharmaceutically acceptable derivatives, which, upon administration to a subject, are capable of providing active aryl- or heteroaryl-substituted benzene compounds.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Any compound of Formula (IIa) of the present invention, as described herein, may be an EZH2 inhibitor.

In certain aspects of the invention an inhibitor of EZH2 "selectively inhibits" histone methyltransferase activity of the mutant EZH2 when it inhibits histone methyltransferase activity of the mutant EZH2 more effectively than it inhibits histone methyltransferase activity of wild-type EZH2. For example, in one embodiment the selective inhibitor has an IC50 for the mutant EZH2 that is at least 40 percent lower than the IC50 for wild-type EZH2. In one embodiment the selective inhibitor has an IC50 for the mutant EZH2 that is at least 50 percent lower than the IC50 for wild-type EZH2. In one embodiment the selective inhibitor has an IC50 for the mutant EZH2 that is at least 60 percent lower than the IC50 for wild-type EZH2. In one embodiment the selective inhibitor has an IC50 for the mutant EZH2 that is at least 70 percent lower than the IC50 for wild-type EZH2. In one embodiment the selective inhibitor has an IC50 for the mutant EZH2 that is at least 80 percent lower than the IC50 for wild-type EZH2. In one embodiment the selective inhibitor has an IC50 for the mutant EZH2 that is at least 90 percent lower than the IC50 for wild-type EZH2.

In one embodiment, the selective inhibitor of a mutant EZH2 exerts essentially no inhibitory effect on wild-type EZH2.

In certain aspects of the invention the inhibitor inhibits conversion of H3-K27me2 to H3-K27me3. In one embodiment the inhibitor is said to inhibit trimethylation of H3-K27. Since conversion of H3-K27me1 to H3-K27me2 precedes conversion of H3-K27me2 to H3-K27me3, an inhibitor of conversion of H3-K27me1 to H3-K27me2 naturally also inhibits conversion of H3-K27me2 to H3-K27me3, i.e., it inhibits trimethylation of H3-K27. It is also possible to inhibit conversion of H3-K27me2 to H3-K27me3 without inhibition of conversion of H3-K27me1 to H3-K27me2. Inhibition of this type would also result in inhibition of trimethylation of H3-K27, albeit without inhibition of dimethylation of H3-K27.

In one embodiment the inhibitor inhibits conversion of H3-K27me1 to H3-K27me2 and the conversion of H3-K27me2 to H3-K27me3. Such inhibitor may directly inhibit the conversion of H3-K27me1 to H3-K27me2 alone. Alternatively, such inhibitor may directly inhibit both the conversion of H3-K27me1 to H3-K27me2 and the conversion of H3-K27me2 to H3-K27me3.

In certain aspects of the invention, the inhibitor compound inhibits histone methyltransferase activity. Inhibition of histone methyltransferase activity can be detected using any suitable method. The inhibition can be measured, for example, either in terms of rate of histone methyltransferase activity or as product of histone methyltransferase activity.

The inhibition is a measurable inhibition compared to a suitable control. In one embodiment, inhibition is at least 10 percent inhibition compared to a suitable control. That is, the rate of enzymatic activity or the amount of product with the inhibitor is less than or equal to 90 percent of the corresponding rate or amount made without the inhibitor. In various other embodiments, inhibition is at least 20, 25, 30, 40, 50, 60, 70, 75, 80, 90, or 95 percent inhibition compared to a suitable control. In one embodiment, inhibition is at least 99 percent inhibition compared to a suitable control. That is, the rate of enzymatic activity or the amount of product with the inhibitor is less than or equal to 1 percent of the corresponding rate or amount made without the inhibitor.

A composition of the present invention comprises a compound of Formula (IIa), or a pharmaceutically acceptable salt thereof, and one or more other therapeutic agents, or a pharmaceutically acceptable salt thereof. The present invention provides for the administration of a compound of Formula (IIa) or a pharmaceutically acceptable salt thereof, and one or more therapeutic agents or a pharmaceutically acceptable salt thereof, as a co-formulation or separate formulations, wherein the administration of formulations is simultaneous, sequential, or in alternation. In certain embodiments, the other therapeutic agents can be an agent that is recognized in the art as being useful to treat the disease or condition being treated by the composition of the present invention. In other embodiment, the other therapeutic agent can be an agent that is not recognized in the art as being useful to treat the disease or condition being treated by the composition of the present invention. In one aspect, the other therapeutic agents can be an agent that imparts a beneficial attribute to the composition of the present invention (e.g., an agent that affects the viscosity of the composition). The beneficial attribute to the composition of the present invention includes, but is not limited to, pharmacokinetic or pharmacodynamic co-action resulting from the combination of a compound of Formula (IIa) and one or more other therapeutic agents. For example, the one or more other therapeutic agents can be anticancer agents or chemotherapeutic agents. For example, the one or more other therapeutic agents can be glucocorticoids. For example, the one or more other therapeutic agents can be selected from prednisone, prednisolone, cyclophosphamide, vincristine, doxorubicin, mafosfamide, cisplatin, AraC, everolimus, decitabine, dexamethasone, or functional analogs, derivatives, produgs, and metabolites thereof. In another aspect, the other therapeutic agent can be Prednisone or its active metabolite, Prednisolone.

The therapeutic agents set forth below are for illustrative purposes and not intended to be limiting. The present invention includes at least one other therapeutic agent selected from the lists below. The present invention can include more than one other therapeutic agent, e.g., two, three, four, or five other therapeutic agents such that the composition of the present invention can perform its intended function.

In one embodiment, the other therapeutic agent is an anticancer agent. In one embodiment, the anticancer agent is a compound that affects histone modifications, such as an HDAC inhibitor. In certain embodiments, an anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

In another embodiment, the other therapeutic agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); $thiotepa$ (Thioplex); $bendamustine$ (Treanda); or $streptozocin$ (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar; cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or $mesna$ (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); $gemtuzumab$ (Mylotarg); $eculizumab$ (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); $degarelix$ (Firmagon); $nilutamide$ (Nilandron), $abarelix$ (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepuone (Ixempra); nocodazole; epothilone; $vinorelbine$ (Navelbine); camptothecin (CPT); $irinotecan$ (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary VEGFNEGFR inhibitors include, but are not limited to, bev$_{acizumab}$ (Avastin); $sorafenib$ (Nexavar); $sunitinib$ (Sutent); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); $pegaspargase$ (Oncaspar); $denileukin\ diftitox$ (Ontak), $porfimer$ (Photofrin); $aldesleukin$ (Proleukin); $lenalidomide$ (Revlimid); $bexarotene$ (Targretin); $thalidomide$ (Thalomid); $temsirolimus$ (Torisel); $arsenic\ trioxide$ (Trisenox); $verteporfin$ (Visudyne); mimosine (Leucenol); (1M tegafur-0.4 M 5-chloro-2,4-dihydroxypyrimidine-1 M potassium oxonate), or lovastatin.

In another aspect, the other therapeutic agent is a chemotherapeutic agent or a cytokine such as G-CSF (granulocyte colony stimulating factor).

In yet another aspect, the other therapeutic agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In another aspect, the other therapeutic agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTORJFRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath), $_{gemtuzumab}$ (Mylotarg); $_{temsimlimus}$ (Torisel), $_{pazopanib}$ (Votrient); $_{dasatinib}$ (Sprycel); $_{niotinib}$ (Tasigna), vatalanib (Ptk787; ZK222584); CEP-701; SU5614; MLN518, XL999; VX-322; Azd0530; BMS-354825; SKI-606 CP-690; AG-490; WHI-P154; WHI-P131; AC-220; or AMG888.

The present invention provides methods for combination therapy in which a composition comprising a compound of Formula (IIa) or a pharmaceutically acceptable salt thereof, and one or more other therapeutic agents are administered to a subject in need for treatment of a disease or cancer. The combination therapy can also be administered to cancer cells to inhibit proliferation or induce cell death. In one aspect, a compound of Formula (IIa) or a pharmaceutically acceptable salt thereof is administered prior to administration of the composition of the present invention comprising a compound of Formula (IIa) or a pharmaceutically acceptable salt thereof, and one or more other therapeutic agents. In one aspect, a compound of Formula (IIa) or a pharmaceutically acceptable salt thereof is administered prior to administration of one or more therapeutic agents, such that the other therapeutic agents are administered either in a single composition or in two or more compositions, e.g. administered simultaneously, sequentially, or in alternation.

In one embodiment, a composition of the present invention includes a compound of Formula (IIa) or a pharmaceutically acceptable salt thereof, and one or more anticancer agents, e.g., CHOP (cyclophosphamide, hydroxydaunorubicin, oncovin, and prednisone or prednisolone) or R-CHOP (rituximab, cyclophosphamide, hydroxydaunorubicin, oncovin, prednisone or prednisolone). In one embodiment, a composition of the present invention includes a compound of Formula (IIa) or a pharmaceutically acceptable salt thereof, and prednisone or prednisolone. Methods of the present invention include the combination therapy of administering a compound of Formula (IIa) or a pharmaceutically acceptable salt thereof, and anticancer agents, wherein the anticancer agents are CHOP, R-CHOP, prednisone, or prednisolone.

In certain embodiments, "combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects of the invention, the combination therapies featured in the present invention can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

In certain aspects of the invention "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition of the present invention, or a pharmaceutically acceptable salt, prodrug, metabolite, analog or derivative thereof, may be administered in combination with radiation therapy. Radiation therapy can also be administered in combination with a composition of the present invention and another chemotherapeutic agent described herein as part of a multiple agent therapy.

The present invention also provides pharmaceutical compositions comprising a compound of Formula (IIa) or pharmaceutically acceptable salts thereof, and one or more other therapeutic agent disclosed herein, mixed with pharmaceutically suitable carriers or excipient(s) at doses to treat or prevent a disease or condition as described herein. In one aspect, the present invention also provides pharmaceutical compositions comprising any compound of Table I or pharmaceutically acceptable salts thereof, and one or more therapeutic agents, mixed with pharmaceutically suitable carriers or excipient (s) at doses to treat or prevent a disease or condition as described herein. In another aspect, the present invention also provides pharmaceutical compositions comprising Compound 44

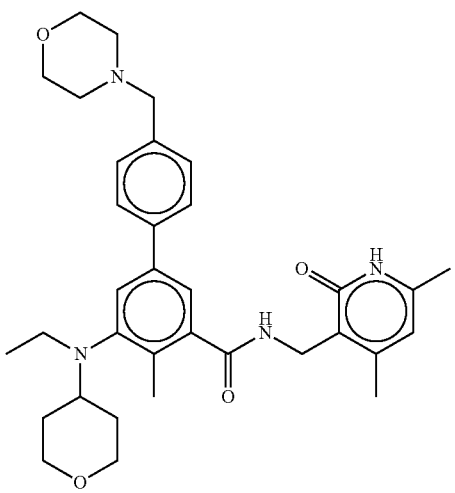

or pharmaceutically acceptable salts thereof, and one or more therapeutic agents, mixed with pharmaceutically suitable carriers or excipient(s) at doses to treat or prevent a disease or condition as described herein. The pharmaceutical compositions of the present invention can also be administered in combination with other therapeutic agents or therapeutic modalities simultaneously, sequentially, or in alternation.

Mixtures of compositions of the present invention can also be administered to the patient as a simple mixture or in suitable formulated pharmaceutical compositions. For example, one aspect of the invention relates to a pharmaceutical composition comprising a therapeutically effective dose of an EZH2 inhibitor of Formula (IIa), or a pharmaceutically acceptable salt, hydrate, enantiomer or stereoisomer thereof; one or more other therapeutic agent, and a pharmaceutically acceptable diluent or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the EZH2 inhibitor compounds described herein, other therapeutic agents described herein, compositions comprising a compound of Formula (IIa) and one or more other therapeutic agents, or the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The composition of the present invention is capable of further forming salts. The composition of the present invention is capable of forming more than one salt per molecule, e.g., mono-, di-, tri-. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The composition of the present invention may also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The composition of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, New York-Oxford (1985).

The composition, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

The present invention provides compositions and methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a composition of the present invention or a pharmaceutically acceptable salt, prodrug, metabolite, polymorph or solvate thereof, to a subject in need of such treatment.

Based at least on the fact that abnormal histone methylation has been found to be associated with certain cancers and precancerous conditions, a method for treating cancer or a precancerous condition with a mutant EZH2 in a subject comprises administering to the subject in need thereof a therapeutically effective amount of a compound that inhibits methylation. In one embodiment a method for treating cancer or a precancerous condition in a subject comprises administering to the subject in need thereof a therapeutically effective amount of a compound that inhibits conversion of unmethylated H3-K27 to monomethylated H3-K27 (H3-K27me1). In one embodiment a method for treating cancer or a precancerous condition in a subject comprises administering to the subject in need thereof a therapeutically effective amount of a compound that inhibits conversion of monomethylated H3-K27 (H3-K27me1) to dimethylated H3-K27 (H3-K27me2). In one embodiment a method for treating cancer or a precancerous condition in a subject comprises administering to the subject in need thereof a therapeutically effective amount of a compound that inhibits conversion of H3-K27me2 to trimethylated H3-K27 (H3-K27me3). In one embodiment a method for treating cancer or a precancerous condition in a subject comprises administering to the subject in need thereof a therapeutically effective amount of a compound that inhibits both conversion of H3-K27me1 to H3-K27me2 and conversion of H3-K27me2 to H3-K27me3. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation.

Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth (cancer).

The disorder in which EZH2-mediated protein methylation plays a part can be cancer, a cell proliferative disorder, or a precancerous condition. The present invention further provides the use of a composition of the present invention, or a pharmaceutically acceptable salt, prodrug, metabolite, polymorph or solvate thereof, to a subject in need of such treatment, for the preparation of a medicament useful for the treatment of cancer. Exemplary cancers that may be treated include lymphomas, including non-Hodgkin lymphoma, follicular lymphoma (FL) and diffuse large B-cell lymphoma (DLBCL); melanoma; and leukemia, including CML. Exemplary precancerous condition includes myelodisplastic syndrome (MDS; formerly known as preleukemia).

In general, compounds that are methylation modulators can be used for modulating cell proliferation, generally. For example, in some cases excessive proliferation may be reduced with agents that decrease methylation, whereas insufficient proliferation may be stimulated with agents that increase methylation. Accordingly, diseases that may be treated by the compounds of the invention include hyperproliferative diseases, such as benign cell growth and malignant cell growth.

As used herein, a "subject in need thereof" is a subject having a disorder in which EZH2-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The subject of the present invention includes any human subject who has been diagnosed with, has symptoms of, or is at risk of developing a cancer or a precancerous condition. The subject of the present invention includes any human subject expressing a mutant EZH2. For example, a mutant EZH2 comprises one or more mutations, wherein the mutation is a substitution, a point mutation, a nonsense mutation, a missense mutation, a deletion, or an insertion or any other EZH2 mutation described herein.

A subject in need thereof may have refractory or resistant cancer. "Refractory or resistant cancer" means cancer that does not respond to treatment. The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH2 histone methyltransferase inhibitors or any other therapeutic agent.

The invention also features a method of selecting a combination therapy for a subject having cancer. The method includes the steps of: detecting one or more EZH2 mutations described herein in a sample from the subject; and selecting, based on the presence of the one or more EZH2 mutations, a combination therapy for treating cancer. In one embodiment, the therapy includes administering to the subject a composition of the invention. In one embodiment, the method further includes administrating to the subject a therapeutically effective amount of a composition of the invention. An EZH2 mutation can be detected using any suitable method known in the art. More methods are described in U.S. patent publication US 20130040906, which is incorporated herein by reference in their entireties.

The methods and uses described herein may include steps of detecting one or more EZH2 mutations described herein in a sample from a subject in need thereof prior to and/or after the administration of a composition of the invention (e.g., a composition comprising a compound of Formula (IIa) or pharmaceutically acceptable salts thereof, and one or more therapeutic agents) to the subject. The presence of the one or more EZH2 mutations described herein in the tested sample indicates the subject is responsive to the combination therapy of the invention.

The present invention provides personalized medicine, treatment and/or cancer management for a subject by genetic screening of one or more EZH2 mutations described herein in the subject. For example, the present invention provides methods for treating or alleviating a symptom of cancer or a precancerous condition in a subject in need thereof by determining responsiveness of the subject to a combination therapy and when the subject is responsive to the combination therapy, administering to the subject a composition of the invention. The responsiveness is determined by obtaining a sample from the subject and detecting one or more EZH2 mutations described herein, and the presence of such one or more EZH2 mutations described herein indicates that the subject is responsive to the composition of the invention. Once the responsiveness of a subject is determined, a therapeutically effective amount of a composition, for example, a composition comprising a compound of Formula (IIa) or pharmaceutically acceptable salts thereof, and one or more therapeutic agents, can be administered. The therapeutically effective amount of a composition can be determined by one of ordinary skill in the art.

As used herein, the term "responsiveness" is interchangeable with terms "responsive", "sensitive", and "sensitivity", and it is meant that a subject is showing therapeutic responses when administered a composition of the invention, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the invention, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of TO or Tis; and where the regional lymph nodes (N) have been assigned a stage of NO; and where distant metastasis (M) has been assigned a stage of MO.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph, or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, ester, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, ester, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, ester, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A composition of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

The disorder in which EZH2-mediated protein methylation plays a part can be a neurological disease. The compound of this invention can thus also be used for treating neurologic diseases such as epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease m (MJD; SCA3), Spinocerebellar Ataxia 6 (SCA6), Spinocerebellar Ataxia 7 (SCAT), and Spinocerebellar Ataxia 12 (SCA12).

Any other disease in which epigenetic methylation, which is mediated by EZH2, plays a role may be treatable or preventable using compositions and methods described herein.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition of the present invention, e.g., a composition comprising any compound of Formula (IIa) or pharmaceutically acceptable salt thereof, and one or more other therapeutic agents, such as prednisone, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A composition of the present invention does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the IC5o, i.e., a 50% inhibition, for a molecular target of interest.

Administering a composition of the present invention to a cell or a subject in need thereof can result in modulation (i.e., stimulation or inhibition) of an activity of a protein methyltransferase of interest.

Administering a compound of the present invention, e.g., a composition comprising any compound of Formula (IIa) or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci U.S.A.* 100(5): 2674-8, 2003. In an aspect, cell death occurs by apoptosis.

Preferably, an effective amount of a composition of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a composition of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a composition of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a composition of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a composition of the present invention, or a pharmaceutically acceptable salt, prodrug, metabolite, polymorph or solvate thereof, to a subject in need thereof, where administration of the composition of the present invention, or a pharmaceutically acceptable salt, prodrug, metabolite, polymorph or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{th}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

Example 1: Synthesis of N-((4,6-dimethyl-2-oxo-1, 2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide

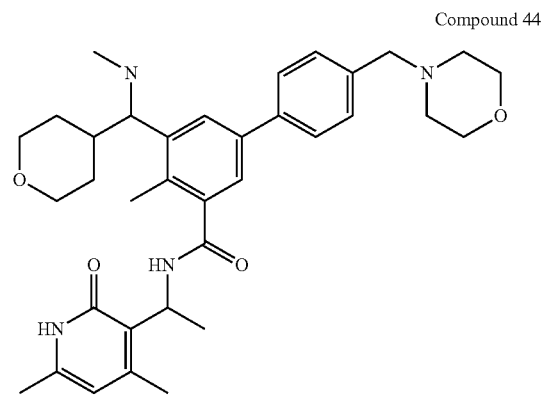 [SMILES: CNC(c1cc(-c2ccc(CN3CCOCC3)cc2)cc(C(=O)NC(C)c2c(C)cc(C)[nH]c2=O)c1C)C1CCOCC1]

Compound 44

Step 1: Synthesis of 5-bromo-2-methyl-3-nitrobenzoic acid

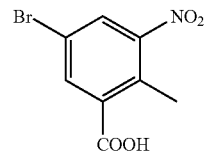

To stirred solution of 2-methyl-3-nitrobenzoic acid (100 g, 552 mmol) in conc. H$_2$SO$_4$ (400 mL), 1,3-dibromo-5,5-dimethyl-2,4-imidazolidinedione (88 g, 308 mmol) was added in a portion wise manner at room temperature and the reaction mixture was then stirred at room temperature for 5 h. The reaction mixture was poured onto ice cold water, the precipitated solid was filtered off, washed with water and dried under vacuum to afford the desired compound as a solid (140 g, 98%). The isolated compound was taken directly into the next step. $^1$H NMR (DMSO-d$_6$, 400 MHz) δ 8.31 (s, 1H), 8.17 (s, 1H), 2.43 (s, 3H).

Step 2: Synthesis of methyl 5-bromo-2-methyl-3-nitrobenzoate

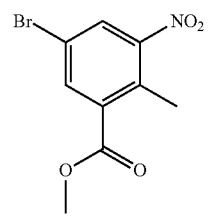

To a stirred solution of 5-bromo-2-methyl-3-nitrobenzoic acid (285 g, 1105 mmol) in DMF (2.8 L) at room temperature was added sodium carbonate (468 g, 4415 mmol) followed by addition of methyl iodide (626.6 g, 4415 mmol). The resulting reaction mixture was heated at 60° C. for 8 h. After completion (monitored by TLC), the reaction mixture was filtered (to remove sodium carbonate) and washed with ethyl acetate (1L×3). The combined filtrate was washed with water (3L×5) and the aqueous phase was back extracted with ethyl acetate (1L×3). The combined organic layers were dried over anhydrous sodium sulfate, filtered and concentrated under reduced pressure to afford the title compound as a solid (290 g, 97% yield). The isolated compound was taken directly into the next step. $^1$H NMR (CDCl$_3$, 400 MHz) δ 8.17 (s, 1H), 7.91 (s, 1H), 3.96 (s, 3H), 2.59 (s, 3H).

Step 3: Synthesis of methyl 3-amino-5-bromo-2-methylbenzoate

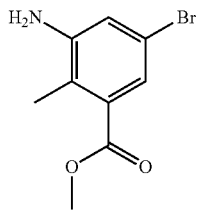

To a stirred solution of methyl 5-bromo-2-methyl-3-nitrobenzoate (290 g, 1058 mmol) in ethanol (1.5 L) was added aqueous ammonium chloride (283 g, 5290 mmol dissolved in 1.5 L water). The resulting mixture was stirred at 80° C. to which iron powder (472 g, 8451 mmol) was added in a portion wise manner. The resulting reaction mixture was heated at 80° C. for 12 h. Upon completion as determined by TLC, the reaction mixture was hot filtered over Celite® and the celite bed was washed with methanol (5 L) followed by washing with 30% MeOH in DCM (5 L). The combined filtrate was concentrated in-vacuo, the residue obtained was diluted with aqueous sodium bicarbonate solution (2 L) and extracted with ethyl acetate (5L×3). The combined organic layers were dried over anhydrous sodium sulfate, filtered and concentrated under reduced pressure to afford the title compound as a solid (220 g, 85%). The compound was taken directly into the next step. $^1$H NMR (CDCl$_3$, 400 MHz) δ 7.37 (s, 1H), 6.92 (s, 1H), 3.94 (s, 3H), 3.80 (bs, 2H), 2.31 (s, 3H).

Step 4: Synthesis of methyl 5-bromo-2-methyl-3-((tetrahydro-2H-pyran-4-yl) amino) benzoate

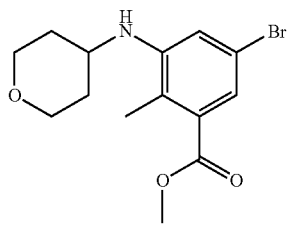 [SMILES: COC(=O)c1cc(Br)cc(NC2CCOCC2)c1C]

To a stirred solution of methyl 3-amino-5-bromo-2-methylbenzoate (15 g, 61.5 mmol) and dihydro-2H-pyran-4(3)-one (9.2 g, 92 mmol) in dichloroethane (300 mL) was added acetic acid (22 g, 369 mmol) and the reaction mixture stirred at room temperature for 15 minutes, then the reaction mixture was cooled to 0° C. and sodium triacetoxyborohydride (39 g, 184 mmol) was added. The reaction mixture was stirred overnight at room temperature. Upon completion of the reaction as determined by TLC, aqueous sodium bicarbonate solution was added to the reaction mixture until a pH of 7-8 was obtained. The organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the desired compound as a solid (14 g, 69%). $^1$H NMR (DMSO-d$_6$, 400 MHz) δ 7.01 (s, 1H), 6.98 (s, 1H), 5.00 (d, 1H, J=7.6 Hz), 3.84-3.87 (m, 2H), 3.79 (s, 3H), 3.54-3.56 (m, 1H), 3.43 (t, 2H, J=12 Hz), 2.14 (s, 3H), 1.81-1.84 (m, 2H), 1.47-1.55 (m, 2H).

Step 5: Synthesis of methyl 5-bromo-3-(ethyl (tetrahydro-2H-pyran-4-yl) amino)-2-methylbenzoate

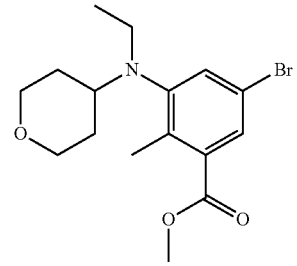 [SMILES: CCN(c1cc(Br)cc(C(=O)OC)c1C)C1CCOCC1]

To a stirred solution of methyl 5-bromo-2-methyl-3-((tetrahydro-2H-pyran-4-yl) amino) benzoate (14 g, 42.7 mmol) in dichloroethane (150 mL) was added acetaldehyde (3.75 g, 85.2 mmol) and acetic acid (15.3 g, 256 mmol). The resulting reaction mixture was stirred at room temperature for 15 minutes. The mixture was cooled to 0° C. and sodium triacetoxyborohydride (27 g, 128 mmol) was added. The reaction mixture was stirred at room temperature for 3 hours. Upon completion of the reaction as determined by TLC, aqueous sodium bicarbonate solution was added to the reaction mixture until a pH 7-8 was obtained, the organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the desired compound as a viscous liquid (14 g, 93%). $^1$H NMR (DMSO-d$_6$, 400 MHz) δ 7.62 (s, 1H), 7.52 (s, 1H), 3.80 (bs, 5H), 3.31 (t, 2H), 2.97-3.05 (m, 2H), 2.87-2.96 (m, 1H), 2.38 (s, 3H), 1.52-1.61 (m, 2H), 1.37-1.50 (m, 2H), 0.87 (t, 3H, J=6.8 Hz).

Step 6: Synthesis of 5-bromo-N-((4, 6-dimethyl-2-oxo-1, 2-dihydropyridin-3-yl) methyl)-3-(ethyl (tetrahydro-2H-pyran-4-yl) amino)-2-methylbenzamide

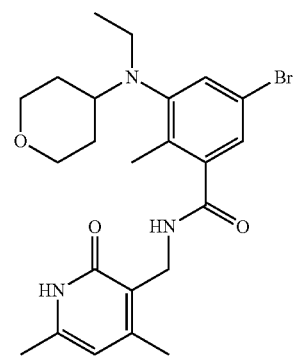 [SMILES: CCN(c1cc(Br)cc(C(=O)NCc2c(C)cc(C)[nH]c2=O)c1C)C1CCOCC1]

To a stirred solution of 5-bromo-3-(ethyl (tetrahydro-2H-pyran-4-yl) amino)-2-methylbenzoate (14 g, 39.4 mmol) in ethanol (100 mL) was added aqueous NaOH (2.36 g, 59.2 mmol in 25 mL water) and the resulting mixture was stirred at 60° C. for 1 h. Upon completion of the reaction as determined by TLC, the solvent was removed under reduced pressure and the residue obtained was acidified with 1N HCl until a pH 7 was obtained and then aqueous citric acid solution was added until a pH 5-6 was obtained. The aqueous layer was extracted with 10% MeOH in DCM (200 mL×3), the combined organic layers were dried over anhydrous sodium sulfate, filtered and concentrated under reduced pressure to give the respective acid (14 g, 100%).

The above acid (14 g, 40.9 mmol) was then dissolved in DMSO (70 mL) and 3-(amino methyl)-4, 6-dimethylpyridin-2(1H)-one (12.4 g, 81.9 mmol) was added to it. The reaction mixture was stirred at room temperature for 15 minutes, then PYBOP (31.9 g, 61.4 mmol) was added and stirring was continued for overnight at room temperature. Upon completion of the reaction as determined by TLC, the reaction mixture was poured onto ice-cold water (700 mL), stirred for 30 minutes and the precipitated solid was collected by filtration, washed with water (500 mL) and air dried. The solid obtained was stirred with acetonitrile (75 mL×2), filtered and air dried. The solid obtained was again stirred with 5% MeOH in DCM (100 mL), filtered and dried completely under vacuum to afford the title compound as a solid (14 g, 74%). $^1$H NMR (DMSO-$d_6$, 400 MHz) δ 11.47 (s, 1H), 8.23 (t, 1H), 7.30 (s, 1H), 7.08 (s, 1H), 5.85 (s, 1H), 4.23 (d, 2H, J=4.4 Hz), 3.81 (d, 2H, J=10.4 Hz), 3.20-3.26 (m, 2H), 3.00-3.07 (m, 1H), 2.91-2.96 (m, 2H), 2.18 (s, 3H), 2.14 (s, 3H), 2.10 (s, 3H), 1.58-1.60 (m, 2H), 1.45-1.50 (m, 2H), 0.78 (t, 3H, J=6.8 Hz).

Step 7: Synthesis of N-((4, 6-dimethyl-2-oxo-1, 2-dihydropyridin-3-yl) methyl)-5-(ethyl (tetrahydro-2H-pyran-4-yl) amino)-4-methyl-4'-(morpholinomethyl)-[1,1'-biphenyl]-3-carboxamide

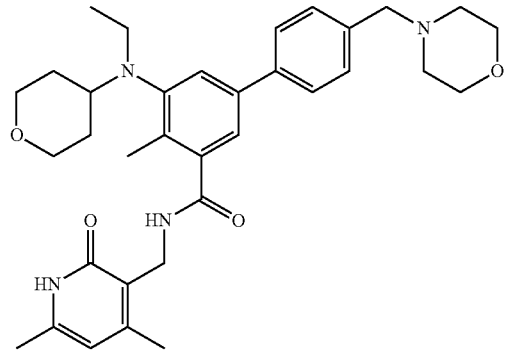

To a stirred solution of 5-bromo-N-((4, 6-dimethyl-2-oxo-1, 2-dihydropyridin-3-yl) methyl)-3-(ethyl (tetrahydro-2H-pyran-4-yl) amino)-2-methylbenzamide (14 g, 29.5 mmol) in dioxane/water mixture (70 mL/14 mL) was added 4-(4-(4, 4, 5, 5-tetramethyl-1, 3, 2-dioxaborolan-2-yl) benzyl) morpholine (13.4 g, 44.2 mmol) followed by addition of $Na_2CO_3$ (11.2 g, 106.1 mmol). The solution was purged with argon for 15 minutes and then Pd (PPh$_3$)$_4$ (3.40 g, 2.94 mmol) was added and the solution was again purged with argon for a further 10 min. The reaction mixture was heated at 100° C. for 4 h. After completion (monitored by TLC), the reaction mixture was diluted with water and extracted with 10% MeOH/DCM. The combined organic layers were dried over anhydrous sodium sulphate, filtered and concentrated under reduced pressure. The crude compound was purified by column chromatography (100-200 mesh silica gel) eluting with methanol: DCM to the title compound as a solid (12 g, 71%). Analytical Data: LCMS: 573.35 (M+1)$^+$; HPLC: 99.5% (@ 254 nm) (R$_t$; 3.999; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.19 (t, 1H), 7.57 (d, 2H, J=7.2 Hz), 7.36-7.39 (m, 3H), 7.21 (s, 1H), 5.85 (s, 1H), 4.28 (d, 2H, J=2.8 Hz), 3.82 (d, 2H, J=9.6 Hz), 3.57 (bs, 4H), 3.48 (s, 2H), 3.24 (t, 2H, J=10.8 Hz), 3.07-3.09 (m, 2H), 3.01 (m, 1H), 2.36 (m, 4H), 2.24 (s, 3H), 2.20 (s, 3H), 2.10 (s, 3H), 1.64-1.67 (m, 2H), 1.51-1.53 (m, 2H), 0.83 (t, 3H, J=6.4 Hz).

Step 8: Synthesis of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide trihydrochloride

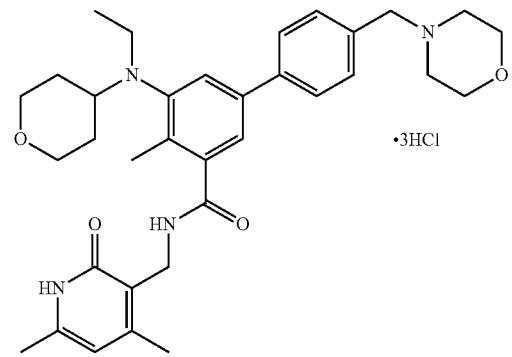 [SMILES: CCN(c1cc(-c2ccc(CN3CCOCC3)cc2)cc(C(=O)NCc2c(C)cc(C)[nH]c2=O)c1C)C1CCOCC1]

N-((4, 6-dimethyl-2-oxo-1, 2-dihydropyridin-3-yl) methyl)-5-(ethyl (tetrahydro-2H-pyran-4-yl) amino)-4-methyl-4'-(morpholinomethyl)-[1,1'-biphenyl]-3-carboxamide (12 g, 21.0 mmol) was dissolved in methanolic HCl (200 mL) and stirred at room temperature for 3 h. After three hours of stirring, the reaction mixture was concentrated under reduced pressure. The solid obtained was stirred with ether (100 mL×2) to afford the desired salt as a solid (11 g, 77%). Analytical Data of the tri-HCl salt: LCMS: 573.40 (M+1)$^+$; HPLC: 99.1% (@ 254 nm) (R$_t$; 3.961; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); NMR (D$_2$O 400 MHz) δ 7.92 (bs, 1H,) 7.80 (s, 1H), 7.77 (d, 2H, J=8 Hz), 7.63 (s, 1H), 7.61 (s, 1H), 6.30 (s, 1H), 4.48 (s, 2H), 4.42 (s, 2H), 4.09-4.11 (m, 4H), 3.95-3.97 (m, 2H), 3.77 (t, 3H, J=10.4 Hz), 3.44-3.47 (m, 3H), 3.24-3.32 (m, 3H), 2.42 (s, 3H), 2.35 (s, 3H), 2.26 (s, 3H), 2.01 (m, 2H), 1.76 (m, 2H), 1.04 (t, 3H, J=6.8 Hz).

Example 2: Combination Therapy of Compound 44 and CHOP Components

The human lymphoma cell lines WSU-DLCL2 (DSMZ; ACC 575), OCI-Ly19 (DSMZ; ACC 528), RL (ATCC;

CRL-2261) were obtained from the indicated sources and maintained in RPMI-1640 medium supplemented with 10% fetal bovine serum and 2 mM glutamine. The cells were cultured in tissue culture flasks in a humidified incubator at 37° C., in an atmosphere of 5% $CO_2$ and 95% air.

The effect of combination therapy of Compound 44 with each individual CHOP (Cyclophosphamide, Vincristine, Doxorubicin, and Prednisolone) component on cancer cell viability was investigated in vitro. The dosage schedule is depicted in FIG. 1A. WSU-DLCL2 human lymphoma cells were treated with increasing concentrations of Compound 44. After 4 days, a combination of increasing concentrations of Compound 44 and each CHOP component were administered to the cells. After 4 days, cell viability was determined using Millipore Guava ViaCount Reagent and flow cytometry analysis. The percentage of viable cells for each sample was normalized to the percentage of viable cells for the DMSO-treated samples within each Compound 44 concentration group.

Cells treated with Compound 44 and CHOP components alone showed a decrease in cell viability. Cells treated with Compound 44 with Mafofsamide (Cyclophosphamide metabolite) (FIG. 2A) and Doxorubicin (FIG. 2B) did not exhibit reduced cell viability at increasing concentrations of Mafofsamide or Doxorubicin. Combination therapy of Compound 44 with Vincristine (FIG. 2C) showed reduced cell viability at the highest concentration Compound 44. Importantly, combination therapy utilizing Compound 44 and Prednisolone (Prednisone metabolite) (FIG. 2D) showed synergistic reduction in cell viability at the 2 highest doses of Compound 44 and all doses of Prednisolone.

Example 3: Synergistic Effects of Compound 44 and Prednisolone Combination Therapy is Dependent on Dosage Schedule To investigate the role of the timing of administration of Compound 44 and Prednisolone on cell viability, WSU-DLCL2 cells were treated with different dosing schedules, as depicted in FIG. 1. Cell viability was determined by staining with Millipore Guava ViaCount Reagent and then analyzed by flow cytometry.

Administration of Compound 44 prior to co-administration of Compound 44 and Prednisolone resulted in reduced cell viability (FIG. 3A). Cells treated as depicted in FIG. 1A. Cell viability was normalized to the DMSO/DMSO sample, thereby revealing the effect of treatment with Compound 44 alone. Increasing concentrations of Compound 44 resulted in a reduction of cell growth. Importantly, increasing concentrations of Prednisolone in combination with Compound 44 resulted in additional reduction of cell growth compared to treating the cells with Compound 44 or Prednisolone independently as single agents. Therefore, combination therapy of Compound 44 and Prednisolone, wherein Compound 44 is administered first causes a synergistic effect of reducing cancer cell viability.

Administration of Compound 44 prior to administration of Prednisolone resulted in reduced cell viability (FIG. 3B). Cells were treated as depicted in FIG. 1B Cell viability was normalized to the DMSO-treated sample for each Compound 44 concentration group. Treatment with increasing concentrations of Prednisolone as a single agent after a prior administration of Compound 44 also resulted in additional reduction of cell viability when compared to cells treated with Prednisolone alone, thereby demonstrating the synergistic effect of combination therapy with Compound 44 and Prednisolone.

Administration of Prednisone prior to co-administration of Compound 44 and Prednisolone did not reduce cell viability (FIG. 3C). Cells were treated as depicted in FIG. 1C. Cell viability was normalized to the DMSO-treated sample for each Compound 44 concentration group. These results demonstrated that administration of Prednisolone prior to treatment with a composition comprising Compound 44 and Prednisolone did not cause a synergistic effect on cell viability.

These data clearly show that the combination therapy of Compound 44 and Prednisolone decreases cancer cell viability or induces cancer cell death. Specifically, combination therapy wherein the cells are treated with Compound 44 prior to treatment with Prednisolone or a combination of Prenisolone and Compound 44 results in a synergistic effect on cell viability, wherein the reduction of cell viability is greater than that induced by treatment of either Prednisolone or Compound 44 as single agents.

Example 4: Compound 44 and Prednisolone Syngery is Dependent on EZH2 Mutation

Different human lymphoma cancer cell lines harboring different EZH2 mutations were analyzed for their responsiveness to Compound 44 and Prednisolone. Cells were treated with dosing schedules as in FIG. 1A, where cells are first treated with Compound 44, and then after 4 days, are treated with a combination of Compound 44 and Prednisolone. Cell viability was determined 4 days later using Millipore Guava ViaCount reagent and flow cytometry analysis. Percentage of cell viability was normalized to percentage of the DMSO-treated sample.

Lymphoma cells expressing wild-type (WT) EZH2, OCI-LY19 cell line, are resistant to treatment with EZH2 inhibitors. Accordingly, treatment with increasing concentrations of Compound 44 does not affect cell viability. Increasing concentrations of Prednisolone does not have an additional or synergistic effect on cell viability (FIG. 4A).

WSU-DLCL2 cells harboring an Y641F mutation are sensitive to treatment with EZH2 inhibitors, as evidenced by a decrease in cell viability at increasing concentrations of Compound 44 when administered as a single agent. Moreover, when treated in combination with Prednisolone, the cells exhibit reduced cell viability (FIG. 4B).

RL cells harbor an Y641N mutation and are resistant to EZH2 inhibitor treatment. Administration of increasing concentrations of Compound 44 alone does not result in a reduction in cell viability. However, co-administration of Compound 44 with Prednisolone resulted in a synergistic effect, wherein the cell viability was decreased greater than that observed when Compound 44 and Prednisolone are administered as single agents (FIG. 4C).

Taken together, these results suggest that combination therapy with Compound 44 and Prednisolone may result in a synergistic effect in reducing cancer cell viability and increasing cancer cell death in cells that express a mutant EZH2. Moreover, cells that are resistant to either drug, Compound 44 or Prednisolone, when administered as a single agent, become sensitive to the combination treatment and cell viability is reduced.

Example 5: Pharmacokinetic Analysis of Compound 44 and CHOP Components Co-Administration In Vivo Pharmacokinetic analysis of Compound 44 in combination with each of the CHOP components (Cyclophosphamide, Vincristine, Doxorubicin, and Prednisolone) was performed to determine the absorption or distribution of Compound 44 in vivo. Male BALB/c between 8-12 weeks old and weighing 20-40 g were obtained from In vivo, Bengaluru, India. Animals were administered one of the CHOP components as a single agent, or in combination with Compound 44. Cyclophosphamide was administered by intraperitoneal injection at 30 mg/kg. Vincristine was administered by intravenous injection at 0.375 mg/kg. Doxorubicin was administered by intravenous injection at 2.475 mg/kg. Prednisolone was administered by oral administration at 0.15 mg/kg. Compound 44 was administered at 225 mg/kg by oral administration. Plasma samples were taken at various timepoints over a course of 24 hours after administration.

The extraction procedure for plasma study samples or the spiked plasma calibration standards were identical: A 25 µL sample of either study sample or spiked calibration standard was added to individual pre-labeled micro-centrifuge tubes. A volume of 100 µL of IS (Glipizide, 500 ng/mL) prepared in ACN was then added to the micro-centrifuge tubes except in blank sample where acetonitrile was added and vortexed for 5 minutes. Samples were centrifuged for 10 minutes at the speed of 15000 rpm (20600 g) at 4° C. Following centrifugation, 100 µL of the supernatant was sampled from each centrifuge tube and transferred into insert vials. These vials were loaded in auto-sampler for the LC/MS/MS analysis. Calibration standards were prepared by spiking 10 µL of analyte (Compound 44, Cyclophosphamide, Doxorubicin, Vincristine and Prednisolone) in 190 µL of blank mouse plasma.

NonCompartmental-Analysis module in WinNonlin® (Version 5.2) was used to assess the pharmacokinetic parameters. The areas under the concentration time curve (AUC) were calculated by linear trapezoidal rule. The ratio ($AUC_{combo}/AUC_{single}$) of AUC for combination therapy of Compound 44 with each component of CHOP ($AUC_{combo}$) to AUC of each CHOP component alone ($AUC_{single}$) and indicated similar bioavailability when CHOP components were administered alone or with Compound 44.

Example 6: Analysis of Compound 44 and CHOP Combination Therapy in Mouse Xenograft Models Mice Female Fox Chase SCID® Mice (CB17/Icr-Prkdc$_{scid}$/IcrIcoCrl, Charles River Laboratories) or athymic nude mice (Crl:NU(Ncr)-Foxn1$_{nu}$, Charles River Laboratories) were 8 weeks old and had a body-weight (BW) range of 16.0-21.1 g on day 1 of the study. The animals were fed ad libitum water (reverse osmosis 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity. All procedures comply with the recommendations of the Guide for Care and Use of Laboratory Animals with respect to restraint, husbandry, surgical procedures, feed and fluid regulation, and veterinary care.

Tumor Cell Culture

Human lymphoma cell lines line were obtained from different sources (ATCC, DSMZ) and maintained at Piedmont as suspension cultures in RPMI-1640 medium containing 100 units/mL penicillin G sodium salt, 100 g/mL streptomycin, and 25 g/mL gentamicin. The medium was supplemented with 10% fetal bovine serum and 2 mM glutamine. The cells were cultured in tissue culture flasks in a humidified incubator at 37° C., in an atmosphere of 5% $CO_2$ and 95% air.

In Vivo Tumor Implantation

Human lymphoma cell lines were harvested during mid-log phase growth, and resuspended in PBS with 50% Matrigel™ (BD Biosciences). Each mouse received $1 \times 10^7$ cells (0.2 mL cell suspension) subcutaneously in the right flank. Tumors were calipered in two dimensions to monitor growth as the mean volume approached the desired 80-120 mm³ range. Tumor size, in mm³, was calculated from:

$$\text{Tumor volume} = \frac{w^2 \times l}{2}$$

where w=width and l=length, in mm, of the tumor. Tumor weight can be estimated with the assumption that 1 mg is equivalent to 1 mm³ of tumor volume. After 10-30 days (depending on the cell line used) mice with 108-126 mm³ tumors were sorted into treatment groups with mean tumor volumes of 117-119 mm³.

Test Articles

Compounds of Formula (IIa) were stored at room temperature and protected from light. On each treatment day, a fresh compound formulations were prepared by suspending the powders in 0.5% sodium carboxymethylcellulose (NaCMC) and 0.1% Tween®80 in deionized water. The Compound 44 vehicle, 0.5% NaCMC and 0.1% Tween® 80 in deionized water, was used to treat the control groups at the same schedules. Formulations were stored away from light at 4° C. prior to administration.

Several chemotherapeutica were used in parallel to Epizyme compounds. Cyclophosphamide (Baxter, Lot #016591), was reconstituted to 20 mg/mL with sterile saline and stored at 4° C. A fresh dosing solution was prepared for each dose by dilution with saline. Doxorubicin (Doxorubicin Meiji®, Meiji Pharmaceutical Co. Ltd., 1 mg/mL) was stored at 4° C. and diluted with saline on each treatment day. Vincristine (Hospira, Inc., 1 mg/mL) was diluted with saline on each treatment day. Prednisone (Boehringer Ingelheim GmbH, 1 mg/mL) was diluted with PBS at the beginning of each 5-day dosing cycle.

Treatment Plan

Mice were treated at compound doses ranging from 75-600 mg/kg and at TID (3 times a day every 8 h), BID (twice a day every 12 h) or QD (once a day) schedules for various amount of days days by oral gavage or injections via the intravenous, intraperitoneal or subcutaneous routes. Each dose was delivered in a volume of 0.2 mL/20 g mouse (10 mL/kg), and adjusted for the last recorded weight of individual animals. The maximal treatment length was 28 days.

Median Tumor Volume (MTV) and Tumor Growth Inhibition (TGI) Analysis

Treatment efficacy was determined on the last treatment day. MTV(n), the median tumor volume for the number of animals, n, evaluable on the last day, was determined for each group. Percent tumor growth inhibition (% TGI) can be defined several ways. First, the difference between the MTV(n) of the designated control group and the MTV(n) of the drug-treated group is expressed as a percentage of the MTV(n) of the control group:

$$\% \ TGI = \left( \frac{MTV(n)_{control} - MTV(n)_{treated}}{MTV(n)_{control}} \right) \times 100$$

Another way of calculating % TGI is taking the change of the tumor size from day 1 to day n into account with n being the last treatment day.

$$\% \ TGI = \left(\frac{\Delta MTV_{control} - \Delta MTV_{treated}}{\Delta MTV_{control}}\right) \times 100$$

$$\Delta MTV_{control} = MTV(n)_{control} - MTV(1)_{control}$$

$$\Delta MTV_{treated} = MTV(n)_{treated} - MTV(1)_{treated}$$

Tumor Growth Delay Analysis

Alternatively, mice were kept alive after the last treatment day for tumor growth delay analysis. Tumors were callipered twice-weekly and each test animal was euthanized when its neoplasm reached the endpoint volume of 2000 mm³ or on the pre-specified last day of the study, whichever came first. The time-to-endpoint (TTE) for each mouse was calculated from the following equation:

$$TTE(\text{days}) = \frac{\log_{10}(endpoint \ \text{volume, mm}^3) - b}{m}$$

where b is the intercept and m is the slope of the line obtained by linear regression of a log-transformed tumor growth data set. The data sets were composed of the first observation that exceeded the study endpoint volume and the three consecutive observations that immediately preceded the attainment of the endpoint volume. Animals that did not reach the volume endpoint were assigned a TTE value equal to the last day of the study (prespecified). Any animal classified as a treatment-related (TR) death was to be assigned a TTE value equal to the day of death. Any animal classified as a nontreatment-related (NTR) death was excluded from TTE calculations and all further analyses.

Treatment outcome was determined from tumor growth delay (TGD), defined as the increase in the median TTE in a treatment group compared to the control group:

$$TGD = T - C$$

expressed in days, or as a percentage of the median TTE of the control group:

$$\% \ TGD = \frac{T - C}{C} \times 100$$

where:
T=median TTE for a treatment group
C=median TTE for the control group
Toxicity Animals were weighed daily on Days 1-5, and then twice weekly until the completion of the study. The mice were examined frequently for overt signs of any adverse, treatment related side effects, which were documented. Acceptable toxicity for the maximum tolerated dose (MTD) was defined as a group mean BW loss of less than 20% during the test, and not more than 10% mortality due to TR deaths. A death was to be classified as TR if it was attributable to treatment side effects as evidenced by clinical signs and/or necropsy, or due to unknown causes during the dosing period. A death was to be classified as NTR if there was evidence that the death was unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On several days during the study mice were sampled in a pre-specified fashion. Sampling included non-terminal bleeds (0.25 mL) from the mandibular vein without anesthesia and full volume blood collection via terminal cardiac puncture under $CO_2$ anesthesia. Blood samples were processed for plasma, with K2-EDTA as anti-coagulant. The plasma samples were frozen at −80° C. and stored prior to bioanalysis of compound levels.

Tumors were harvested from specified mice under RNAse free conditions and bisected. A 2 mm thick slice from one half of each tumor was formalin-fixed for 24 h and transferred to 70% ethanol. The fixed tumor tissues were paraffin embedded. The remaining tumor tissue from each animal was snap frozen in liquid $N_2$ and pulverized with a mortar and pestle.

Specified mice were sampled for the surrogate tissues including spleen, skin, bone marrow, and whiskers. Each tissue was isolated and fixed and/or snap frozen.

Statistical and Graphical Analyses

All statistical and graphical analyses were performed with Prism 3.03 (GraphPad) for Windows. Several analyses methods were applied. Median D29 tumor volumes were compared with the Kruskal-Wallis test, and a post hoc Dunn's multiple comparison test. These tests were performed three times.

The two-tailed statistical analyses were conducted at P=0.05. Prism reports results as non-significant (ns) at P>0.05, significant (symbolized by "*") at 0.01<P<0.05, very significant ("") at 0.001<P<0.01 and extremely significant ("*") at P>0.001.

To test statistical significance between the control and treated groups over the whole treatment time course either a Repeated measures ANOVA test followed by Dunnets multiple comparison post test or a 2 way ANOVA test were employed.

For graphical representations s "box and whiskers" diagram was constructed to show the distribution of individual tumor volumes for each group. The box represents the $25_{th}$ to $75_{th}$ percentile of observations, the horizontal line corresponds to the median value, and the "whiskers" indicate the maximum and minimum values. Median or mean (±SEM) tumor volumes were graphed on a semilog or linear plot as functions of time. Group mean BW changes during the study were plotted as percent change, ±SEM, from D1.

A scatter plot was constructed to show TTE values, by group. The TTE plot includes NTR deaths, which are excluded from all other graphical analyses. When an animal exited the study because of tumor size, the final tumor volume recorded for the animal was included with the data used to calculate the median volume at subsequent time points. The percentage of animals in each group remaining in the study versus time was presented in a Kaplan-Meier survival plot.

Histone Extraction

For isolation of histones, 60-90 mg tumor tissue was homogenized in 1.5 ml nuclear extraction buffer (10 mM Tris-HCl, 10 mM $MgCl_2$, 25 mM KCl, 1% Triton X-100, 8.6% Sucrose, plus a Roche protease inhibitor tablet 1836145) and incubated on ice for 5 minutes. Nuclei were collected by centrifugation at 600 g for 5 minutes at 4° C.

and washed once in PBS. Supernatant was removed and histones extracted for one hour, with vortexing every 15 minutes, with 0.4 N cold sulfuric acid. Extracts were clarified by centrifugation at 10000 g for 10 minutes at 4° C. and transferred to a fresh microcentrifuge tube containing 10× volume of ice cold acetone. Histones were precipitated at −20° C. for 2 hours-overnight, pelleted by centrifugation at 10000 g for 10 minutes and resuspended in water.

ELISA

Histones were extracted from tumor samples as described above. Histones were prepared in equivalent concentrations in coating buffer (PBS+0.05% BSA) yielding 0.5 ng/ul of sample, and 100 ul of sample or standard was added in duplicate to 2 96-well ELISA plates (Thermo Labsystems, Immulon 4HBX #3885). The plates were sealed and incubated overnight at 4° C. The following day, plates were washed 3× with 300 ul/well PBST (PBS+0.05% Tween 20; 10×PBST, KPL #51-14-02) on a Bio Tek plate washer. Plates were blocked with 300 ul/well of diluent (PBS+2% BSA+ 0.05% Tween 20), incubated at RT for 2 hours, and washed 3× with PBST. All antibodies were diluted in diluent. 100 ul/well of anti-H3K27me3 (CST #9733, 50% glycerol stock 1:1,000) or anti-total H3 (Abcam ab1791, 50% glycerol 1:10,000) was added to each plate. Plates were incubated for 90 min at RT and washed 3× with PBST. 100 ul/well of anti-Rb-IgG-HRP (Cell Signaling Technology, 7074) was added 1:2,000 to the H3K27Me3 plate and 1:6,000 to the H3 plate and incubated for 90 min at RT. Plates were washed 4× with PBST. For detection, 100 ul/well of TMB substrate (BioFx Laboratories, #TMBS) was added and plates incubated in the dark at RT for 5 min. Reaction was stopped with 100 ul/well 1N $H_2SO_4$. Absorbance at 450 nm was read on SpectaMax M5 Microplate reader.

Efficacy Study in SUDHL6 Xenograft Model

The efficacy of treatment with Compound 44 and in combination with CHOP on tumor growth inhibition in vivo was determined in the SUDHL6 xenograft model. Comparison of tumor growth and survival rate established that the administration of Compound 44 and CHOP inhibited or delayed tumor growth and increased survival of the tumor-bearing mice. Athymic nude mice were subcutaneously injected with $1 \times 10^7$ SUDHL6 human lymphoma cells. Compound 44 was administered once a day (QD), twice a day (BID), or three times a day (TID) at the indicated concentrations (75 mg/kg, 150 mg/kg, or 225 mg/kg). Mice received CHOP on day 1 and 8. Tumor volume was measured twice a week until the endpoint of 60 days or when tumor volume reached 2000 $mm^3$, whichever occurred first.

The combination therapy of Compound 44 and CHOP showed inhibition of tumor growth over the course of treatment (28 days) in comparison to mice treated with CHOP or Compound 44 alone (FIG. 6A). Significantly, mice receiving combination therapy of Compound 44 and CHOP exhibited a durable regression of tumor size; 7 out of 12 mice demonstrated complete responses on day 60 in the 225 mg/kg BID and CHOP combination group (FIG. 6A). A Kaplan-Meier curve was determined to show the survival of the mice in the study. 57% of mice that received the combination therapy of Compound 44 and CHOP survived 60 days after injection (FIG. 6B). Single agent efficacy with Compound 44 was not observed over the 28 day treatment, however high intra-group variability may have masked the treatment effect of Compound 44 as a single agent.

Efficacy Study in WSU-DLCL2 Xenograft Model

The efficacy of treatment with Compound 44 and in combination with CHOP on tumor growth inhibition in vivo was determined in the WSU-DLCL2 xenograft model. Comparison of tumor growth established that the administration of Compound 44 and CHOP inhibited or delayed tumor growth of the tumor-bearing mice. SCID mice were subcutaneously injected with $1 \times 10^7$ WSU-DLCL2 human lymphoma cells. Compound 44 was administered once a day (QD), twice a day (BID), or three times a day (TID) at the indicated concentrations (150 mg/kg, 225 mg/kg, 300 mg/kg, or 600 mg/kg). Mice received CHOP on day 1 and 22 (CHOP on day 1 and 8 were not tolerated in SCID mice). Tumor volume was measured twice a week until the endpoint of 28 days.

Compound 44 alone and in combination with CHOP therapy resulted in tumor growth inhibition (FIG. 7A). Administration at 150 mg/kg three times a day (TID) and 225 mg/kg twice a day (BID) of Compound 44 as a single agent resulted in significantly smaller tumors by volume when compared to control vehicle treated mice (p<0.05). Moreover, the combination therapy of Compound 44 and CHOP showed statistically significant inhibition of tumor growth in comparison to control vehicle treated mice (p<0.001). Statistical analyses were calculated using Repeated measure ANOVA followed by Dunnett post test. Tumor growth inhibition was also calculated, revealing that treatment of tumors with Compound 44 resulted in greater tumor growth inhibition at all dosages (Table 2). Importantly, the combination treatment of Compound 44 with CHOP resulted in the greatest tumor growth inhibition.

TABLE 2

Tumor Growth Inhibition (TGI) of WSU-DLCL2 xenograft model.

| Group | % TGI from day 1 | % TGI from day 7 |
|---|---|---|
| 150 mg/kg TID | 73 | 86 |
| 225 mg/kg BID | 71 | 80 |
| 300 mg/kg BID | 57 | 67 |
| 600 mg/kg QD | 58 | 70 |
| CHOP combo | 93 | 100 |
| CHOP | 45 | 51 |

To examine the absorption and distribution of the administered agents, pharmacokinetic analysis was performed to determine Compound 44 concentration (ng/mL) in the plasma of tumor-bearing mice (FIG. 7B). Plasma samples were obtained on day 28 at 5 minutes prior to the last dose ("trough") and 3 hours after the last dose ("post"). Plasma samples were analyzed by LC-MS/MS to determine concentration Compound 44 (ng/mL). Compound 44 levels were not significantly different between mice that received 225 mg/kg of Compound 44 twice a day (BID) as a single agent and 225 mg/kg of Compound 44 (BID) with CHOP at the trough timepoint. However, 3 hours post-administration of the last dose, Compound 44 levels were significantly increased in mice that received 225 mg/kg of Compound 44 twice a day (BID) with CHOP compared to single agent Compound 44.

Pharmacokinetic analysis was also performed to determine Compound 44 concentration (ng/g) in tumor tissue harvested from mice on day 28 at 3 hours after the last administration of treatment (FIG. 7C).

Efficacy of target inhibition in vivo was determined by analysis of histone methylation status in tumors after 28 days of treatment. Western Blot analysis (FIG. 8A) demonstrated that methylation of H3K27 was inhibited by Compound 44 at all dosages and dosing schedules in WSU-DLCL2 tumors. Histones were extracted as described above. Protein concentrations for acid extracted histones were determined by BCA assay (Pierce). 400-800ng of each lysate was fractionated on 10-20% Tris-Glycine gel (Biorad), transferred using iBlot (7 minutes on program 3, using Nitrocellulose transfer stacks), and probed with the following antibodies in Odyssey blocking buffer: rabbit anti-H3K27me3 (CST 9733; 1:20000 dilution) and mouse anti-Total H3 (CST 3638; 1:20000 dilution). Following primary Ab incubation, membranes were probed with IRDye 800CW Donkey-anti-mouse IgG (LiCOR #926-32212) and Alexa Fluor 680 goat-anti-rabbit IgG (Invitrogen #A-21076) secondary Ab and imaged using the LiCOR Odyssey system. Signal from total histone H3 protein was used as control.

Analysis of histone methylation in WSU-DLCL2 tumors by ELISA confirmed that methylation of histones was inhibited by Compound 44 at all dosages and dosing schedules (FIG. 8B). Tumors from mice that received vehicle or CHOP did not exhibit any inhibition of methylation at H3K27. Histones were extracted from tumors after 28 days of treatment and analyzed by ELISA as described above.

Efficacy Study in SUDHL10 Xenograft Model

The efficacy of treatment with Compound 44 and in combination with COP (Cyclosphosphamide, Oncovin [vincristine], and Prednisone) on tumor growth inhibition in vivo was determined in the SUDHL10 xenograft model. Comparison of tumor growth established that the administration of Compound 44 and COP inhibited or delayed tumor growth of the tumor-bearing mice. SCID mice were subcutaneously injected with 1×10⁷ SUDHL10 human lymphoma cells. Compound 44 was administered twice a day (BID), or three times a day (TID) at the indicated concentrations (125 mg/kg, 250 mg/kg, or 500 mg/kg). Mice received COP on day 1 and 22 (CHOP on day 1 and 8 were not tolerated in SCID mice). Tumor volume was measured twice a week until the endpoint of 28 days. Half the cohort were euthanized after 28 days of treatment, while the other half were analyzed until a 60 day endpoint for analysis of tumor growth delay.

FIG. 9A shows that administration of Compound 44 alone showed statistically significant tumor growth inhibition as a single agent at 250 mg/kg and 500 mg/kg when delivered twice a day (BID), when compared to control vehicle treated mice (p<0.001). Moreover, the combination therapy of Compound 44 at 250 mg/kg twice a day (BID) and COP showed statistically significant inhibition of tumor growth in comparison to control vehicle treated mice (p<0.001). Statistical analyses were calculated using Repeated measure ANOVA followed by Dunnett post test. One mouse in the 500 mg/kg BID group was euthanized on day 15 due to poor body condition. Mice receiving Compound 44 and COP combination therapy exhibited 8% body weight loss on day 25, in which dosing was stopped but resumed at day 27. On day 29, 1/16 mice and 2/15 mice were without tumor in 250 mg/kg and 500 mg/kg group. Strikingly, 10/14 mice receiving Compound 44 and COP combination therapy were without tumor on day 29.

Tumor growth inhibition was also calculated, revealing that treatment of SUDHL10 xenograft tumors with Compound 44, with or without COP resulted in effective tumor growth inhibition at all dosages (Table 3).

TABLE 3

Tumor Growth Inhibition (TGI) in SUDHL10 xenograft model.

| Group | % TGI from day 1 | % TGI from day 7 |
|---|---|---|
| 125 mg/kg BID | 54 | 57 |
| 250 mg/kg BID | 101 | 113 |

TABLE 3-continued

Tumor Growth Inhibition (TGI) in SUDHL10 xenograft model.

| Group | % TGI from day 1 | % TGI from day 7 |
|---|---|---|
| 500 mg/kg BID | 104 | 115 |
| COP | 42 | 43 |
| COP combo | 107 | 108 |

Tumors were weighed after mice were euthanized on day 28 (FIG. 9B). Tumors from mice receiving single agent administration of Compound 44 at 125 mg/kg or COP were significantly smaller compared to control mice (vehicle). Tumors from mice receiving combination therapy of Compound 44 and COP were significantly smaller than tumors from mice receiving Compound 44 as a single agent at both 250 mg/kg and 500 mg/kg dosages.

Half the cohort was maintained to day 60, to determine efficacy treatment by determining tumor growth delay (FIG. 9C). Tumor growth in mice treated with 250 mg/kg and 500 mg/kg doses of Compound 44 as a single agent exhibited small tumors at day 28, while control and COP treated mice exhibited large tumors where the tumors continued to grow after day 28. Strikingly, mice receiving the combination therapy not only had smaller tumors than all other treatment groups, but also displayed significant and durable tumor growth delay.

FIG. 9D shows a Kaplan-Meier curve depicting the survival rate of mice treated with Compound 44 alone or in combination in COP. Administration of Compound 44 as a single agent at 125 mg/kg, 250 mg/kg, and 500 mg/kg increased the survival of mice compared to control mice or mice treated with COP only. Significantly, combined administration of Compound 44 with COP improved the survival rate of mice compared to single agent administration.

Pharmacokinetic and pharmacodynamic studies were performed on the SUDHL10 xenograft model. FIG. 10A shows pharmacokinetic analysis of Compound 44 concentrations in plasma levels (ng/mL). Plasma samples were obtained from tumor-bearing mice on day 28 at either 5 minutes prior to the last dose ("trough") or 3 hours after the last dose ("post"). Levels of Compound 44 was determined by LC-MS. Pharmacodynamic analysis was performed by ELISA and determining the ratio of tri-methylated H3K27 in tumor samples. Pharmacodynamic analysis was also performed in other tissues, specifically the spleen and bone marrow, of the tumor-bearing mice to show the efficacy of inhibition of histone methylation by Compound 44 in normal tissues of the surrogate mouse (FIGS. 10B and 10C).

Example 7: Synergistic Effects of Compound 44 and Anti-Cancer Agents Combination Therapy Methods The human lymphoma cell lines WSU-DLCL2 (DSMZ; ACC 575), SU-DHL-10 (DSMZ; ACC 576), and Toledo (ATCC; CRL-2631) were obtained from the indicated sources and maintained in RPMI-1640 media supplemented with 10%-20% heat inactivated fetal bovine serum and 2 mM glutamine. The cells were cultured in tissue culture flasks in a humidified incubator at 37° C., in an atmosphere of 5% CO2 and 95% air. The WSU-DLCL2 and SU-DHL-10 contain the Y641 EZH2 mutation, and the Toledo cell line contains WT EZH2.

The in vitro anti-proliferative effects of the combination of Compound 44 with the following drugs: AraC, Cisplatin, Decitabine, Dexamethasone, Everolimus, Prednisolone, and Doxorubicin were investigated. WSU-DLCL2, SU-DHL-10, or Toledo human lymphoma cells were treated with increasing concentrations of Compound 44 in flasks. After 4 days of treatment, the WSU-DLCL2 or SU-DHL-10 cells were split to initial seeding density and plated into a 96-well tissue culture plate with each concentration of Compound 44 in one row of the plate. After 6 days the Toledo cells were split to initial seeding density and plated into a 96-well tissue culture plate with each concentration of Compound 44 in one row of the plate. Increasing doses of drugs were then added to the plates. One dose per column forming a matrix of Compound 44 and drug doses. After incubation for an additional 3 days cell viability of WSU-DLCL2 or SU-DHL-10 was measured using Promega Cell Titer-Glo reagent followed by luminescence detection. After 5 days viability of Toledo cells was measured using Promega Cell Titer-Glo reagent followed by luminescence detection.

Data Analysis

Synergy was determined using the software package Calcusyn by Biosoft based on the Chou-Talalay method for drug combination which uses the median-effect equation (Chou 2006). First, raw luminescence values were converted to percent inhibition or fraction affected (Fa) calculated using controls for maximum inhibition and DMSO treated cells for minimum inhibition control located on each plate. Percent inhibition values for each constant ratio of compound combinations were entered into Calcusyn to determine the combination index values. Combination index values less than 1 indicated synergy.

For test compounds that did not inhibit cells viability by 50%, synergy cannot be determined using Calcusyn. Instead, the data was reported as fold IC50 shift of the IC50 for Compound 44. Alternatively, if Compound 44 did not have an effect, as with the Toledo cells, the fold IC50 shift was reported for the drug instead of Compound 44.

Results

Treatment of WSU-DLCL2 and SU-DHL-10 cells with Compound 44 and either AraC, Cisplatin, Doxorubicin, Decitabine, or Everolimus demonstrated synergistic reduction in cell viability. Combination index values for combinations with Compound 44 and Decitabine in WSU-DLCL2 and SU-DHL-10 cells were below 0.1 which is denoted by very strong synergism according to the Chou-Talalay characterization (Chou 2006). Combination index values for combinations with Compound 44 and Everolimus in WSU-DLCL2 cells were below 0.1 and SU-DHL-10 cells between 0.1-0.3 which is denoted by very strong synergism and strong synergism respectively. Combinations with Compound 44 and either AraC, Cisplatin, or Doxorubicin in WSU-DLCL2 and SU-DHL-10 cells had combination index values between 0.3-0.7 which denotes synergism (Chou 2006). Combination of Compound 44 with Prednisolone enhanced the Compound 44 potency by 7-fold for WSU-DLCL2 and 3-fold for SU-DHL-10 cells at the top dose of Prednisolone. Additionally, combination with Compound 44 and Dexamethasone enhanced the Compound 44 potency by 17-fold for WSU-DLCL2 cells and 3-fold for SU-DHL-10 cells at the top does of Dexamethasone.

The Toledo cell line showed no sensitivity to Compound 44 and no combination benefit was seen when Compound 44 was combined with either AraC, Cisplatin, Doxorubicin, Decitabine, Everolimus, Prednisolone, or Dexamethasone. Thus the combination benefit seen in these experiments appears to be dependent on EZH2 mutation.

TABLE 4

List of compounds and cell lines

| | WSU | SUDHL10 | Toledo |
|---|---|---|---|
| Prednisolone | 7-fold enhancement | 3-fold enhancement | No enhancement |
| Doxorubicin | Synergism CI 0.3-0.7 | Synergism CI 0.3-0.7 | No enhancement |
| Cisplatin | Synergism CI 0.3-0.7 | n/a | No enhancement |
| AraC | Synergism CI 0.3-0.7 | Synergism CI 0.3-0.7 | No enhancement |
| Everolimus | Very strong synergism CI < 0.1 | Strong synergism CI 0.1-0.3 | No enhancement |
| Decitabine | Very strong synergism CI < 0.1 | Very strong synergism CI < 0.1 | No enhancement |
| Dexamethasone | 17-fold enhancement | 3-fold enhancement | No enhancement |

INCORPORATION BY REFERENCE

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating cancer comprising administering to a subject in need thereof a therapeutically effective dose of a compound of Formula (IIa):

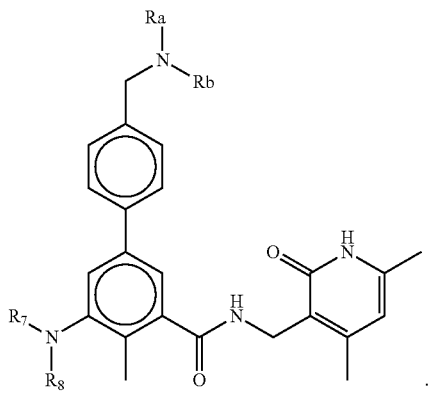

or a pharmaceutically acceptable salt thereof, and dexamethasone, wherein
each of $R_a$ and $R_b$, independently, is H or $C_1$-$C_6$ alkyl; or $R_a$ and $R_b$, together with the N atom to which they are attached, form a 4 to 7-membered heterocycloalkyl ring having 0 or 1 additional heteroatoms; wherein the $C_1$-$C_6$ alkyl or the 4 to 7-membered heterocycloalkyl ring are optionally substituted with one or more -$Q_3$-$T_3$, in which $Q_3$ is a bond or unsubstituted or substituted $C_1$-$C_3$ alkyl linker, and $T_3$ is H, halo, 4 to 7-membered heterocycloalkyl, $C_1$-$C_3$ alkyl, $OR_d$, $COOR_d$, —$S(O)_2R_d$, or —$NR_dR_e$, in which each of $R_d$ and $R_e$ is independently H or $C_1$-$C_6$ alkyl, or -$Q_3T_3$ is oxo;
$R_7$ is isopropyl or $C_1$-$C_6$ alkyl, $C_3$-$C_8$ cycloalkyl, piperidinyl, tetrahydropyran, tetrahydro-2H-thiopyranyl, cyclopentyl, or cyclohexyl, or 4 to 12-membered heterocycloalkyl, each optionally substituted with one or more -$Q_5$-$T_5$, in which $Q_5$ is a bond, C(O), $C(O)NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; and
$R_8$ is H, methyl, or ethyl; and
wherein the compound of Formula (IIa) and said dexamethasone are administered simultaneously or sequentially.

2. The method claim 1, wherein the compound of Formula (IIa) or a pharmaceutically acceptable salt thereof is administered prior to administration of said dexamethasone.

3. The method of claim 1, wherein the compound of Formula (IIa) is administered at a dosage of from about 0.01 mg/kg per day to about 1000 mg/kg per day.

4. The method of claim 1, wherein the dexamethasone is administered at a dosage of from about 0.01 mg/kg per day to about 1000 mg/kg per day.

5. The method of claim 1, wherein said subject expresses mutant EZH2.

6. The method of claim 5, wherein the mutant EZH2 has a mutation at amino acid position 677, 687, 674, 685, or 641 of SEQ ID NO: 1.

7. The method of claim 5, wherein said mutant EZH2 has one or more mutations selected from the group consisting of a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V);

a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of serine (S) for the wild type residue asparagine (N) at amino acid position 322 of SEQ ID NO: 3 (N322S), a substitution of glutamine (Q) for the wild type residue arginine (R) at amino acid position 288 of SEQ ID NO: 3 (R288Q), a substitution of isoleucine (I) for the wild type residue threonine (T) at amino acid position 573 of SEQ ID NO: 3 (T573I), a substitution of glutamic acid (E) for the wild type residue aspartic acid (D) at amino acid position 664 of SEQ ID NO: 3 (D664E), a substitution of glutamine (Q) for the wild type residue arginine (R) at amino acid position 458 of SEQ ID NO: 5 (R458Q), a substitution of lysine (K) for the wild type residue glutamic acid (E) at amino acid position 249 of SEQ ID NO: 3 (E249K), a substitution of cysteine (C) for the wild type residue arginine (R) at amino acid position 684 of SEQ ID NO: 3 (R684C), a substitution of histidine (H) for the wild type residue arginine (R) at amino acid position 628 of SEQ ID NO: 11 (R628H), a substitution of histidine (H) for the wild type residue glutamine (Q) at amino acid position 501 of SEQ ID NO: 5 (Q501H), a substitution of asparagine (N) for the wild type residue aspartic acid (D) at amino acid position 192 of SEQ ID NO: 3 (D192N), a substitution of valine (V) for the wild type residue aspartic acid (D) at amino acid position 664 of SEQ ID NO: 3 (D664V), a substitution of leucine (L) for the wild type residue valine (V) at amino acid position 704 of SEQ ID NO: 3 (V704L), a substitution of serine (S) for the wild type residue proline (P) at amino acid position 132 of SEQ ID NO: 3 (P132S), a substitution of lysine (K) for the wild type residue glutamic acid (E) at amino acid position 669 of SEQ ID NO: 11 (E669K), a substitution of threonine (T) for the wild type residue alanine (A) at amino acid position 255 of SEQ ID NO: 3 (A255T), a substitution of valine (V) for the wild type residue glutamic acid (E) at amino acid position 726 of SEQ ID NO: 3 (E726V), a substitution of tyrosine (Y) for the wild type residue cysteine (C) at amino acid position 571 of SEQ ID NO: 3 (C571Y), a substitution of cysteine (C) for the wild type residue phenylalanine (F) at amino acid position 145 of SEQ ID NO: 3 (F145C), a substitution of threonine (T) for the wild type residue asparagine (N) at amino acid position 693 of SEQ ID NO: 3 (N693T), a substitution of serine (S) for the wild type residue phenylalanine (F) at amino acid position 145 of SEQ ID NO: 3 (F145S), a substitution of histidine (H) for the wild type residue glutamine (Q) at amino acid position 109 of SEQ ID NO: 11 (Q109H), a substitution of cysteine (C) for the wild type residue phenylalanine (F) at amino acid position 622 of SEQ ID NO: 11 (F622C), a substitution of arginine (R) for the wild type residue glycine (G) at amino acid position 135 of SEQ ID NO: 3 (G135R), a substitution of glutamine (Q) for the wild type residue arginine (R) at amino acid position 168 of SEQ ID NO: 5 (R168Q), a substitution of arginine (R) for the wild type residue glycine (G) at amino acid position 159 of SEQ ID NO: 3 (G159R), a substitution of cysteine (C) for the wild type residue arginine (R) at amino acid position 310 of SEQ ID NO: 5 (R310C), a substitution of histidine (H) for the wild type residue arginine (R) at amino acid position 561 of SEQ ID NO: 3 (R561H), a substitution of histidine (H) for the wild type residue arginine (R) at amino acid position 634 of SEQ ID NO: 11 (R634H), a substitution of arginine (R) for the wild type residue glycine (G) at amino acid position 660 of SEQ ID NO: 3 (G660R), a substitution of cysteine (C) for the wild type residue tyrosine (Y) at amino acid position 181 of SEQ ID NO: 3 (Y181C), a substitution of arginine (R) for the wild type residue histidine (H) at amino acid position 297 of SEQ ID NO: 3 (H297R), a substitution of serine (S) for the wild type residue cysteine (C) at amino acid position 612 of SEQ ID NO: 11 (C612S), a substitution of tyrosine (Y) for the wild type residue histidine (H) at amino acid position 694 of SEQ ID NO: 3 (H694Y), a substitution of alanine (A) for the wild type residue aspartic acid (D) at amino acid position 664 of SEQ ID NO: 3 (D664A), a substitution of threonine (T) for the wild type residue isoleucine (I) at amino acid position 150 of SEQ ID NO: 3 (I150T), a substitution of arginine (R) for the wild type residue isoleucine (I) at amino acid position 264 of SEQ ID NO: 3 (I264R), a substitution of leucine (L) for the wild type residue proline (P) at amino acid position 636 of SEQ ID NO: 3 (P636L), a substitution of threonine (T) for the wild type residue isoleucine (I) at amino acid position 713 of SEQ ID NO: 3 (I713T), a substitution of proline (P) for the wild type residue glutamine (Q) at amino acid position 501 of SEQ ID NO: 5 (Q501P), a substitution of glutamine (Q) for the wild type residue lysine (K) at amino acid position 243 of SEQ ID NO: 3 (K243Q), a substitution of aspartic acid (D) for the wild type residue glutamic acid (E) at amino acid position 130 of SEQ ID NO: 5 (E130D), a substitution of glycine (G) for the wild type residue arginine (R) at amino acid position 509 of SEQ ID NO: 3 (R509G), a substitution of histidine (H) for the wild type residue arginine (R) at amino acid position 566 of SEQ ID NO: 3 (R566H), a substitution of histidine (H) for the wild type residue aspartic acid (D) at amino acid position 677 of SEQ ID NO: 3 (D677H), a substitution of asparagine (N) for the wild type residue lysine (K) at amino acid position 466 of SEQ ID NO: 5 (K466N), a substitution of histidine (H) for the wild type residue arginine (R) at amino acid position 78 of SEQ ID NO: 3 (R78H), a substitution of methionine (M) for the wild type residue lysine (K) at amino acid position 1 of SEQ ID NO: 6 (K6M), a substitution of leucine (L) for the wild type residue serine (S) at amino acid position 538 of SEQ ID NO: 3 (S538L), a substitution of glutamine (Q) for the wild type residue leucine (L) at amino acid position 149 of SEQ ID NO: 3 (L149Q), a substitution of valine (V) for the wild type residue leucine (L) at amino acid position 252 of SEQ ID NO: 3 (L252V), a substitution of valine (V) for the wild type residue leucine (L) at amino acid position 674 of SEQ ID NO: 3 (L674V), a substitution of valine (V) for the wild type residue alanine (A) at amino acid position 656 of SEQ ID NO: 3 (A656V), a substitution of aspartic acid (D) for the wild type residue alanine (A) at amino acid position 731 of SEQ ID NO: 3 (Y731D), a substitution of threonine (T) for the wild type residue alanine (A) at amino acid position 345 of SEQ ID NO: 3 (A345T), a substitution of aspartic acid (D) for the wild type residue alanine (A) at amino acid position 244 of SEQ ID NO: 3 (Y244D), a substitution of tryptophan (W) for the wild type residue cysteine (C) at amino acid position 576 of SEQ ID NO: 3 (C576W), a substitution of lysine (K) for the wild type residue asparagine (N) at amino acid position 640 of SEQ ID NO: 3 (N640K), a substitution of lysine (K) for the wild type residue asparagine (N) at amino acid position 675 of SEQ ID NO: 3 (N675K), a substitution of tyrosine (Y) for the wild type residue aspartic acid (D) at amino acid position 579 of SEQ ID NO: 11 (D579Y), a substitution of isoleucine (I) for the wild type residue asparagine (N) at amino acid position 693 of SEQ ID NO: 3 (N693I), and a substitution of lysine (K) for the wild type residue asparagine (N) at amino acid position 693 of SEQ ID DO: 3 (N693K).

8. The method of claim 1, wherein said subject has demonstrated resistance to a compound of Formula (IIa) or to dexamethasone when administered as a single agent.

9. The method of claim 1, wherein the cancer is lymphoma, leukemia, or melanoma.

* * * * *

SEQUENCE LISTING

<160> NUMBER OF SEQ ID NOS: 12

<210> SEQ ID NO 1
<211> LENGTH: 746
<212> TYPE: PRT
<213> ORGANISM: Homo sapiens

<400> SEQUENCE: 1

-continued

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
            35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65              70                  75                  80

Arg Glu Cys Ser Val Thr Ser Asp Leu Asp Phe Pro Thr Gln Val Ile
            85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
            115                 120                 125

His Asn Ile Pro Tyr Met Gly Asp Glu Val Leu Asp Gln Asp Gly Thr
        130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
                180                 185                 190

Pro Glu Glu Arg Glu Glu Lys Gln Lys Asp Leu Glu Asp His Arg Asp
                195                 200                 205

Asp Lys Glu Ser Arg Pro Pro Arg Lys Phe Pro Ser Asp Lys Ile Phe
        210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
            275                 280                 285

Cys Phe Lys Tyr Asp Cys Phe Leu His Pro Phe His Ala Thr Pro Asn
        290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
            325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
        370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Ser Glu Ala Asn Ser Arg Cys Gln Thr
                405                 410                 415
```

```
Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
    450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
            530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
            595                 600                 605

Gly Ser Lys Lys His Leu Leu Leu Ala Pro Ser Asp Val Ala Gly Trp
            610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
            675                 680                 685

His Ser Val Asn Pro Asn Cys Tyr Ala Lys Val Met Met Val Asn Gly
            690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 2
<211> LENGTH: 2723
<212> TYPE: DNA
<213> ORGANISM: Homo sapiens

<400> SEQUENCE: 2
ggcggcgctt gattgggctg gggggggccaa ataaaagcga tggcgattgg gctgccgcgt      60
ttggcgctcg gtccggtcgc gtccgacacc cggtgggact cagaaggcag tggagccccg     120
gcggcggcgg cggcggcgcg cggggcgac gcgcggaac aacgcgagtc ggcgcgcggg     180
acgaagaata atcatgggcc agactgggaa gaaatctgag aagggaccag tttgttggcg     240
```

-continued

```
gaagcgtgta aaatcagagt acatgcgact gagacagctc aagaggttca gacgagctga    300
tgaagtaaag agtatgttta gttccaatcg tcagaaaatt ttggaaagaa cggaaatctt    360
aaaccaagaa tggaaacagc gaaggataca gcctgtgcac atcctgactt ctgtgagctc    420
attgcgcggg actagggagt gttcggtgac cagtgacttg gattttccaa cacaagtcat    480
cccattaaag actctgaatg cagttgcttc agtacccata atgtattctt ggtctcccct    540
acagcagaat tttatggtgg aagatgaaac tgttttacat aacattcctt atatgggaga    600
tgaagtttta gatcaggatg gtactttcat tgaagaacta ataaaaaatt atgatgggaa    660
agtacacggg gatagagaat gtgggtttat aaatgatgaa attttgtgg agttggtgaa     720 tgcccttggt caatataatg atgatgacga tgatgatgat ggagacgatc ctgaagaaag    780
agaagaaaag cagaaagatc tggaggatca ccgagatgat aaagaaagcc gcccacctcg    840
gaaatttcct tctgataaaa ttttttgaagc catttcctca atgtttccag ataagggcac    900
agcagaagaa ctaaaggaaa aatataaaga actcaccgaa cagcagctcc caggcgcact    960
tcctcctgaa tgtaccccca acatagatgg accaaatgct aaatctgttc agagagagca   1020
aagcttacac tccttttcata cgcttttctg taggcgatgt tttaaatatg actgcttcct   1080
acatcgtaag tgcaattatt cttttcatgc aacacccaac acttataagc ggaagaacac   1140
agaaacagct ctagacaaca aaccttgtgg accacagtgt taccagcatt tggagggagc   1200
aaaggagttt gctgctgctc tcaccgctga gcggataaag accccaccaa aacgtccagg   1260
aggccgcaga agaggacggc ttcccaataa cagtagcagg cccagcaccc ccaccattaa   1320
tgtgctggaa tcaaaggata cagacagtga tagggaagca gggactgaaa cggggggaga   1380
gaacaatgat aaagaagaag aagagaagaa agatgaaact tcgagctcct ctgaagcaaa   1440
ttctcggtgt caaacaccaa taagatgaa gccaaatatt gaacctcctg agaatgtgga    1500
gtggagtggt gctgaagcct caatgtttag agtcctcatt ggcacttact atgacaattt   1560
ctgtgccatt gctaggttaa ttgggaccaa aacatgtaga caggtgtatg agtttagagt   1620
caaagaatct agcatcatag ctccagctcc cgctgaggat gtggatactc ctccaaggaa   1680
aaagaagagg aaaacaccggt tgtgggctgc acactgcaga aagatacagc tgaaaaagga   1740
cggctcctct aaccatgttt acaactatca accctgtgat catccacggc agccttgtga   1800
cagttcgtgc ccttgtgtga tagcacaaaa ttttttgtgaa aagttttgtc aatgtagttc   1860
agagtgtcaa aaccgctttc cgggatgccg ctgcaaagca cagtgcaaca ccaagcagtg   1920
cccgtgctac ctggctgtcc gagagtgtga ccctgacctc tgtcttactt gtggagccgc   1980
tgaccattgg gacagtaaaa atgtgtcctg caagaactgc agtattcagc ggggctccaa   2040
aaagcatcta ttgctggcac catctgacgt ggcaggctgg gggattttta tcaaagatcc   2100
tgtgcagaaa aatgaattca tctcagaata ctgtggagag attatttctc aagatgaagc   2160
tgacagaaga gggaaagtgt atgataaata catgtgcagc tttctgttca acttgaacaa   2220
tgattttgtg gtggatgcaa cccgcaaggg taacaaaatt cgttttgcaa atcattcggt   2280
aaatccaaac tgctatgcaa aagttatgat ggttaacggt gatcacagga taggtatttt   2340
tgccaagaga gccatccaga ctggcgaaga gctgttttttt gattacagat acagccaggc   2400
tgatgccctg aagtatgtcg gcatcgaaag agaaatggaa atcccttgac atctgctacc   2460
tcctcccccc tcctctgaaa cagctgcctt agcttcagga acctcgagta ctgtgggcaa   2520
tttagaaaaa gaacatgcag tttgaaattc tgaatttgca aagtactgta agaataattt   2580
atagtaatga gtttaaaaat caacttttta ttgccttctc accagctgca aagtgttttg   2640
```

```
taccagtgaa ttttgcaat aatgcagtat ggtacatttt tcaactttga ataaagaata    2700
cttgaacttg tccttgttga atc                                           2723
```

<210> SEQ ID NO 3
<211> LENGTH: 751
<212> TYPE: PRT
<213> ORGANISM: Homo sapiens

<400> SEQUENCE: 3

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Arg Lys Cys Asn Tyr Ser Phe
    290                 295                 300

His Ala Thr Pro Asn Thr Tyr Lys Arg Lys Asn Thr Glu Thr Ala Leu
305                 310                 315                 320

Asp Asn Lys Pro Cys Gly Pro Gln Cys Tyr Gln His Leu Glu Gly Ala
                325                 330                 335

Lys Glu Phe Ala Ala Ala Leu Thr Ala Glu Arg Ile Lys Thr Pro Pro
            340                 345                 350
```

-continued

| | | | | | | | | | | | |
|---|---|---|---|---|---|---|---|---|---|---|---|
|Lys|Arg|Pro|Gly|Gly|Arg|Arg|Gly|Arg|Leu|Pro|Asn Asn Ser Ser|
| |  |  | 355|  |  |  | 360|  |  | 365|  |

Lys Arg Pro Gly Gly Arg Arg Gly Arg Leu Pro Asn Asn Ser Ser
       355                 360             365

Arg Pro Ser Thr Pro Thr Ile Asn Val Leu Glu Ser Lys Asp Thr Asp
370             375                 380

Ser Asp Arg Glu Ala Gly Thr Glu Thr Gly Gly Glu Asn Asn Asp Lys
385                 390             395                 400

Glu Glu Glu Glu Lys Lys Asp Glu Thr Ser Ser Ser Glu Ala Asn
            405                 410             415

Ser Arg Cys Gln Thr Pro Ile Lys Met Lys Pro Asn Ile Glu Pro Pro
            420             425             430

Glu Asn Val Glu Trp Ser Gly Ala Glu Ala Ser Met Phe Arg Val Leu
            435             440             445

Ile Gly Thr Tyr Tyr Asp Asn Phe Cys Ala Ile Ala Arg Leu Ile Gly
        450             455             460

Thr Lys Thr Cys Arg Gln Val Tyr Glu Phe Arg Val Lys Glu Ser Ser
465             470             475             480

Ile Ile Ala Pro Ala Pro Ala Glu Asp Val Asp Thr Pro Pro Arg Lys
                485             490             495

Lys Lys Arg Lys His Arg Leu Trp Ala Ala His Cys Arg Lys Ile Gln
            500             505             510

Leu Lys Lys Asp Gly Ser Ser Asn His Val Tyr Asn Tyr Gln Pro Cys
        515             520             525

Asp His Pro Arg Gln Pro Cys Asp Ser Ser Cys Pro Cys Val Ile Ala
    530             535             540

Gln Asn Phe Cys Glu Lys Phe Cys Gln Cys Ser Ser Glu Cys Gln Asn
545             550             555             560

Arg Phe Pro Gly Cys Arg Cys Lys Ala Gln Cys Asn Thr Lys Gln Cys
                565             570             575

Pro Cys Tyr Leu Ala Val Arg Glu Cys Asp Pro Asp Leu Cys Leu Thr
            580             585             590

Cys Gly Ala Ala Asp His Trp Asp Ser Lys Asn Val Ser Cys Lys Asn
        595             600             605

Cys Ser Ile Gln Arg Gly Ser Lys Lys His Leu Leu Leu Ala Pro Ser
610             615             620

Asp Val Ala Gly Trp Gly Ile Phe Ile Lys Asp Pro Val Gln Lys Asn
625             630             635             640

Glu Phe Ile Ser Glu Tyr Cys Gly Glu Ile Ile Ser Gln Asp Glu Ala
            645             650             655

Asp Arg Arg Gly Lys Val Tyr Asp Lys Tyr Met Cys Ser Phe Leu Phe
            660             665             670

Asn Leu Asn Asn Asp Phe Val Val Asp Ala Thr Arg Lys Gly Asn Lys
            675             680             685

Ile Arg Phe Ala Asn His Ser Val Asn Pro Asn Cys Tyr Ala Lys Val
        690             695             700

Met Met Val Asn Gly Asp His Arg Ile Gly Ile Phe Ala Lys Arg Ala
705             710             715             720

Ile Gln Thr Gly Glu Glu Leu Phe Phe Asp Tyr Arg Tyr Ser Gln Ala
            725             730             735

Asp Ala Leu Lys Tyr Val Gly Ile Glu Arg Glu Met Glu Ile Pro
            740             745             750

<210> SEQ ID NO 4
<211> LENGTH: 2591
<212> TYPE: DNA

<213> ORGANISM: Homo sapiens

<400> SEQUENCE: 4

```
ggcggcgctt gattgggctg gggggggccaa ataaaagcga tggcgattgg gctgccgcgt      60
ttggcgctcg gtccggtcgc gtccgacacc cggtgggact cagaaggcag tggagcccg      120
gcggcggcgg cggcggcgcg cggggggcgac gcgcgggaac aacgcgagtc ggcgcgcggg     180
acgaagaata atcatgggcc agactgggaa gaaatctgag aagggaccag tttgttggcg     240
gaagcgtgta aaatcagagt acatgcgact gagacagctc aagaggttca gacgagctga     300
tgaagtaaag agtatgttta gttccaatcg tcagaaaatt ttggaaagaa cggaaatctt     360
aaaccaagaa tggaaacagc gaaggataca gcctgtgcac atcctgactt ctgtgagctc     420
attgcgcggg actagggagg tggaagatga aactgtttta cataacattc cttatatggg     480
agatgaagtt ttagatcagg atggtacttt cattgaagaa ctaataaaaa attatgatgg     540
gaaagtacac ggggatagag aatgtgggtt tataaatgat gaaattttg tggagttggt      600
gaatgcccctt ggtcaatata atgatgatga cgatgatgat gatggagacg atcctgaaga    660
aagagaagaa aagcagaaag atctggagga tcaccgagat gataaagaaa gccgcccacc     720
tcggaaattt ccttctgata aaattttga agccatttcc tcaatgtttc cagataaggg     780
cacagcagaa gaactaaagg aaaaatataa agaactcacc gaacagcagc tcccaggcgc    840
acttcctcct gaatgtaccc ccaacataga tggaccaaat gctaaatctg ttcagagaga    900
gcaaagctta cactccttc atacgctttt ctgtaggcga tgttttaaat atgactgctt      960
cctacatcct tttcatgcaa cacccaacac ttataagcgg aagaacacag aaacagctct    1020
agacaacaaa ccttgtggac cacagtgtta ccagcatttg gagggagcaa aggagtttgc   1080
tgctgctctc accgctgagc ggataaagac cccaccaaaa cgtccaggag ccgcagaag    1140
aggacggctt cccaataaca gtagcaggcc cagcaccccc accattaatg tgctggaatc    1200
aaaggataca gacagtgata gggaagcagg gactgaaacg gggggagaga acaatgataa    1260
agaagaagaa gagaagaaag atgaaacttc gagctcctct gaagcaaatt ctcggtgtca    1320
aacaccaata aagatgaagc caaatattga acctcctgag aatgtggagt ggagtggtgc    1380
tgaagcctca atgtttagag tcctcattgg cacttactat gacaatttct gtgccattgc    1440
taggttaatt gggaccaaaa catgtagaca ggtgtatgag tttagagtca aagaatctag    1500
catcatagct ccagctcccg ctgaggatgt ggatactcct ccaaggaaaa agaagaggaa    1560
acaccggttg tgggctgcac actgcagaaa gatacagctg aaaaaggacg gctcctctaa    1620
ccatgtttac aactatcaac cctgtgatca tccacggcag ccttgtgaca gttcgtgccc    1680
ttgtgtgata gcacaaaatt tttgtgaaaa gttttgtcaa tgtagttcag agtgtcaaaa    1740
ccgctttccg ggatgccgct gcaaagcaca gtgcaacacc aagcagtgcc cgtgctacct    1800
ggctgtccga gagtgtgacc ctgacctctg tcttacttgt ggagccgctg accattggga    1860
cagtaaaaat gtgtcctgca agaactgcag tattcagcgg ggctccaaaa agcatctatt    1920
gctggcacca tctgacgtgg caggctgggg gattttatc aaagatcctg tgcagaaaaa     1980
tgaattcatc tcagaatact gtggagagat tatttctcaa gatgaagctg acagaagagg    2040
gaaagtgtat gataaataca tgtgcagctt tctgttcaac ttgaacaatg attttgtggt    2100
ggatgcaacc cgcaagggta acaaattcg ttttgcaaat cattcggtaa atccaaactg     2160
ctatgcaaaa gttatgatgg ttaacggtga tcacaggata ggtattttg ccaagagagc     2220
catccagact ggcgaagagc tgttttttga ttacagatac agccaggctg atgccctgaa    2280
```

```
gtatgtcggc atcgaaagag aaatggaaat cccttgacat ctgctacctc ctcccccctc    2340
ctctgaaaca gctgccttag cttcaggaac ctcgagtact gtgggcaatt tagaaaaaga    2400
acatgcagtt tgaaattctg aatttgcaaa gtactgtaag aataatttat agtaatgagt    2460
ttaaaaatca acttttattt gccttctcac cagctgcaaa gtgttttgta ccagtgaatt    2520
tttgcaataa tgcagtatgg tacattttc aactttgaat aaagaatact tgaacttgtc     2580
cttgttgaat c                                                         2591

<210> SEQ ID NO 5
<211> LENGTH: 707
<212> TYPE: PRT
<213> ORGANISM: Homo sapiens

<400> SEQUENCE: 5

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Val Glu Asp Glu Thr Val Leu His Asn Ile Pro Tyr Met Gly
                85                  90                  95

Asp Glu Val Leu Asp Gln Asp Gly Thr Phe Ile Glu Glu Leu Ile Lys
            100                 105                 110

Asn Tyr Asp Gly Lys Val His Gly Asp Arg Glu Cys Gly Phe Ile Asn
        115                 120                 125

Asp Glu Ile Phe Val Glu Leu Val Asn Ala Leu Gly Gln Tyr Asn Asp
    130                 135                 140

Asp Asp Asp Asp Asp Gly Asp Asp Pro Glu Glu Arg Glu Glu Lys
145                 150                 155                 160

Gln Lys Asp Leu Glu Asp His Arg Asp Asp Lys Glu Ser Arg Pro Pro
                165                 170                 175

Arg Lys Phe Pro Ser Asp Lys Ile Phe Glu Ala Ile Ser Ser Met Phe
            180                 185                 190

Pro Asp Lys Gly Thr Ala Glu Glu Leu Lys Glu Lys Tyr Lys Glu Leu
        195                 200                 205

Thr Glu Gln Gln Leu Pro Gly Ala Leu Pro Pro Glu Cys Thr Pro Asn
    210                 215                 220

Ile Asp Gly Pro Asn Ala Lys Ser Val Gln Arg Glu Gln Ser Leu His
225                 230                 235                 240

Ser Phe His Thr Leu Phe Cys Arg Arg Cys Phe Lys Tyr Asp Cys Phe
                245                 250                 255

Leu His Pro Phe His Ala Thr Pro Asn Thr Tyr Lys Arg Lys Asn Thr
            260                 265                 270

Glu Thr Ala Leu Asp Asn Lys Pro Cys Gly Pro Gln Cys Tyr Gln His
        275                 280                 285

Leu Glu Gly Ala Lys Glu Phe Ala Ala Ala Leu Thr Ala Glu Arg Ile
    290                 295                 300

Lys Thr Pro Pro Lys Arg Pro Gly Gly Arg Arg Arg Gly Arg Leu Pro
```

```
            305                 310                 315                 320
        Asn Asn Ser Ser Arg Pro Ser Thr Pro Thr Ile Asn Val Leu Glu Ser
                        325                 330                 335
        Lys Asp Thr Asp Ser Asp Arg Glu Ala Gly Thr Glu Thr Gly Gly Glu
                        340                 345                 350
        Asn Asn Asp Lys Glu Glu Glu Lys Lys Asp Glu Thr Ser Ser Ser
                        355                 360                 365
        Ser Glu Ala Asn Ser Arg Cys Gln Thr Pro Ile Lys Met Lys Pro Asn
                370                 375                 380
        Ile Glu Pro Pro Glu Asn Val Glu Trp Ser Gly Ala Glu Ala Ser Met
        385                 390                 395                 400
        Phe Arg Val Leu Ile Gly Thr Tyr Tyr Asp Asn Phe Cys Ala Ile Ala
                            405                 410                 415
        Arg Leu Ile Gly Thr Lys Thr Cys Arg Gln Val Tyr Glu Phe Arg Val
                        420                 425                 430
        Lys Glu Ser Ser Ile Ile Ala Pro Ala Pro Ala Glu Asp Val Asp Thr
                        435                 440                 445
        Pro Pro Arg Lys Lys Lys Arg Lys His Arg Leu Trp Ala Ala His Cys
                450                 455                 460
        Arg Lys Ile Gln Leu Lys Lys Asp Gly Ser Ser Asn His Val Tyr Asn
        465                 470                 475                 480
        Tyr Gln Pro Cys Asp His Pro Arg Gln Pro Cys Asp Ser Ser Cys Pro
                            485                 490                 495
        Cys Val Ile Ala Gln Asn Phe Cys Glu Lys Phe Cys Gln Cys Ser Ser
                        500                 505                 510
        Glu Cys Gln Asn Arg Phe Pro Gly Cys Arg Cys Lys Ala Gln Cys Asn
                    515                 520                 525
        Thr Lys Gln Cys Pro Cys Tyr Leu Ala Val Arg Glu Cys Asp Pro Asp
                    530                 535                 540
        Leu Cys Leu Thr Cys Gly Ala Ala Asp His Trp Asp Ser Lys Asn Val
        545                 550                 555                 560
        Ser Cys Lys Asn Cys Ser Ile Gln Arg Gly Ser Lys His Leu Leu
                        565                 570                 575
        Leu Ala Pro Ser Asp Val Ala Gly Trp Gly Ile Phe Ile Lys Asp Pro
                        580                 585                 590
        Val Gln Lys Asn Glu Phe Ile Ser Glu Tyr Cys Gly Glu Ile Ile Ser
                        595                 600                 605
        Gln Asp Glu Ala Asp Arg Arg Gly Lys Val Tyr Asp Lys Tyr Met Cys
                610                 615                 620
        Ser Phe Leu Phe Asn Leu Asn Asn Asp Phe Val Val Asp Ala Thr Arg
        625                 630                 635                 640
        Lys Gly Asn Lys Ile Arg Phe Ala Asn His Ser Val Asn Pro Asn Cys
                        645                 650                 655
        Tyr Ala Lys Val Met Met Val Asn Gly Asp His Arg Ile Gly Ile Phe
                        660                 665                 670
        Ala Lys Arg Ala Ile Gln Thr Gly Glu Glu Leu Phe Phe Asp Tyr Arg
                    675                 680                 685
        Tyr Ser Gln Ala Asp Ala Leu Lys Tyr Val Gly Ile Glu Arg Glu Met
                690                 695                 700
        Glu Ile Pro
        705

<210> SEQ ID NO 6
```

```
<211> LENGTH: 200
<212> TYPE: PRT
<213> ORGANISM: Homo sapiens

<400> SEQUENCE: 6

Ser Cys Pro Cys Val Ile Ala Gln Asn Phe Cys Glu Lys Phe Cys Gln
1               5                   10                  15

Cys Ser Ser Glu Cys Gln Asn Arg Phe Pro Gly Cys Arg Cys Lys Ala
            20                  25                  30

Gln Cys Asn Thr Lys Gln Cys Pro Cys Tyr Leu Ala Val Arg Glu Cys
        35                  40                  45

Asp Pro Asp Leu Cys Leu Thr Cys Gly Ala Ala Asp His Trp Asp Ser
    50                  55                  60

Lys Asn Val Ser Cys Lys Asn Cys Ser Ile Gln Arg Gly Ser Lys Lys
65                  70                  75                  80

His Leu Leu Leu Ala Pro Ser Asp Val Ala Gly Trp Gly Ile Phe Ile
                85                  90                  95

Lys Asp Pro Val Gln Lys Asn Glu Phe Ile Ser Glu Tyr Cys Gly Glu
            100                 105                 110

Ile Ile Ser Gln Asp Glu Ala Asp Arg Arg Gly Lys Val Tyr Asp Lys
        115                 120                 125

Tyr Met Cys Ser Phe Leu Phe Asn Leu Asn Asn Asp Phe Val Val Asp
    130                 135                 140

Ala Thr Arg Lys Gly Asn Lys Ile Arg Phe Ala Asn His Ser Val Asn
145                 150                 155                 160

Pro Asn Cys Tyr Ala Lys Val Met Met Val Asn Gly Asp His Arg Ile
                165                 170                 175

Gly Ile Phe Ala Lys Arg Ala Ile Gln Thr Gly Glu Glu Leu Phe Phe
            180                 185                 190

Asp Tyr Arg Tyr Ser Gln Ala Asp
        195                 200

<210> SEQ ID NO 7
<211> LENGTH: 114
<212> TYPE: PRT
<213> ORGANISM: Homo sapiens

<400> SEQUENCE: 7

His Leu Leu Leu Ala Pro Ser Asp Val Ala Gly Trp Gly Ile Phe Ile
1               5                   10                  15

Lys Asp Pro Val Gln Lys Asn Glu Phe Ile Ser Glu Tyr Cys Gly Glu
            20                  25                  30

Ile Ile Ser Gln Asp Glu Ala Asp Arg Arg Gly Lys Val Tyr Asp Lys
        35                  40                  45

Tyr Met Cys Ser Phe Leu Phe Asn Leu Asn Asn Asp Phe Val Val Asp
    50                  55                  60

Ala Thr Arg Lys Gly Asn Lys Ile Arg Phe Ala Asn His Ser Val Asn
65                  70                  75                  80

Pro Asn Cys Tyr Ala Lys Val Met Met Val Asn Gly Asp His Arg Ile
                85                  90                  95

Gly Ile Phe Ala Lys Arg Ala Ile Gln Thr Gly Glu Glu Leu Phe Phe
            100                 105                 110

Asp Tyr

<210> SEQ ID NO 8
<211> LENGTH: 342
```

<212> TYPE: DNA
<213> ORGANISM: Homo sapiens

<400> SEQUENCE: 8

```
catctattgc tggcaccatc tgacgtggca ggctggggga ttttatcaa agatcctgtg      60
cagaaaaatg aattcatctc agaatactgt ggagagatta tttctcaaga tgaagctgac    120
agaagaggga agtgtatga taaatacatg tgcagctttc tgttcaactt gaacaatgat    180
tttgtggtgg atgcaacccg caagggtaac aaaattcgtt ttgcaaatca ttcggtaaat    240
ccaaactgct atgcaaaagt tatgatggtt aacggtgatc acaggatagg tattttttgcc   300
aagagagcca tccagactgg cgaagagctg tttttttgatt ac                       342
```

<210> SEQ ID NO 9
<211> LENGTH: 746
<212> TYPE: PRT
<213> ORGANISM: Homo sapiens
<220> FEATURE:
<221> NAME/KEY: MISC_FEATURE
<222> LOCATION: (641)..(641)
<223> OTHER INFORMATION: X is any amino acid other than tyrosine (Y).

<400> SEQUENCE: 9

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270
```

```
Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
        290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
        450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
        515                 520                 525

Pro Cys Asp Ser Ser Cys Pro Cys Val Ile Ala Gln Asn Phe Cys Glu
        530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
        610                 615                 620

Gly Ile Phe Ile Lys Asp Pro Val Gln Lys Asn Glu Phe Ile Ser Glu
625                 630                 635                 640

Xaa Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
        675                 680                 685
```

```
His Ser Val Asn Pro Asn Cys Tyr Ala Lys Val Met Met Val Asn Gly
    690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 10
<211> LENGTH: 24
<212> TYPE: PRT
<213> ORGANISM: Homo sapiens

<400> SEQUENCE: 10

Leu Ala Thr Lys Ala Ala Arg Lys Ser Ala Pro Ala Thr Gly Gly Val
1               5                   10                  15

Lys Lys Pro His Arg Tyr Arg Pro
                20

<210> SEQ ID NO 11
<211> LENGTH: 695
<212> TYPE: PRT
<213> ORGANISM: Homo sapiens

<400> SEQUENCE: 11

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
                20                  25                  30

Arg Arg Ala Asp Glu Val Lys Ser Met Phe Ser Ser Asn Arg Gln Lys
            35                  40                  45

Ile Leu Glu Arg Thr Glu Ile Leu Asn Gln Glu Trp Lys Gln Arg Arg
        50                  55                  60

Ile Gln Pro Val His Ile Leu Thr Ser Cys Ser Val Thr Ser Asp Leu
65                  70                  75                  80

Asp Phe Pro Thr Gln Val Ile Pro Leu Lys Thr Leu Asn Ala Val Ala
                85                  90                  95

Ser Val Pro Ile Met Tyr Ser Trp Ser Pro Leu Gln Gln Asn Phe Met
            100                 105                 110

Val Glu Asp Glu Thr Val Leu His Asn Ile Pro Tyr Met Gly Asp Glu
        115                 120                 125

Val Leu Asp Gln Asp Gly Thr Phe Ile Glu Glu Leu Ile Lys Asn Tyr
    130                 135                 140

Asp Gly Lys Val His Gly Asp Arg Glu Cys Gly Phe Ile Asn Asp Glu
145                 150                 155                 160

Ile Phe Val Glu Leu Val Asn Ala Leu Gly Gln Tyr Asn Asp Asp Asp
                165                 170                 175

Asp Asp Asp Asp Gly Asp Pro Glu Glu Arg Glu Glu Lys Gln Lys
            180                 185                 190

Asp Leu Glu Asp His Arg Asp Asp Lys Glu Ser Arg Pro Pro Arg Lys
        195                 200                 205

Phe Pro Ser Asp Lys Ile Phe Glu Ala Ile Ser Ser Met Phe Pro Asp
    210                 215                 220

Lys Gly Thr Ala Glu Glu Leu Lys Glu Lys Tyr Lys Glu Leu Thr Glu
225                 230                 235                 240
```

```
Gln Gln Leu Pro Gly Ala Leu Pro Pro Glu Cys Thr Pro Asn Ile Asp
                245                 250                 255
Gly Pro Asn Ala Lys Ser Val Gln Arg Glu Gln Ser Leu His Ser Phe
        260                 265                 270
His Thr Leu Phe Cys Arg Arg Cys Phe Lys Tyr Asp Cys Phe Leu His
    275                 280                 285
Pro Phe His Ala Thr Pro Asn Thr Tyr Lys Arg Lys Asn Thr Glu Thr
290                 295                 300
Ala Leu Asp Asn Lys Pro Cys Gly Pro Gln Cys Tyr Gln His Leu Glu
305                 310                 315                 320
Gly Ala Lys Glu Phe Ala Ala Ala Leu Thr Ala Glu Arg Ile Lys Thr
                325                 330                 335
Pro Pro Lys Arg Pro Gly Gly Arg Arg Arg Gly Arg Leu Pro Asn Asn
            340                 345                 350
Ser Ser Arg Pro Ser Thr Pro Thr Ile Asn Val Leu Glu Ser Lys Asp
        355                 360                 365
Thr Asp Ser Asp Arg Glu Ala Gly Thr Glu Thr Gly Gly Glu Asn Asn
    370                 375                 380
Asp Lys Glu Glu Glu Glu Lys Lys Asp Glu Thr Ser Ser Ser Ser Glu
385                 390                 395                 400
Ala Asn Ser Arg Cys Gln Thr Pro Ile Lys Met Lys Pro Asn Ile Glu
                405                 410                 415
Pro Pro Glu Asn Val Glu Trp Ser Gly Ala Glu Ala Ser Met Phe Arg
            420                 425                 430
Val Leu Ile Gly Thr Tyr Tyr Asp Asn Phe Cys Ala Ile Ala Arg Leu
        435                 440                 445
Ile Gly Thr Lys Thr Cys Arg Gln Val Tyr Glu Phe Arg Val Lys Glu
    450                 455                 460
Ser Ser Ile Ile Ala Pro Ala Pro Ala Glu Asp Val Asp Thr Pro Pro
465                 470                 475                 480
Arg Lys Lys Lys Arg Lys His Arg Leu Trp Ala Ala His Cys Arg Lys
                485                 490                 495
Ile Gln Leu Lys Lys Gly Gln Asn Arg Phe Pro Gly Cys Arg Cys Lys
            500                 505                 510
Ala Gln Cys Asn Thr Lys Gln Cys Pro Cys Tyr Leu Ala Val Arg Glu
        515                 520                 525
Cys Asp Pro Asp Leu Cys Leu Thr Cys Gly Ala Ala Asp His Trp Asp
530                 535                 540
Ser Lys Asn Val Ser Cys Lys Asn Cys Ser Ile Gln Arg Gly Ser Lys
545                 550                 555                 560
Lys His Leu Leu Leu Ala Pro Ser Asp Val Ala Gly Trp Gly Ile Phe
                565                 570                 575
Ile Lys Asp Pro Val Gln Lys Asn Glu Phe Ile Ser Glu Tyr Cys Gly
            580                 585                 590
Glu Ile Ile Ser Gln Asp Glu Ala Asp Arg Arg Gly Lys Val Tyr Asp
        595                 600                 605
Lys Tyr Met Cys Ser Phe Leu Phe Asn Leu Asn Asn Asp Phe Val Val
    610                 615                 620
Asp Ala Thr Arg Lys Gly Asn Lys Ile Arg Phe Ala Asn His Ser Val
625                 630                 635                 640
Asn Pro Asn Cys Tyr Ala Lys Val Met Met Val Asn Gly Asp His Arg
                645                 650                 655
Ile Gly Ile Phe Ala Lys Arg Ala Ile Gln Thr Gly Glu Glu Leu Phe
```

```
                660             665             670
Phe Asp Tyr Arg Tyr Ser Gln Ala Asp Ala Leu Lys Tyr Val Gly Ile
            675             680             685

Glu Arg Glu Met Glu Ile Pro
        690             695

<210> SEQ ID NO 12
<211> LENGTH: 2682
<212> TYPE: DNA
<213> ORGANISM: Homo sapiens

<400> SEQUENCE: 12
gacgacgttc gcggcgggga actcggagta gcttcgcctc tgacgtttcc ccacgacgca      60
ccccgaaatc cccctgagct ccggcggtcg cgggctgccc tcgccgcctg gtctggcttt     120
atgctaagtt tgagggaaga gtcgagctgc tctgctctct attgattgtg tttctggagg     180
gcgtcctgtt gaattcccac ttcattgtgt acatcccctt ccgttccccc caaaaatctg     240
tgccacaggg ttactttttg aaagcgggag gaatcgagaa gcacgatctt ttggaaaact     300
tggtgaacgc ctaaataatc atgggccaga ctgggaagaa atctgagaag ggaccagttt     360
gttggcggaa gcgtgtaaaa tcagagtaca tgcgactgag acagctcaag aggttcagac     420
gagctgatga agtaaagagt atgtttagtt ccaatcgtca gaaattttg gaagaacgg      480 aaatcttaaa ccaagaatgg aaacagcgaa ggatacagcc tgtgcacatc ctgacttctt     540
gttcggtgac cagtgacttg gattttccaa cacaagtcat cccattaaag actctgaatg     600
cagttgcttc agtacccata atgtattctt ggtctcccct acagcagaat ttatggtgg      660 aagatgaaac tgttttacat aacattcctt atatgggaga tgaagttta gatcaggatg     720 gtactttcat tgaagaacta ataaaaaatt atgatgggaa agtacacggg gatagagaat     780 gtgggttat aaatgatgaa attttgtgg agttggtgaa tgcccttggt caatataatg      840
atgatgacga tgatgatgat ggagacgatc ctgaagaaag agaagaaaag cagaaagatc     900
tggaggatca ccgagatgat aaagaaagcc gcccacctcg gaaatttcct tctgataaaa     960
tttttgaagc catttcctca atgtttccag ataagggcac agcagaagaa ctaaaggaaa    1020
aatataaaga actcaccgaa cagcagctcc caggcgcact tcctcctgaa tgtaccccca    1080
acatagatgg accaaatgct aaatctgttc agagagagca aagcttacac tcctttcata    1140
cgcttttctg taggcgatgt tttaaatatg actgcttcct acatcctttt catgcaacac    1200
ccaacactta taagcggaag aacacagaaa cagctctaga caacaaacct tgtgaccac     1260 agtgttacca gcatttggag ggagcaaagg agtttgctgc tgctctcacc gctgagcgga    1320
taaagacccc accaaaacgt ccaggaggcc gcagaagagg acggcttccc aataacagta    1380
gcaggcccag cacccccacc attaatgtgc tggaatcaaa ggatacagac agtgataggg    1440
aagcagggac tgaaacgggg ggagagaaca atgataaaga agaagaagag aagaaagatg    1500
aaacttcgag ctcctctgaa gcaaattctc ggtgtcaaac accaataaag atgaagccaa    1560
atattgaacc tcctgagaat gtggagtgga gtggtgctga agcctcaatg tttagagtcc    1620
tcattggcac ttactatgac aatttctgtg ccattgctag gttaattggg accaaaacat    1680
gtagacaggt gtatgagttt agagtcaaag aatctagcat catagctcca gctcccgctg    1740
aggatgtgga tactcctcca aggaaaaaga gaggaaaaca ccggttgtgg gctgcacact    1800
gcagaaagat acagctgaaa aagggtcaaa accgctttcc gggatgccgc tgcaaagcac    1860
agtgcaacac caagcagtgc ccgtgctacc tggctgtccg agagtgtgac cctgacctct    1920
```

```
gtcttacttg tggagccgct gaccattggg acagtaaaaa tgtgtcctgc aagaactgca    1980
gtattcagcg gggctccaaa aagcatctat tgctggcacc atctgacgtg gcaggctggg    2040 ggattttat caaagatcct gtgcagaaaa atgaattcat ctcagaatac tgtggagaga    2100
ttatttctca agatgaagct gacagaagag ggaaagtgta tgataaatac atgtgcagct    2160
ttctgttcaa cttgaacaat gattttgtgg tggatgcaac ccgcaagggt aacaaaattc    2220
gttttgcaaa tcattcggta aatccaaact gctatgcaaa agttatgatg gttaacggtg    2280
atcacaggat aggtattttt gccaagagag ccatccagac tggcgaagag ctgttttttg    2340
attacagata cagccaggct gatgccctga agtatgtcgg catcgaaaga gaaatggaaa    2400
tcccttgaca tctgctacct cctcccccct cctctgaaac agctgcctta gcttcaggaa    2460
cctcgagtac tgtgggcaat ttagaaaaag aacatgcagt ttgaaattct gaatttgcaa    2520
agtactgtaa gaataattta tagtaatgag tttaaaaatc aacttttat tgccttctca    2580 ccagctgcaa agtgttttgt accagtgaat ttttgcaata atgcagtatg gtacattttt    2640
caactttgaa taaagaatac ttgaacttgt ccttgttgaa tc                      2682
```